United States Patent
Zhou et al.

(10) Patent No.: US 10,316,070 B2
(45) Date of Patent: Jun. 11, 2019

(54) DUAL PROTECTED PRO-COELENTERAZINE SUBSTRATES

(71) Applicant: PROMEGA CORPORATION, Madison, WI (US)

(72) Inventors: Wenhui Zhou, San Luis Obispo, CA (US); Joel R. Walker, San Luis Obispo, CA (US); Poncho Meisenheimer, San Luis Obispo, CA (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 15/699,846

(22) Filed: Sep. 8, 2017

(65) Prior Publication Data
US 2018/0072781 A1 Mar. 15, 2018

Related U.S. Application Data

(60) Provisional application No. 62/385,701, filed on Sep. 9, 2016.

(51) Int. Cl.
| | |
|---|---|
| *C12N 15/85* | (2006.01) |
| *C07D 487/04* | (2006.01) |
| *C07D 519/00* | (2006.01) |
| *C07K 14/435* | (2006.01) |

(52) U.S. Cl.
CPC ...... *C07K 14/43595* (2013.01); *C07D 487/04* (2013.01); *C07D 519/00* (2013.01); *C12N 15/8509* (2013.01); *A01K 2217/05* (2013.01)

(58) Field of Classification Search
CPC .............. A01K 2217/05; C07D 487/04; C07D 519/00; C07K 14/43595; C12N 15/8509
See application file for complete search history.

(56) References Cited

U.S. PATENT DOCUMENTS

| | | | |
|---|---|---|---|
| 7,728,118 | B2 | 6/2010 | Wood et al. |
| 8,557,970 | B2 | 10/2013 | Encell et al. |
| 2005/0153310 | A1 | 7/2005 | Fan et al. |
| 2006/0068395 | A1 | 3/2006 | Wood et al. |
| 2008/0070299 | A1 | 3/2008 | Wood et al. |
| 2008/0090291 | A1 | 4/2008 | Wood et al. |
| 2008/0248511 | A1 | 10/2008 | Daily et al. |
| 2009/0253131 | A1 | 10/2009 | Wigdal et al. |
| 2009/0305280 | A1 | 12/2009 | Binkowski et al. |
| 2010/0281552 | A1 | 11/2010 | Encell |
| 2012/0107849 | A1 | 5/2012 | Klaubert et al. |
| 2012/0117667 | A1 | 5/2012 | Klaubert et al. |
| 2012/0149046 | A1 | 6/2012 | Meighan et al. |
| 2015/0191768 | A1 | 7/2015 | Szczepanik et al. |

FOREIGN PATENT DOCUMENTS

| | | |
|---|---|---|
| WO | WO 2003/040100 | 5/2003 |
| WO | WO 2007/120522 | 10/2007 |
| WO | WO 2010/127368 | 11/2010 |
| WO | WO 2012/061477 | 5/2012 |

OTHER PUBLICATIONS

Inoue et al. (Chem. Lett. (1987) pp. 417-418).*
Banaszynski et al., "Characterization of the FKBP-Rapamycin-FRB Ternary Complex" J. Am. Chem. Soc, 127(13):4715-4721(2005).
Berge et al., "Pharmaceutical Salts" J. Pharm. Sci., 66:1-19 (1977).
Burbelo et al., "Antibody-profiling technologies for studying humoral responses to infectious agents" Expert Review of Vaccines 9(6):567-578(2010).
Carruthers, Some Modern Methods of Organic Synthesis, 3rd Edition, Cambridge University Press, Cambridge, 1987.
Chenna et al., "Multiple sequence alignment with the Clustal series of programs" Nucl. Acids Res. 31(13):3497-3500 (2003).
Chothia et al., "The relation between the divergence of sequence and structure in proteins" EMBO J. 5(4):823-826 (1986).
Cross et al., "Organinc Chemistry Division Commiccion on Nomeclature of Organic Chemistry," Pure Appl. Chem., 1976, 45: 13-30.
Dennell, R. et al., "Observations on the luminescence of bathypelagic crustacea decapoda of the Bermuda area," Zool. J. Linn. Soc., London (1955) XLII:393-406.
Freifelder et al. "Synthesis of Primary 1,2-Diamines by Hydrogenation of alpha-Aminonitriles" Journal of the American Chemical Society, 82(3):696-698(1960).
Furniss, Hannaford, Smith, and Tatchell, "Vogel's Textbook of Practical Organic Chemistry", 5th edition (1989).
GenBank 1VPR (2009).
Green, T et al., "Protective Groups in Organic Synthesis" Third Edition (1999).
Gross et al., "Real-time imaging of ligand-induced IKK activation in intact cells and in living mice" Nature Methods 2(8):607-614 (2005).

(Continued)

*Primary Examiner* — Valerie Rodriguez-Garcia
(74) *Attorney, Agent, or Firm* — Casimir Jones, S.C.; Anne M. Reynolds

(57) ABSTRACT

Described are coelenterazine analogs, methods for making the analogs, kits comprising the analogs, and methods of using the compounds for the detection of luminescence in luciferase-based assays with low backgrounds and enhanced signal-to-background ratios. The coelenterazine analogs include compounds of formula (I):

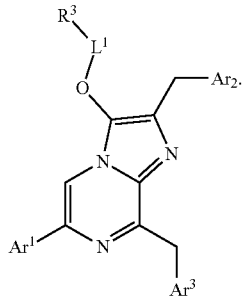

20 Claims, 3 Drawing Sheets

Specification includes a Sequence Listing.

(56) References Cited

OTHER PUBLICATIONS

Hagedorn et al., "Darstellung von α.β-ungesattigten Isonitrilen, β-Keto- und β-Chlor-isonitrilen. Synthese des Xanthocillin-dimethylathers" Chem. Ber., 98:193(1965).

Inoue et al. "Squid bioluminescence. II. Isolation from Watasenia scintillans and synthesis of 2-(p-hydroxybenzyl)-6-(p-hydroxphenyl)-3,7-dihydroimidazo[1,2-a]pyrazin-3-one" Chem. Lett., 4(2):141-144 (1975).

Inouye et al. "The Use of Renilla Luciferase, Oplophorus Luciferase, and Apoaequorin as Bioluminescent Reporter Protein in the Presence of Coelenterazine Analogues as Substrate" BBRC, 223:349-353 (1997).

Kakoi et al., "A New Synthesis of Watasenia Preluciferin by Cylization of 2-Amino-3-Benzyl-5-(p-Hydroxphenyl)Pyrazine with p-Hydroxyphenylpyruviacc," Chem. Lett. 11(3):299-300 (1980).

Kakoi, "Synthesis of 2-Amino-3-benzyl-5-(p-hydroxyphenyl)pyrazine" Chem. Pharm. Bull., 50:301 (2002).

Kishi et al., "The structure confirmation of the light-emitting moiety of bioluminescent jellyfish" Tetrahedron Lett. 13(27):2747(1972).

Langley et al., "Molecular Basis of O-Galactosidase a-Complementation PNAS (protein sequencing/protein conformation/deletion mutant)" 72:1254-1257 (1975).

Larock, Comprehensive Organic Transformations, VCH Publishers, Inc., New York, 1989.

Levit et al., "Ribonuclease S-Peptide—A Model for Molecular Recognition" J. Biol. Chem. 251:1333-1339 (1976).

Moroz et al., "Real-Time Imaging of HIF-1a Stabilization and Degradation" Plos One 4(4):e5077 (2009).

Mosrin et al., "Regio- and Chemoselective Multiple Functionalization of Chloropyrazine Derivatives. Application to the Synthesis of Coelenterazine" Organic Letters, 11:3406 (2009).

Murray, E.E. et al., "Codon usage in plant genes," Nucl. Acids. Res. (1989) 17(2):477-498.

Needleman, S.B. et al., "A general method applicable to the search for similarities in the amino acid sequence of two proteins," J. Mol. Biol. (1970) 48:443-453.

Ohana et al., "HaloTag7: A genetically engineered tag that enhances bacterial expression of soluble proteins and improves protein purification" Protein Expression and Purification, 68:110-120 (2009).

Paguio et al., "pGL4 Vectors: A New Generation fo Luciferase Reporter Vectors" Promega Notes, 89:7-10 (2005).

Pearson, W.R. et al., "Improved tools for biological sequence comparison," Proc. Natl. Acad. Sci. USA (1988) 85:2444-2448.

Poupin, J., "Plancton marin bioluminescent," Rapport Scientifique du Leon (Sep. 1999) 1-83.

Raphael et al., "A novel method for multiple alignment of sequences with repeated and shuffled elements" Genome Res. 14(11):2336-2346 (2004).

Schagat, T. et al., "KRX autoinduction protocol: a convenient metod for protein expression," Promega Notes (2008) 98:16-18.

Sigrist et al., "PROSITE, a protein domain database for functional characterization and annotation" Nucleic Acids Res. 38(suppl 1):D161-D166(2010).

Smith and March, March's Advanced Organic Chemistry, 5th Edition, John Wiley & Sons, Inc., New York, 2001.

Smith, T.F. et al., "Identification of common molecular subsequences," J. Mol. Biol. (1981) 147:195-197.

Sorrel, Organic Chemistry, Second Edition, University Science Books, Sausalito, 1999.

Tramontano, "Comparative modelling techniques: where are we?" Genomics, 4:402-405 (2003).

Wada, K. et al., "Codon usage tabulated from the GenBank genetic sequence data," Nucl. Acids Res. (1990) 18(Supp):2367-2411.

Wuts and Greene, Greene's Protective Groups in Organic Synthesis (4th ed.), John Wiley & Sons, NY, 2006.

Zhang et al., "A Universal Algorithm for Fast and Automated Charge State Deconvolution of Electrospray Mass-to-Charge Ratio Spectra" J. Am. Soc. Mass Spectrom., 9:225-233 (1998).

Zheng et al., "An efficient one-step site-directed and site-saturation mutagenesis protocol" Nucleic Acids Research, 32:e115 (2004).

Zuker et al., "Mfold web server for nucleic acid folding and hybridization prediction" Nucleic Acid Res. 31(13):3406-3415(2003).

International Search Report and Written Opinion for Application No. PCT/US2017/050792 dated Nov. 29, 2017 (14 pages).

* cited by examiner

SEQUENCE LISTING

```
<160> NUMBER OF SEQ ID NOS: 11

<210> SEQ ID NO 1
<211> LENGTH: 4
<212> TYPE: PRT
<213> ORGANISM: Artificial
<220> FEATURE:
<223> OTHER INFORMATION: Synthetic Peptide

<400> SEQUENCE: 1

Asp Glu Val Asp
1

<210> SEQ ID NO 2
<211> LENGTH: 4
<212> TYPE: PRT
<213> ORGANISM: Artificial
<220> FEATURE:
<223> OTHER INFORMATION: Synthetic Peptide

<400> SEQUENCE: 2

Leu Glu Thr Asp
1

<210> SEQ ID NO 3
<211> LENGTH: 4
<212> TYPE: PRT
<213> ORGANISM: Artificial
<220> FEATURE:
<223> OTHER INFORMATION: Synthetic Peptide

<400> SEQUENCE: 3

Leu Glu His Asp
1

<210> SEQ ID NO 4
<211> LENGTH: 5
<212> TYPE: PRT
<213> ORGANISM: Artificial
<220> FEATURE:
<223> OTHER INFORMATION: Synthetic Peptide

<400> SEQUENCE: 4

Val Asp Val Ala Asp
1               5

<210> SEQ ID NO 5
<211> LENGTH: 4
<212> TYPE: PRT
<213> ORGANISM: Artificial
<220> FEATURE:
<223> OTHER INFORMATION: Synthetic Peptide

<400> SEQUENCE: 5

Leu Leu Val Tyr
1

<210> SEQ ID NO 6
<211> LENGTH: 4
<212> TYPE: PRT
<213> ORGANISM: Artificial
<220> FEATURE:
<223> OTHER INFORMATION: Synthetic Peptide

<400> SEQUENCE: 6

Gln Glu Val Tyr
1
```

```
<210> SEQ ID NO 7
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Modified leucine amino acid
<220> FEATURE:
<221> NAME/KEY: MISC_FEATURE
<222> LOCATION: (3)..(3)
<223> OTHER INFORMATION: Modified leucine amino acid

<400> SEQUENCE: 7

Leu Pro Leu Asp
1

<210> SEQ ID NO 8
<211> LENGTH: 4
<212> TYPE: PRT
<213> ORGANISM: Artificial
<220> FEATURE:
<223> OTHER INFORMATION: Synthetic Peptide

<400> SEQUENCE: 8

Ile Glu Pro Asp
1

<210> SEQ ID NO 9
<211> LENGTH: 4
<212> TYPE: PRT
<213> ORGANISM: Artificial
<220> FEATURE:
<223> OTHER INFORMATION: Synthetic Peptide

<400> SEQUENCE: 9

Ile Glu Thr Asp
1

<210> SEQ ID NO 10
<211> LENGTH: 6
<212> TYPE: PRT
<213> ORGANISM: Artificial
<220> FEATURE:
<223> OTHER INFORMATION: Synthetic Peptide

<400> SEQUENCE: 10

Thr Ser Ala Val Leu Gln
1               5

<210> SEQ ID NO 11
<211> LENGTH: 6
<212> TYPE: PRT
<213> ORGANISM: Artificial
<220> FEATURE:
<223> OTHER INFORMATION: Synthetic Peptide

<400> SEQUENCE: 11

Val Asn Ser Thr Leu Gln
1               5
```

DUAL PROTECTED PRO-COELENTERAZINE SUBSTRATES

RELATED APPLICATIONS

This application claims the benefit of U.S. provisional application Ser. No. 62/385,701, filed Sep. 9, 2016, which is incorporated herein by reference in its entirety.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Sep. 8, 2017, is named ASFILED_SequenceListing.txt, and is 2,082 bytes in size.

TECHNICAL FIELD

The present disclosure relates to coelenterazine analogues, methods for making coelenterazine analogues, and methods of using coelenterazine analogues in luciferase-based assays.

BACKGROUND

Bioluminescent assays are used extensively in the investigation of cellular physiology, especially processes associated with gene expression. In particular, luciferase reporter enzymes are quite valuable tools in this field, and, to date, there has been intense protein engineering to obtain small and environmentally insensitive luciferases that may be useful in bioluminescent assays. There exist a number of efficient luciferase reporters that enable whole-cell biosensor measurements, drug discovery through high-throughput screening, and in vivo imaging, that also permit the study of protein-protein interactions in living cells, apoptosis, and cell viability. Luciferases that use coelenterazine and coelenterazine analogues as substrates are among the most widely used systems due to their brightness and acceptance in whole cell applications.

SUMMARY OF THE INVENTION

Many known coelenterazine analogues have deficiencies, which limit their effectiveness as luciferase substrates and usefulness in luciferase-based assays. These deficiencies include cell toxicity, light sensitivity, thermodynamic instability, low aqueous solubility, and low cell permeability. For example, the signal to background ratio in assays based on pro-coelenterazines or pro-furimazines (a coelenterazine analogue) are often limited by background luminescence. With even the faintest cage group hydrolysis, the background can increase over time causing a temporary decrease in signal-to-background. Low signal-to-background windows often limit practical applications such as live-dead cell assays, cell apoptosis, bacteria, fungi or mold detections, or detection of activity of any target enzyme of interest in vitro or in cells. Accordingly, there exists a need for coelenterazine analogues with improved properties and methods for synthesizing the analogues.

In one aspect, disclosed are compounds of formula (I),

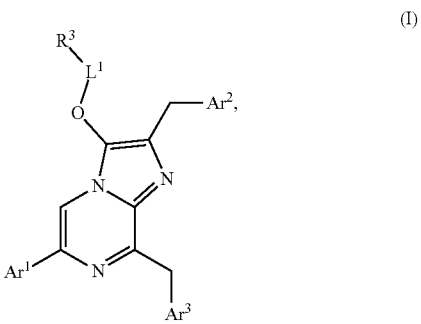

or a tautomer, or a salt thereof, wherein $Ar^1$, $Ar^2$, and $Ar^3$ are each independently selected from the group consisting of aryl and heteroaryl, wherein $Ar^1$, $Ar^2$, and $Ar^3$ are each optionally substituted, provided that one of $Ar^1$, $Ar^2$, or $Ar^3$ is substituted by $-X-L^2-R^6$; is O, S, or $NR^x$, wherein $R^x$ is hydrogen or $C_1$-$C_6$-alkyl; $L^1$ and $L^2$ are each independently selected from the group consisting of a bond and a linker of 1 to 50 atoms, wherein $L^1$ and $L^2$ are each optionally substituted; and $R^3$ and $R^6$ are each independently selected from an enzyme substrate group.

Also disclosed are methods of making the compounds, kits comprising the compounds, and methods of using the compounds as luciferase substrates in luciferase-based assays.

FIGURES

DETAILED DESCRIPTION

Figure 1:
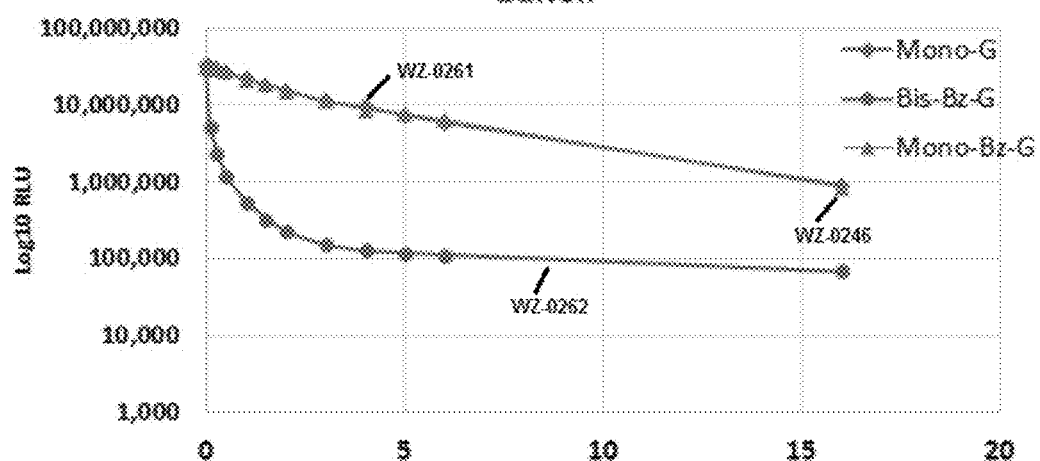
FIG. 1 shows the luminescent signal output of the disclosed dual-protected compounds relative to mono-protected analogues.

Disclosed herein are dual-protected coelenterazine analogues. The dual-protected coelenterazine analogues may be substrates for a non-luminescent enzyme and pro-substrates for a luminescent protein. Once acted on by the non-luminescent enzyme of interest, the analogue can become a substrate for a luminescent protein. The dual-protected coelenterazine analogues can be useful pro-substrates for proteins that utilize coelenterazine ("coelenterazine-utilizing enzymes") to produce luminescence, including, but not limited to, luciferases and photoproteins found in various marine organisms such as cnidarians (e.g., *Renilla* luciferase), jellyfish (e.g., aequorin from the *Aequorea* jellyfish), and decapods luciferases (e.g., luciferase complex of *Oplophorus gracilirostris*). The disclosed compounds can exhibit unexpectedly, extremely low background in comparison to mono-protected compound counterparts. In general, the backgrounds for the dual-protected prosubstrates are 2-3 orders magnitude lower than mono-protected substrates, and the background signal is very stable over a long period of time. The disclosed dual-protected coelenterazine analogues provide great potential by enabling new assays due to the significant improvement in sensitivity for many applications. A dual pro-coelenterazine-based assay is a non-lytic, homogeneous, bioluminescent method to determine target enzyme/reactive species in real time format.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 10 carbon atoms with at least one carbon-carbon double bond. The alkenyl group may be substituted or unsubstituted. For example, the alkenyl group may be substituted with an aryl group, such as a phenyl.

The term "alkynyl" as used herein, means a hydrocarbon chain containing from 2 to 10 carbon atoms with at least one carbon-carbon triple bond. The alkynyl group may be substituted or unsubstituted. For example, the alkynyl group may be substituted with an aryl group, such as a phenyl.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "amino acid" refers to both natural and unnatural amino acids. It also includes protected natural and unnatural amino acids.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "enzyme substrate" as used herein, refers to a group or a portion thereof, of a parent molecular moiety or compound that is subject to enzymatic modification. When an enzyme substrate is modified by an enzyme, preferably this effects cleavage of the enzyme substrate from the parent molecular moiety, and, if present, the linker between the enzyme substrate and the parent molecular moiety. Examples of enzyme substrates include, but are not limited to, peptides, amino acids, saccharides, and phosphates, all of which may be attached to the parent molecular moiety directly or through a linker by a selected covalent modification. Suitable enzymes to act on an enzyme substrate include, but are not limited to Glucosidases, Galacosidase, Glucuronidase, Neuraiminidase, phosphatase, Caspases 3/7, Caspase 6, Caspase 8, Caspase 9, Caspase 2, Dipeptidyl peptidase 4 (DPPIV), Calpain and Chymotrypsin-like proteasome proteases, Trypsin-like proteoasome protease, Caspase-like proteasome protease, Granzyme B, Cathepsins B/L, Cathepsin K, Thrombin, Trypsin, Aminopeptidase, SARS protease, Glutathione-S-transferase, CYP450, reductase, and dehydrogenase.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups include a monocyclic heteroaryl ring fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups include a monocyclic heteroaryl ring fused to two of a monocyclic cycloalkyl group, as defined herein, a monocyclic aryl group, as defined herein, a monocyclic heteroaryl group, as defined herein, or a monocyclic heterocycle, as defined herein. In some embodiments, the bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. In some embodiments, the tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "linker" may refer to a chain of 1 to 50 atoms that link a substrate moiety to a parent molecular moiety. Linkers may include one or more heteroatoms (e.g., $NR^{x1}$, O, S, NO, SO and $SO_2$, wherein $R^{x1}$ at each occurrence is independently selected from the group consisting of hydrogen and $C_1$-$C_6$-alkyl). Linkers may also be substituted (e.g., oxo groups, amino groups, alkyl groups, halogens and nitro groups). Linkers may contain aryl groups. The linkers may be "traceless" or "self-immolative" linkers. The term "traceless linker" or "self-immolative linker" refers to a linker wherein cleavage of the substrate moiety from the linker results in spontaneous cleavage of the linker from the coelenterazine core to release coelenterazine or a coelenterazine analogue.

The term "peptide" refers to a sequence of at least two amino acids. In some embodiments, a peptide may contain no more than 80 amino acids, or no more than 35 amino acids, or no more than 10 amino acids. Exemplary peptides include Asp-Glu-Val-Asp (SEQ ID NO:1), Leu-Glu-Thr-Asp (SEQ ID NO:2), Leu-Glu-His-Asp (SEQ ID NO:3), Val-Asp-Val-Ala-Asp (SEQ ID NO:4), Gly-Pro, Val-Pro, Leu-Leu-Val-Tyr (SEQ ID NO:5), Gln-Glu-Val-Tyr (SEQ ID NO:6), Leu-Arg-Arg, norLeu-Pro-norLeu-Asp (SEQ ID NO:7), Ile-Glu-Pro-Asp (SEQ ID NO:8), Ile-Glu-Thr-Asp (SEQ ID NO:9), Phe-Arg, Leu-Arg, Gly-Pro-Arg, Gly-Gly-Arg, Gly-Lys, Ala-Ala-Phe, Thr-Ser-Ala-Val-Leu-Gln (SEQ ID NO:10), and Val-Asn-Ser-Thr-Leu-Gln (SEQ ID NO:11), Gly-Phe, Phe-Arg, Leu-Arg, z-VVR (e.g. Cbz-VVR), Leu-Cit, and Gly-Cit. Both z and Cbz may be a benzyloxy carbamate group, and may be an amine protecting group for the attached peptide.

The term "saccharide" refers to a sugar or other carbohydrate, especially a simple sugar. It includes both the alpha- and the beta-anomers. The saccharide can be a $C_6$-polyhydroxy compound, typically a $C_6$-pentahydroxy, and often a cyclic glycal. It includes the known simple sugars and their derivatives, as well as polysaccharides with two or more monosaccharide residues. The saccharide can include protecting groups on the hydroxyl groups. The hydroxyl groups of the saccharide can be replaced with one or more acetamido, halo or amino groups. Additionally, one or more of the carbon atoms can be oxidized, for example to keto or carbonyl groups. Suitable saccharides include galactose, glucose, glucoronic acid and neurominic acid.

The term "substituted" refers to a group that may be further substituted with one or more non-hydrogen substituent groups. Exemplary substituent groups are halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

Disclosed are compounds of formula (I):

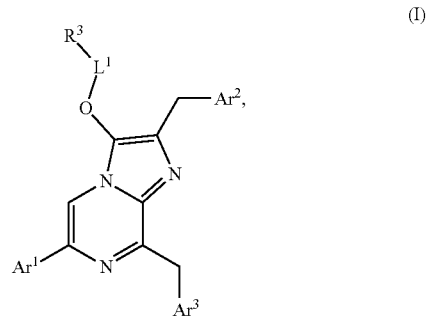

or a tautomer, or a salt thereof, wherein $Ar^1$, $Ar^2$, and $Ar^3$ are each independently selected from the group consisting of aryl and heteroaryl, wherein $Ar^1$, $Ar^2$, and $Ar^3$ are each optionally substituted, provided that one of $Ar^1$, $Ar^2$, or $Ar^3$ is substituted by —X-$L^2$-$R^6$;

X is O, S, or $NR^x$, wherein $R^x$ is hydrogen or $C_1$-$C_6$-alkyl;

$L^1$ and $L^2$ are each independently selected from the group consisting of a bond and a linker of 1 to 50 atoms, wherein $L^1$ and $L^2$ are each optionally substituted; and $R^3$ and $R^6$ are each independently selected from an enzyme substrate group.

In certain embodiments, $Ar^1$, $Ar^2$, and $Ar^3$ are each independently selected from the group consisting of aryl and heteroaryl, wherein $Ar^1$, $Ar^2$, and $Ar^3$ are each independently substituted by 0, 1, 2, 3, 4, 5, 6, 7, 8, 9, or 10 substituents independently selected from the group consisting of halogen, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl, provided that one of $Ar^2$, or $Ar^3$ is substituted by —X-$L^2$-$R^6$.

In certain embodiments, $Ar^1$ is phenyl, $Ar^2$ is furyl or phenyl, and $Ar^3$ is phenyl, wherein $Ar^1$, $Ar^2$, and $Ar^3$ are each independently substituted by 0, 1, 2, 3, 4, 5, 6, 7, 8, 9, or 10 substituents independently selected from the group consisting of halogen, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl, provided that one of $Ar^1$, $Ar^2$, or $Ar^3$ is substituted by —X-$L^2$-$R^6$.

In certain embodiments, $Ar^1$ is substituted with —X-$L^2$-$R^6$. In certain embodiments, $Ar^1$ is phenyl substituted with —X-$L^2$-$R^6$. In certain embodiments, $Ar^1$ is phenyl substituted with —X-$L^2$-$R^6$ at the 2-position. In certain embodiments, $Ar^1$ is phenyl substituted with —X-$L^2$-$R^6$ at the 3-position. In certain embodiments, $Ar^1$ is phenyl substituted with —X-$L^2$-$R^6$ at the 4-position.

In certain embodiments, $Ar^2$ is substituted with —X-$L^2$-$R^6$. In certain embodiments, $Ar^2$ is furan-2-yl substituted with —X-$L^2$-$R^6$. In certain embodiments, $Ar^2$ is furan-2-yl substituted with —X-$L^2$-$R^6$ at the 3-position. In certain embodiments, $Ar^2$ is furan-2-yl substituted with —X-$L^2$-$R^6$ at the 4-position. In certain embodiments, $Ar^2$ is furan-2-yl substituted with —X-$L^2$-$R^6$ at the 5-position. In certain embodiments, $Ar^2$ is phenyl substituted with —X-$L^2$-$R^6$. In certain embodiments, $Ar^2$ is phenyl substituted with —X-$L^2$-$R^6$ at the 2-position. In certain embodiments, $Ar^2$ is phenyl substituted with —X-$L^2$-$R^6$ at the 3-position. In certain embodiments, $Ar^2$ is phenyl substituted with —X-$L^2$-$R^6$ at the 4-position.

In certain embodiments, when $Ar^2$ is substituted with —X-$L^2$-$R^6$, $Ar^2$ is phenyl. In certain embodiments, when $Ar^2$ is substituted with —X-$L^2$-$R^6$, $Ar^2$ is not furyl.

In certain embodiments, $Ar^3$ is substituted with —X-$L^2$-$R^6$. In certain embodiments, $Ar^3$ is phenyl substituted with —X-$L^2$-$R^6$. In certain embodiments, $Ar^3$ is phenyl substituted with —X-$L^2$-$R^6$ at the 2-position. In certain embodiments, $Ar^3$ is phenyl substituted with —X-$L^2$-$R^6$ at the 3-position. In certain embodiments, $Ar^3$ is phenyl substituted with —X-$L^2$-$R^6$ at the 4-position.

In certain embodiments, X is O. In certain embodiments, X is S. In certain embodiments, X is $NR^x$. In certain embodiments, X is $NR^x$ wherein $R^x$ is hydrogen. In certain embodiments, X is $NR^x$ wherein $R^x$ is $C_1$-$C_6$-alkyl. In certain embodiments, X is $NR^x$ wherein $R^x$ is methyl.

In certain embodiments, $L^1$ and $L^2$ are each independently a bond, alkylene, or arylenealkylene; wherein one or more of the —CH$_2$— moieties in the alkylene chain portion of alkylene or arylenealkylene are optionally replaced by C=O, C=S, $NR^{x1}$, O, S, NO, SO and $SO_2$, wherein $R^{x1}$ at each occurrence is independently selected from the group consisting of hydrogen and $C_1$-$C_6$-alkyl; wherein alkylene and arylenealkylene are each independently substituted by 0, 1, 2, 3, 4, 5, 6, 7, 8, 9, or 10 substituents independently selected from the group consisting of halogen, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $L^1$ and $L^2$ are each independently selected from the group consisting of:

a bond;

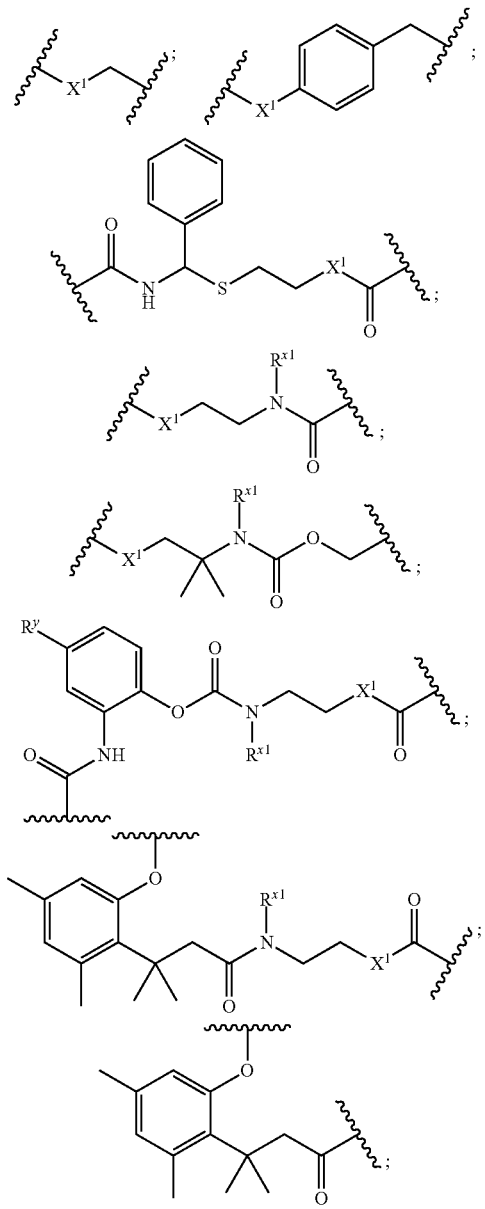

-continued

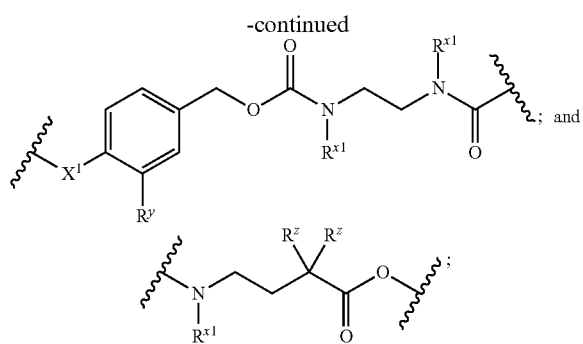

wherein $R^{x1}$ at each occurrence is independently selected from the group consisting of hydrogen and $C_1$-$C_6$-alkyl; $R^y$ is selected from the group consisting of hydrogen, halogen, and nitro; $R^z$ at each occurrence is independently selected from the group consisting of hydrogen and $C_1$-$C_6$-alkyl; and $X^1$ is selected from the group consisting of $NR^{x2}$, O, and S, wherein $R^{x2}$ is hydrogen or $C_1$-$C_6$-alkyl.

In certain embodiments, $L^1$ and $L^2$ are each independently selected from the group consisting of:

a bond;

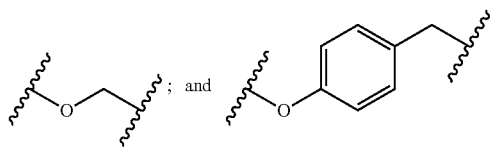

In certain embodiments, $L^1$ and $L^2$ are each a bond.

In certain embodiments, $R^3$ and $R^6$ are each independently a moiety derived from a group selected from the group consisting of a peptide, an amino acid, a saccharide, and a phosphate. In certain embodiments, $R^3$ and $R^6$ are each independently a moiety derived from a peptide. In certain embodiments, $R^3$ and $R^6$ are each independently a moiety derived from an amino acid. In certain embodiments, $R^3$ and $R^6$ are each independently a moiety derived from a saccharide. In certain embodiments, $R^3$ and $R^6$ are each independently a moiety derived from a galactose, glucose, glucoronic acid, neurominic acid, or a derivative or analogue thereof. In certain embodiments, $R^3$ and $R^6$ are each independently a moiety derived from a phosphate group.

In certain embodiments, $R^3$ and $R^6$ are each independently selected from the group consisting of:

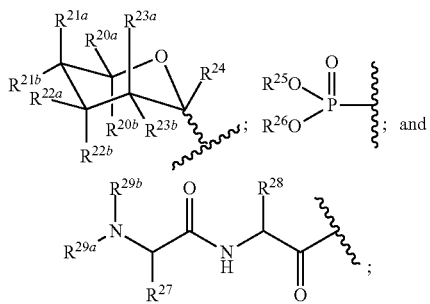

wherein $R^{20a}$ and $R^{20b}$ are each independently selected from the group consisting of hydrogen, halogen, and $C_1$-$C_6$-alkyl optionally substituted with 1, 2, 3, or 4 —$OR^{30}$ groups and optionally 1 oxo group, wherein $R^{30}$ at each occurrence is independently selected from the group consisting of hydrogen, $C_1$-$C_6$-alkyl, and $C(=O)R^{31}$, wherein $R^{31}$ is $C_1$-$C_6$-alkyl; $R^{21a}$, $R^{21b}$, $R^{22a}$, $R^{22b}$, $R^{23a}$, and $R^{23b}$ at each occurrence are each independently selected from the group consisting of hydrogen, halogen, $OR^{32}$ and $NR^{33}R^{34}$, wherein $R^{32}$—$R^{34}$ at each occurrence are each independently selected from the group consisting of hydrogen, $C_1$-$C_6$-alkyl, and $C(=O)R^{35}$, wherein $R^{35}$ is hydrogen or $C_1$-$C_6$-alkyl; $R^{24}$ at each occurrence is independently selected from the group consisting of hydrogen and $C(=O)R^{36}$, wherein $R^{36}$ is selected from the group consisting of hydrogen, $C_1$-$C_6$-alkyl, —OH, and —O—$C_1$-$C_6$-alkyl; $R^{25}$ and $R^{26}$ are each independently selected from the group consisting of hydrogen, and $C_1$-$C_6$-alkyl; $R^{27}$ and $R^{28}$ are each independently selected from the group consisting of:

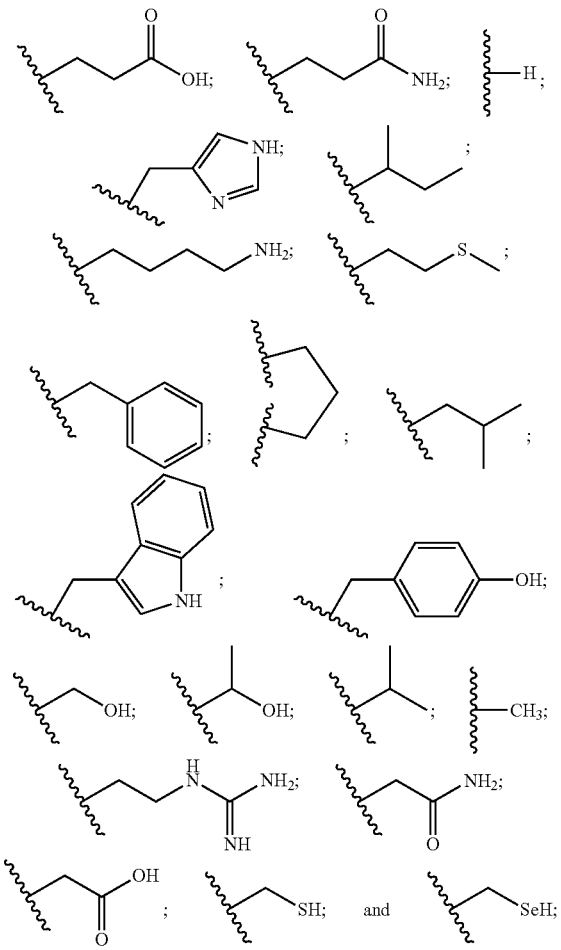

and $R^{29a}$ and $R^{29b}$ are each independently hydrogen, or $R^{29a}$ and $R^{27}$ together with the atoms to which they are attached can form a five-membered ring.

In certain embodiments, $R^3$ and $R^6$ are each independently selected from the group consisting of:

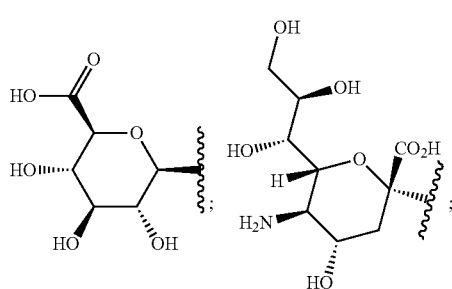

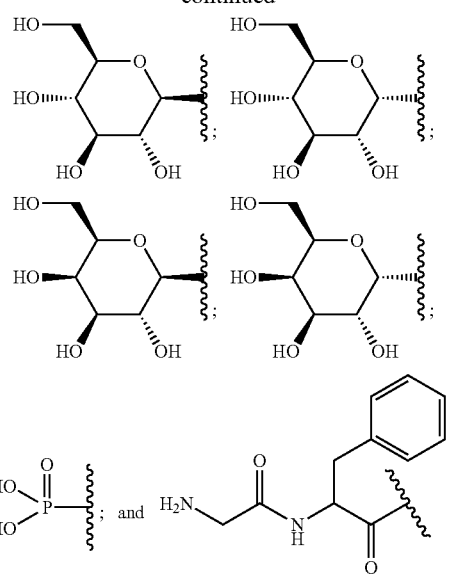
In certain embodiments, the compound of formula (I) has formula:
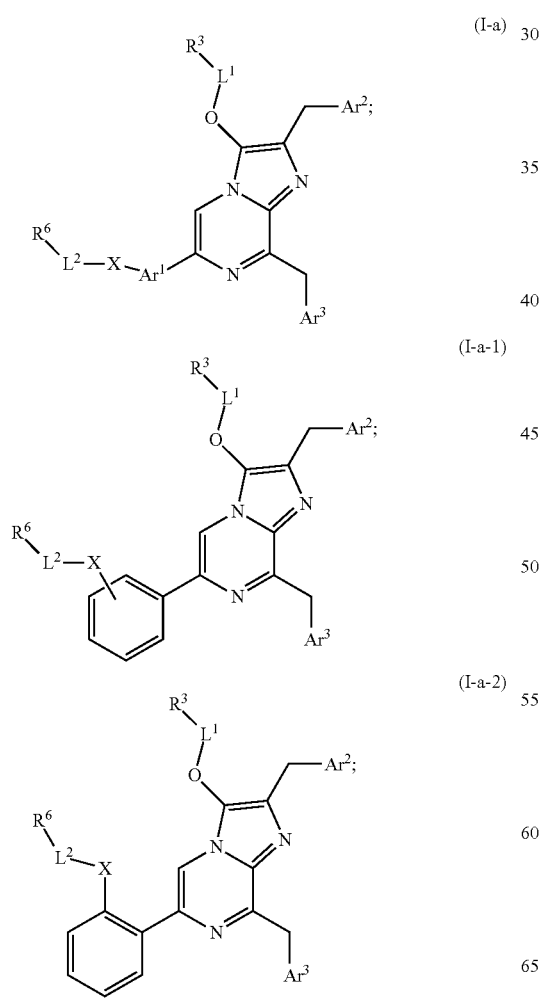
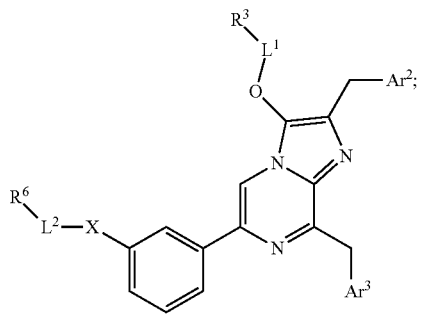
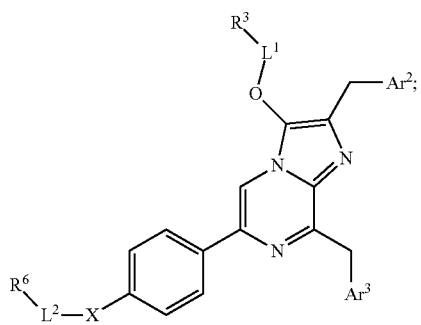
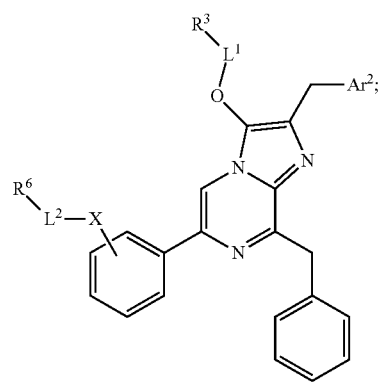
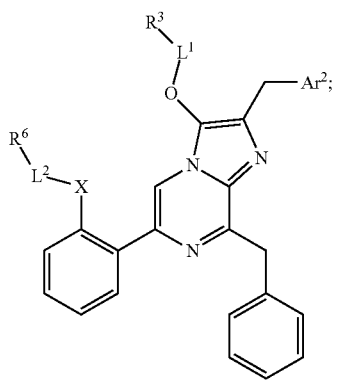

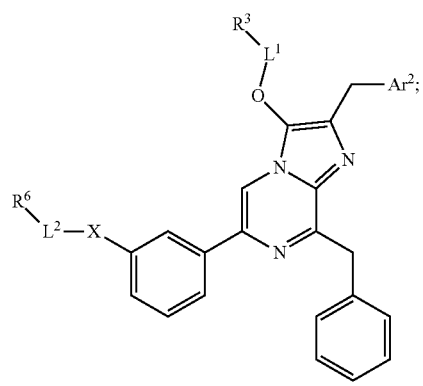
(I-a-7)
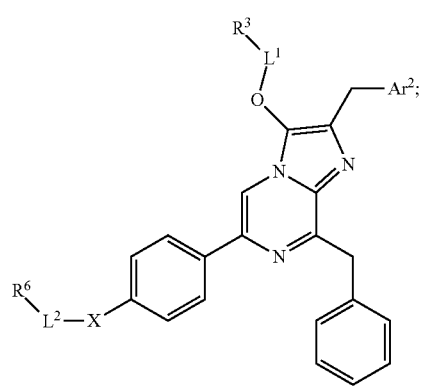
(I-a-8)
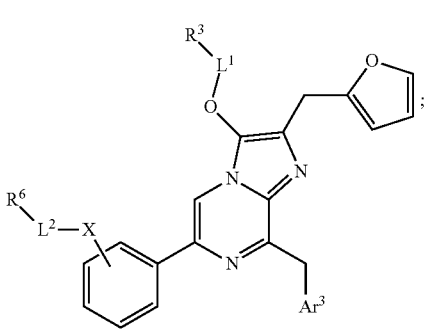
(I-a-9)
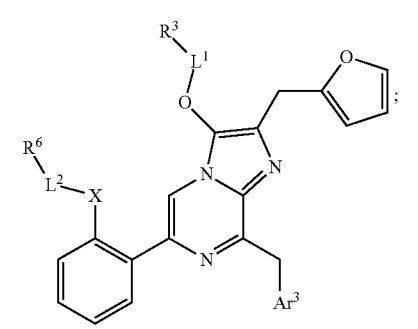
(I-a-10)
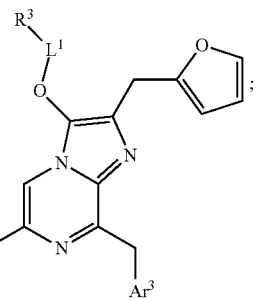
(I-a-11)
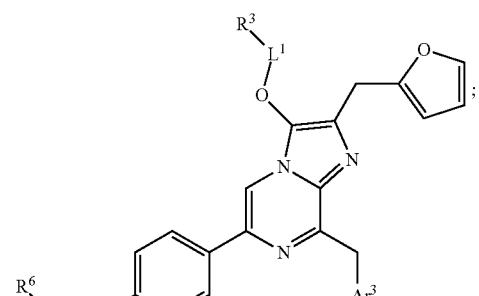
(I-a-12)
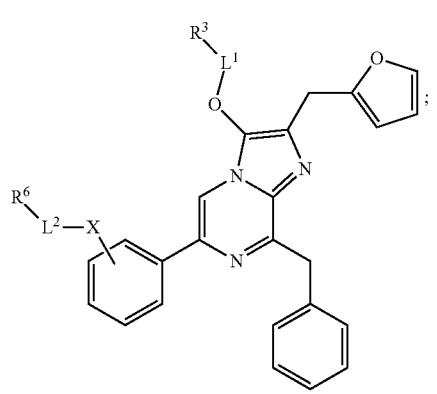
(I-a-13)
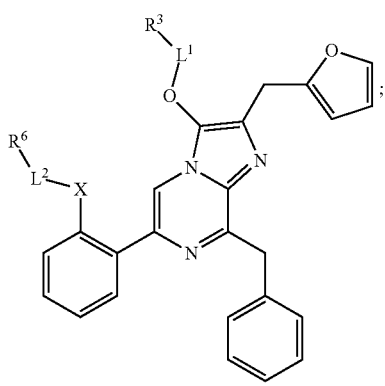
(I-a-14)

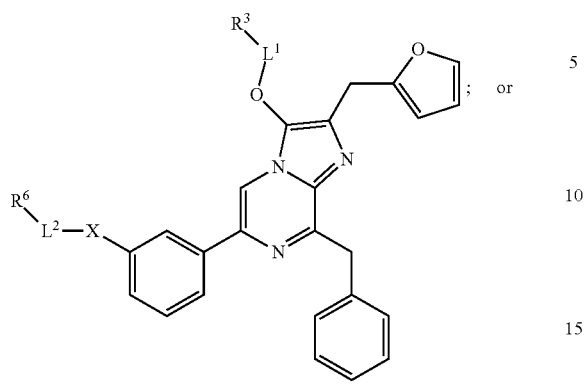
(I-a-15)
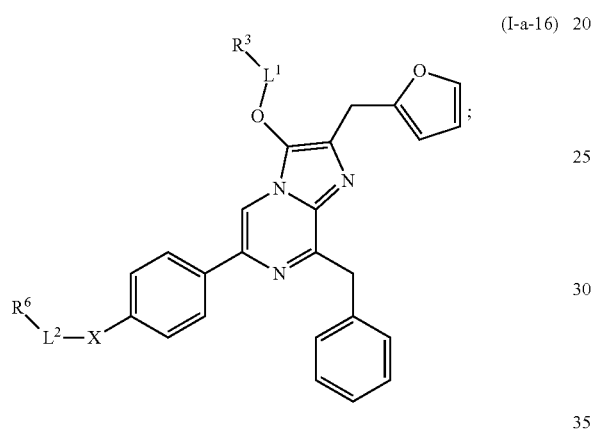
(I-a-16)
wherein Ar¹, Ar², Ar³, X, L¹, L², R³, and R⁶ are as defined above.
In certain embodiments, the compound of formula (I) has formula:
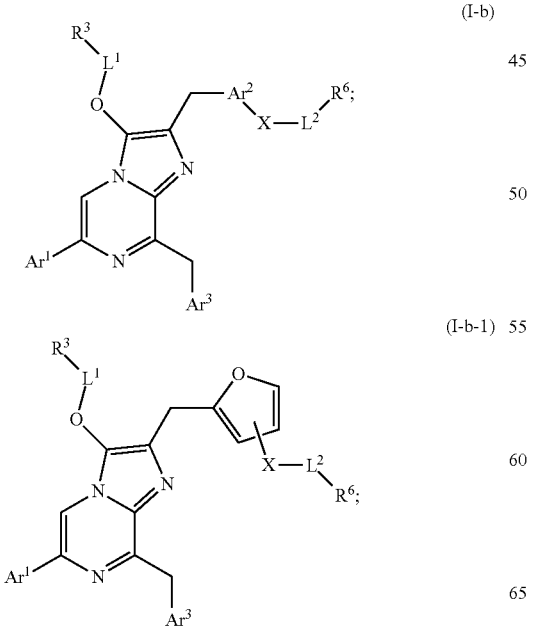
(I-b)
(I-b-1)
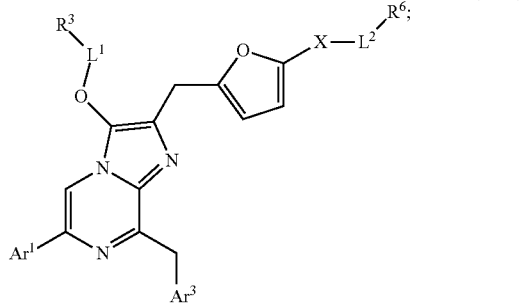
(I-b-2)
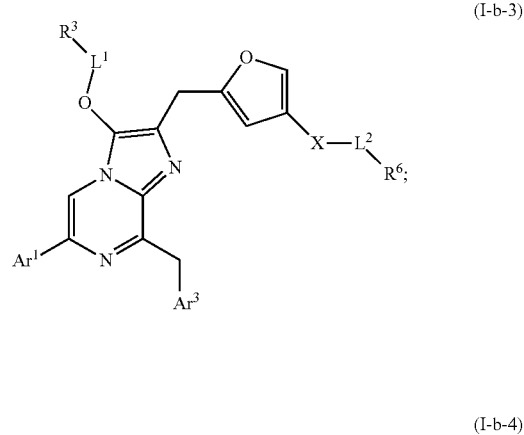
(I-b-3)
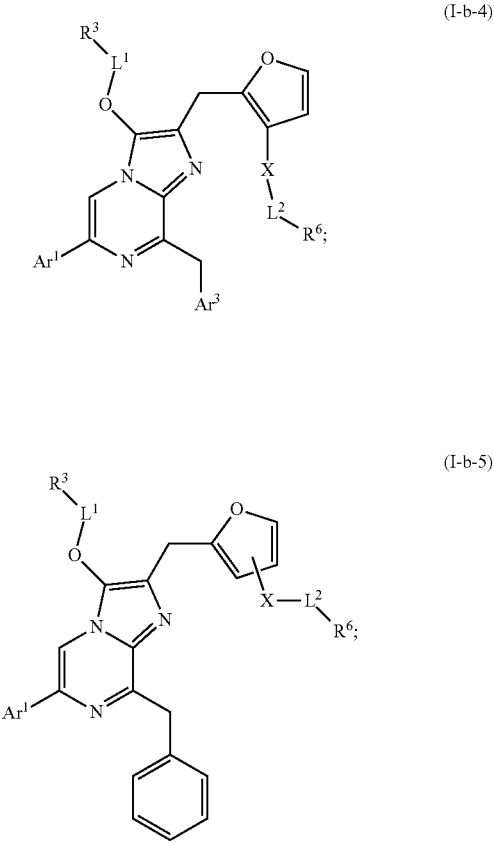
(I-b-4)
(I-b-5)

-continued
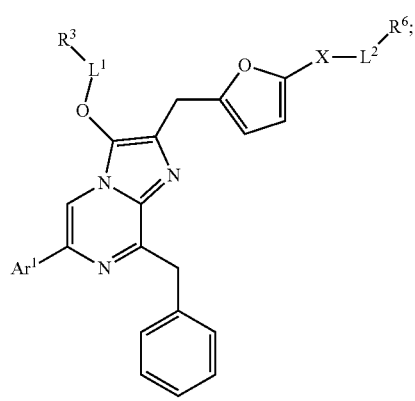
(I-b-6)
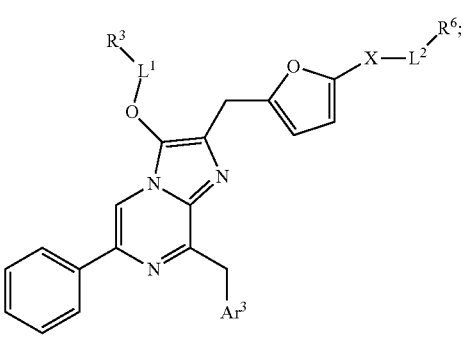
(I-b-10)
(I-b-7)
(I-b-11)
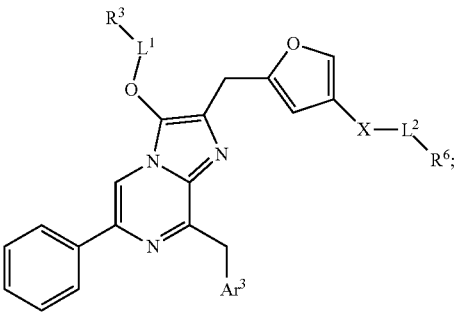
(I-b-8)
(I-b-12)
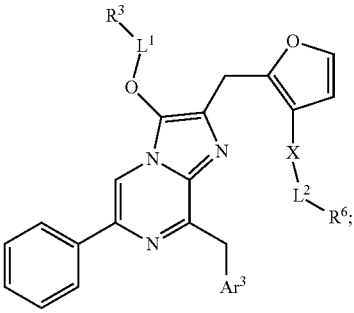
(I-b-9)
(I-b-13)
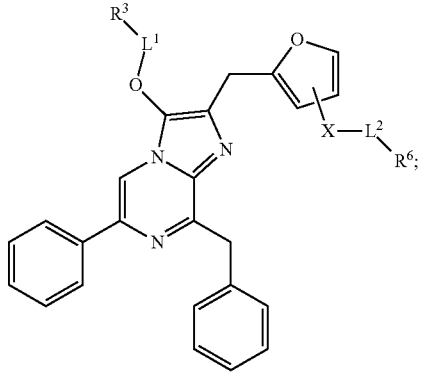

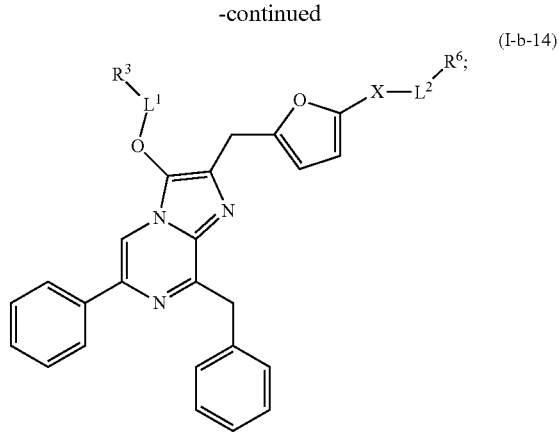
(I-b-14)
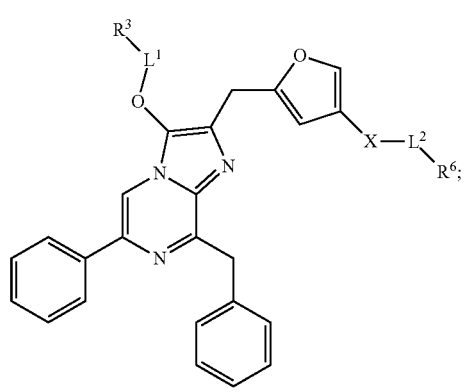
(I-b-15)
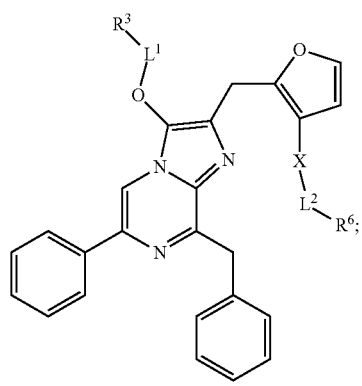
(I-b-16)
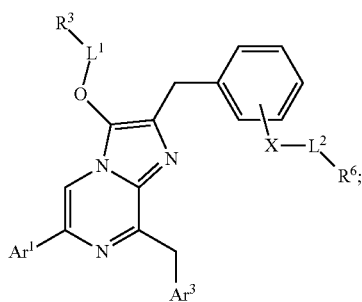
(I-b-17)
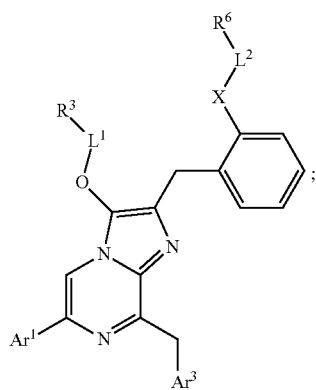
(I-b-18)
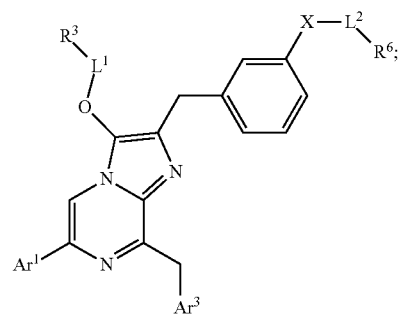
(I-b-19)
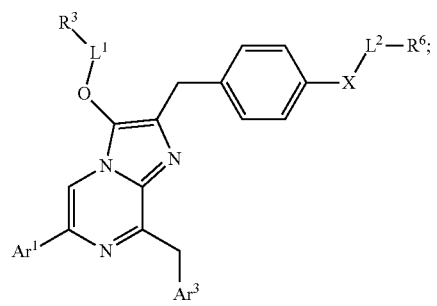
(I-b-20)
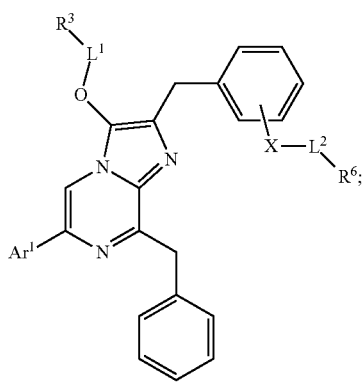
(I-b-21)

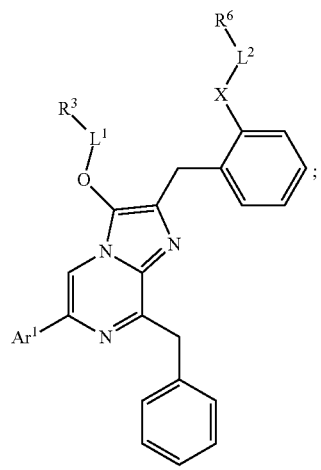
(I-b-22)
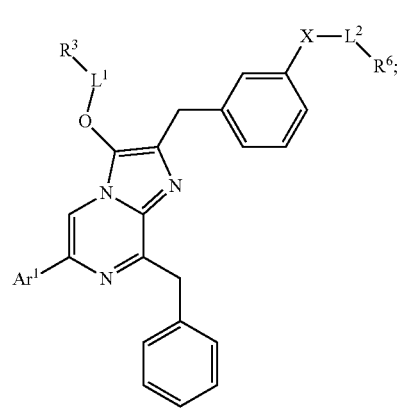
(I-b-23)
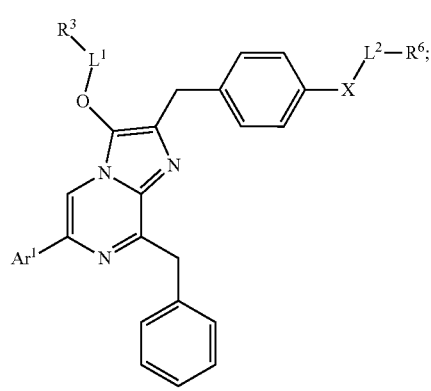
(I-b-24)
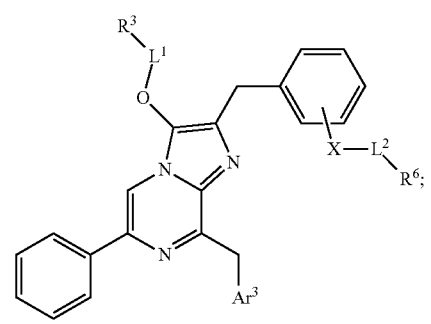
(I-b-25)
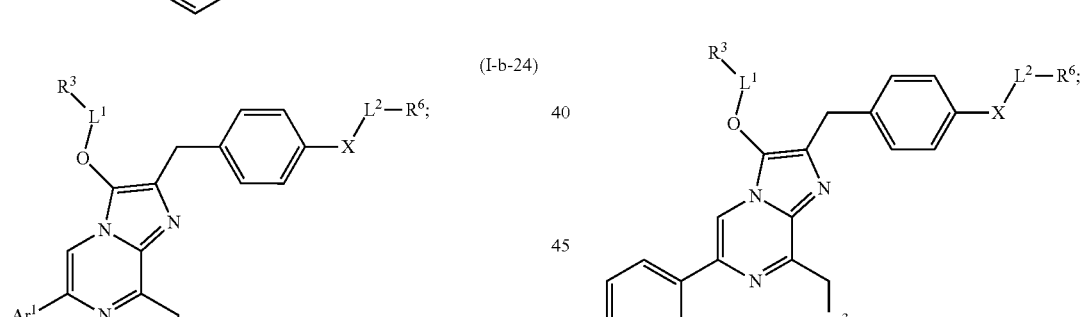
(I-b-26)
(I-b-27)
(I-b-28)
(I-b-29)

(I-b-30)
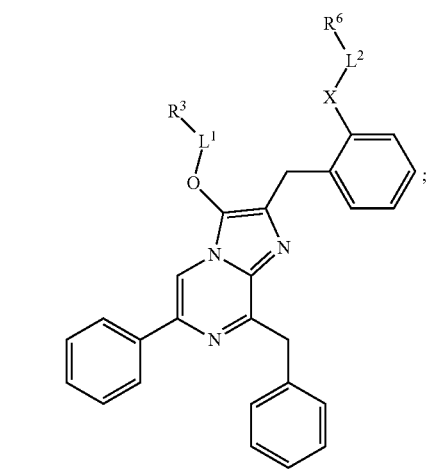
(I-b-31)
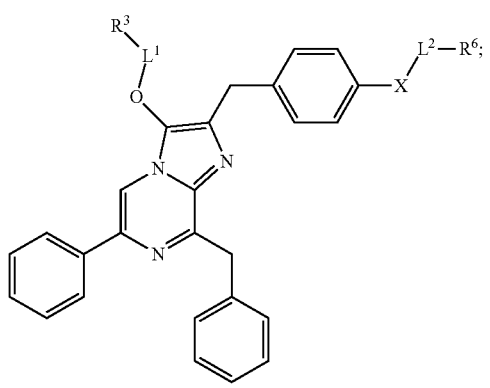
or
(I-b-32)
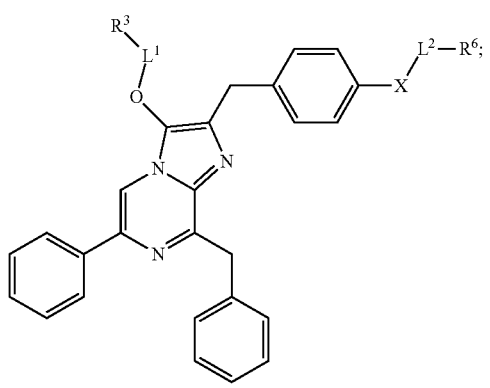
wherein Ar¹, Ar², Ar³, X, L¹, L², R³, and R⁶ are as defined above.
In certain embodiments, the compound of formula (I) has formula:
(I-c)
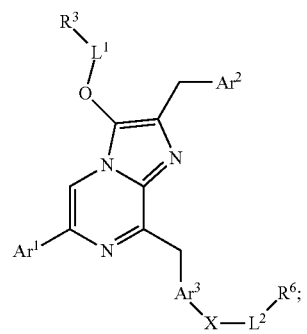
(I-c-1)
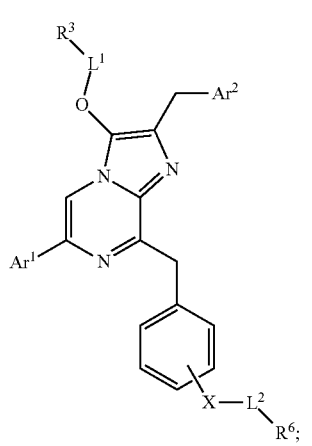
(I-c-2)
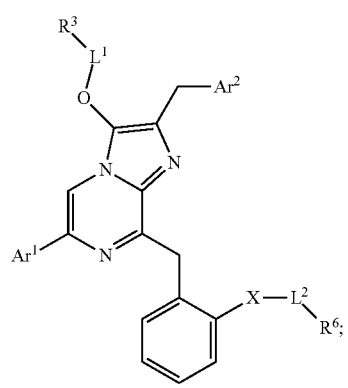
(I-c-3)
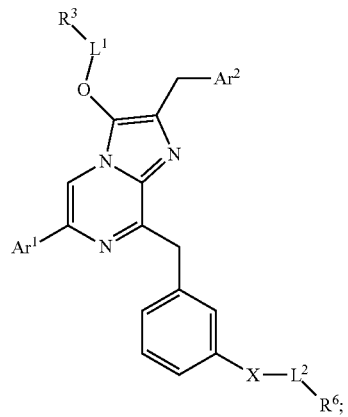

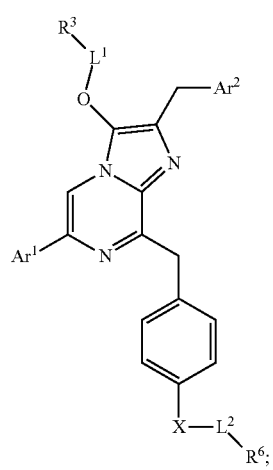
(I-c-4)
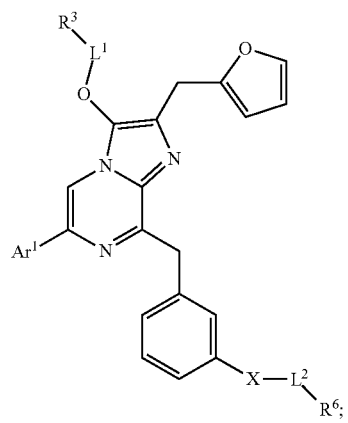
(I-c-7)
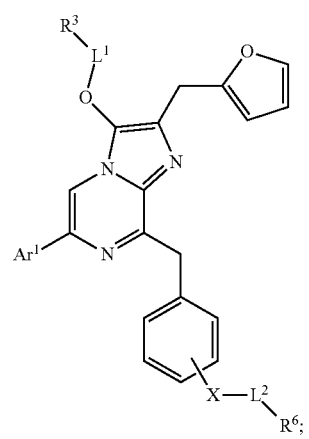
(I-c-5)
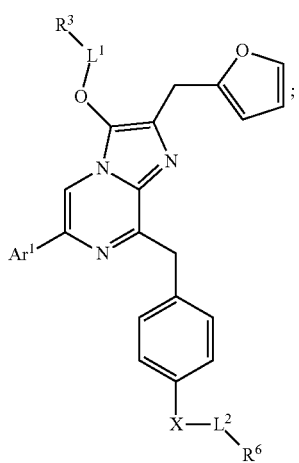
(I-c-8)
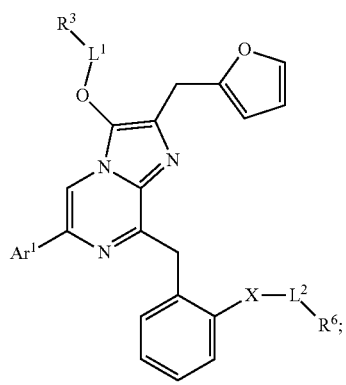
(I-c-6)
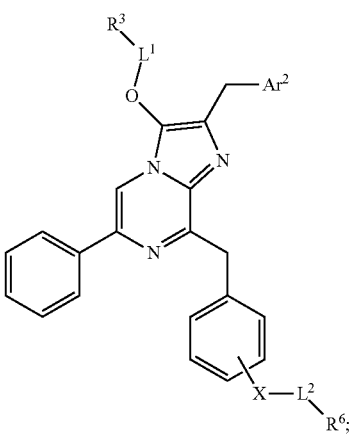
(I-c-9)

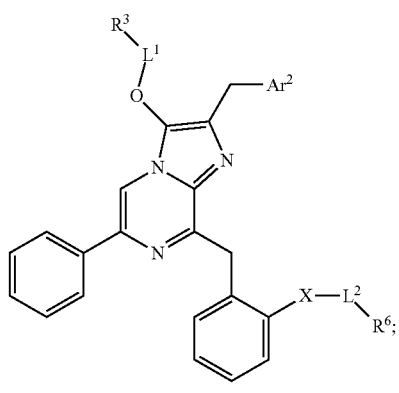
(I-c-10)
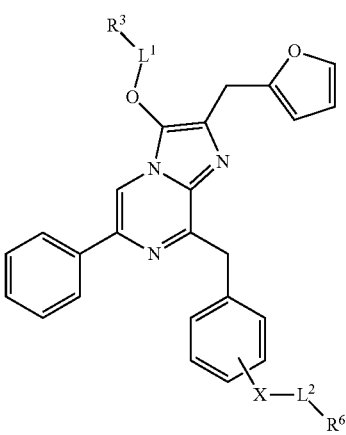
(I-c-13)
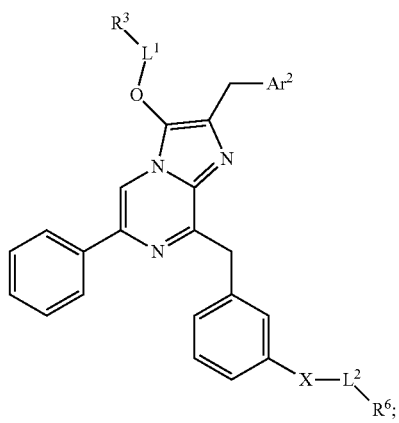
(I-c-11)
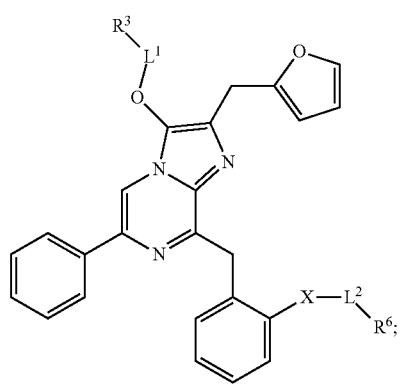
(I-c-14)
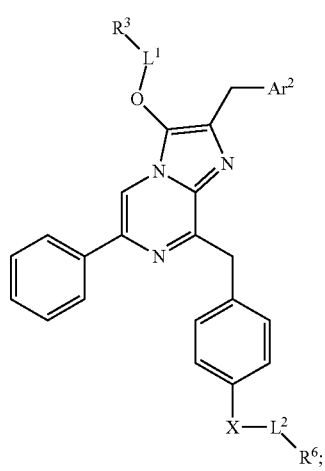
(I-c-12)
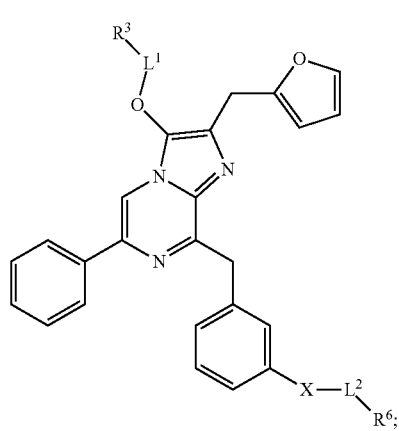
(I-c-15) or (I-c-16)

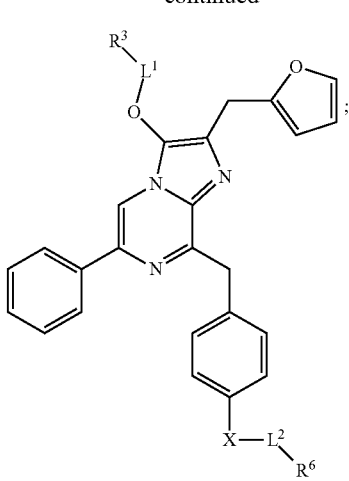

wherein Ar¹, Ar², Ar³, X, L¹, L², R³, and R⁶ are as defined above.

Representative compounds of formula (I) include, but are not limited to:

(2S,3R,4S,5S,6R)-2-(4-(8-benzyl-2-(furan-2-ylmethyl)-3-((4-(((2S,3R,4S,5S,6R)-3,4,5-trihydroxy-6-(hydroxymethyl)tetrahydro-2H-pyran-2-yl)oxy)benzyl)oxy)imidazo[1,2-a]pyrazin-6-yl)phenoxy)-6-(hydroxymethyl)tetrahydro-2H-pyran-3,4,5-triol;

4-(((8-benzyl-2-(furan-2-ylmethyl)-6-(3-(phosphonooxy)phenyl)imidazo[1,2-a]pyrazin-3-yl)oxy)methyl)phenyl dihydrogen phosphate;

2-(2-aminoacetamido)-N-(3-(3-((4-(2-(2-aminoacetamido)-3-phenylpropanamido)benzyl)oxy)-8-benzyl-2-(furan-2-ylmethyl)imidazo[1,2-a]pyrazin-6-yl)phenyl)-3-phenylpropanamide;

(2S,3R,4S,5S,6R)-2-(4-(8-benzyl-2-(furan-2-ylmethyl)-3-(((2S,3R,4S,5S,6R)-3,4,5-trihydroxy-6-(hydroxymethyl)tetrahydro-2H-pyran-2-yl)oxy)imidazo[1,2-a]pyrazin-6-yl)phenoxy)-6-(hydroxymethyl;

((8-benzyl-2-(furan-2-ylmethyl)-6-(3-(phosphonooxy)phenyl)imidazo[1,2-a]pyrazin-3-yl)oxy)methyl phosphate; and the salts thereof, and tautomers thereof.

Compound names are assigned by using Struct=Name naming algorithm as part of CHEMDRAW® ULTRA v. 12.0.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5$^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^{2}$H, can afford certain therapeutic advantages resulting from greater metabolic stability, for example increased in vivo half-life or reduced dosage requirements, and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Properties of the Compounds

The compounds of formula (I) may be substrates of luciferases to produce luminescence. The compounds may have improved water solubility, improved stability, improved cell permeability, increased biocompatibility with cells, reduced autoluminescence, and/or reduced toxicity. The disclosed compounds can exhibit unexpectedly superior background performance (signal/background) in comparison to other coelenterazine and furimazine analogues (e.g., mono-protected compound coelenterazine and furimazine analogues). In general, the backgrounds for the dual-protected prosubstrates are 2-3 orders magnitude lower than mono-protected substrates, and the background signal is very stable over a long period of time (e.g., 24 hours). The disclosed dual-protected coelenterazine analogues provide great potential by enabling new assays due to the significant improvement in sensitivity for many applications.

"Luminescence" refers to the light output of a luciferase under appropriate conditions, e.g., in the presence of a suitable substrate such as a coelenterazine analogue. The light output may be measured as an instantaneous or near-instantaneous measure of light output (which is sometimes referred to as "T=0" luminescence or "flash") at the start of the luminescence reaction, which may be initiated upon addition of the coelenterazine substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., coelenterazine analogue, buffer, etc., into a reaction chamber (e.g., a well of a multiwell plate such as a 96-well plate) containing the luminescent protein. In still other embodiments, the luciferase and/or coelenterazine analogues (e.g., compounds of formula (I)) are introduced into a host, and measurements of luminescence are made on the host or a portion thereof, which can include a whole organism or cells, tissues, explants, or extracts thereof. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

Compounds of formula (I) can generate RLUs greater than or equal to 1, greater than or equal to 2, greater than or equal to 3, greater than or equal to 4, greater than or equal to 5, greater than or equal to 10, greater than or equal to 20, greater than or equal to 30, greater than or equal to 40, greater than or equal to 50, or greater than or equal to 100, relative to coelenterazine or a known coelenterazine analogue such as furimazine when reacted on by a coelenterazine-utilizing enzyme.

Compounds of formula (I) can have a significantly lower background than corresponding mono-pro-coelenterazines when reacted on by a coelenterazine-utilizing enzyme. Background can be near to the instrument noise level and in certain embodiments does not change over 12-24 hours. The background can be measured by incubating a compound of formula (I) with a certain amount of coelenterazine-utilizing enzyme present in the sample well.

Compounds of formula (I) can have a signal to background ratio of 500 RLUs or greater, 1000 or greater, 5000 or greater, 10,000 or greater 15,000 or greater, 20,000 or greater, 50,000 or greater, 100,000 or greater, or 200,000 or greater, measured over a period of 1 minute, 5 minutes, 10 minutes, 20 minutes, 30 minutes, 40 minutes, 50 minutes, 1 hour, 1.5 hour, 2 hours, 3 hours, 4 hours, 5 hours, 10 hours, or 15 hours. The signal to background ratio can be assessed by taking the ratio of RLUs generated from a sample containing a pro-coelenterazine substrate, a coelenterazine-utilizing enzyme (e.g., NANOLUC® luciferase), and an enzyme of interest ("target enzyme") to the RLUs generated from a sample containing only the pro-coelenterazine substrate and coelenterazine-utilizing enzyme (no target enzyme).

Compounds of formula (I) can exhibit a stability of 30 minutes to 24 hours or beyond.

"Biocompatibility" refers to the tolerance of a cell (e.g., prokaryotic or eukaryotic) to a coelenterazine analogue (e.g., compounds of formula (I)). Biocompatibility of a coelenterazine analogue is related to the stress it causes on the host cell.

Enhanced biocompatibility of the compounds of formula (I) may be determined by measuring cell viability and/or growth rate of cells. For example, enhanced biocompatibility of the coelenterazine analogues may be determined by measuring cell viability in the absence of luciferase expression of cells exposed to the coelenterazine analogues compared to native or known coelenterazines to determine how compatible and/or toxic the coelenterazine analogues are to the cells.

In particular, enhanced biocompatibility may be determined using cell viability analysis (e.g., using the CELL-TITER-GLO® Luminescent Cell Viability assay), an apoptosis assay (e.g., using the CASPASE-GLO® technology), or another method known in the art. The effect of the disclosed compounds on cell viability or apoptosis may be compared to the effect of native or known coelenterazine analogues on cell viability or apoptosis.

Enhanced biocompatibility may also be determined by measuring the effect of the compounds of formula (I) on cell growth or gene expression. For example, enhanced biocompatibility of the compounds of formula (I) may be determined by measuring the cell number after a period of time or by determining the expression of stress response genes in a sample of cells that are exposed to compounds of formula (I) compared to cells exposed to a native or known coelenterazine or no coelenterazine. The effect of the disclosed compounds on cell growth or gene expression may be compared to a native or known coelenterazine.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. Synthesis Methods

Compounds of formula (I) can be synthesized as shown in Schemes 1-6.

Abbreviations which have been used in the descriptions of the Schemes that follow are: $Ag_2O$ for silver oxide; ACN for acetonitrile; $NaBH_4$ for sodium borohydride; MeOH for methanol; $CBr_4$ for carbon tetrabromide; $Ph_3P$ for triphenylphosphine; NaOMe for sodium methoxide; DCM for dichloromethane; $K_2CO_3$ for potassium carbonate; $Pd(Ph_3)_4$ for tetrakis(triphenylphosphine)palladium(0); DMF for dimethylformamide; and DBU for 1,8-diazabicyclo[5.4.0]undec-7-ene.

Scheme 1. Synthesis of β-D-glucose benzyl furimazine (WZ-0246)

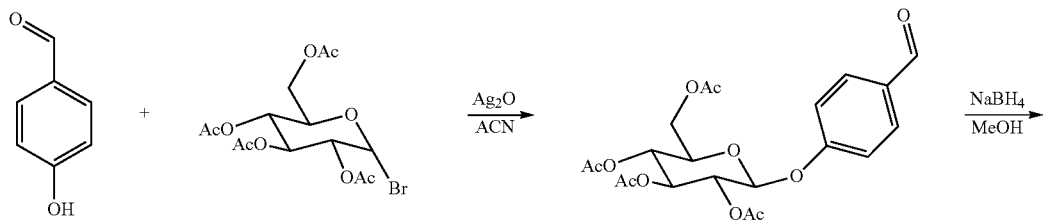

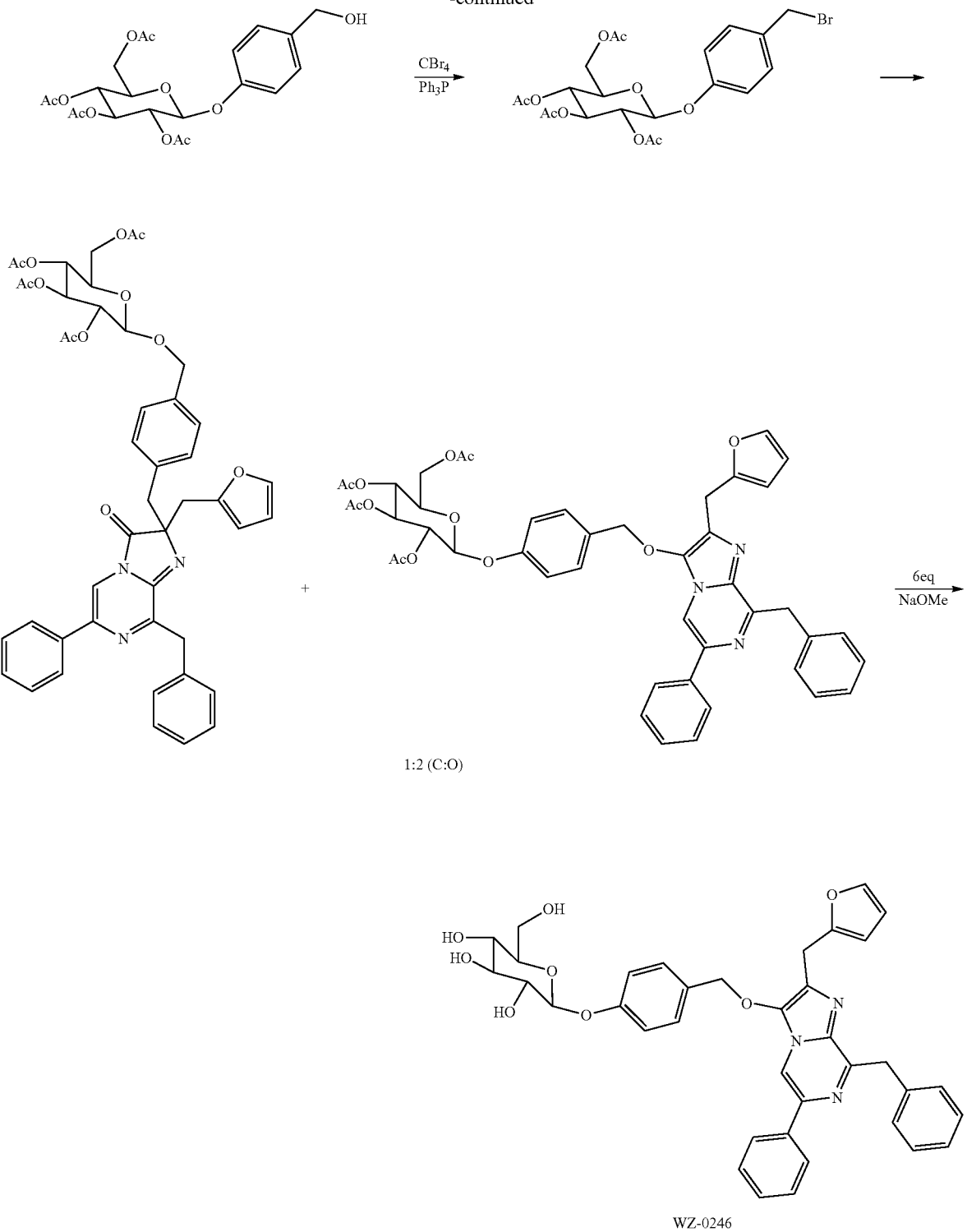

As shown in Scheme 1, p-phenol benzaldehyde was coupled with acetobromo-α-D-glucose in the presence of Ag₂O to generate p-aceto-β-D-glucose benzaldehyde in a yield of 85%. p-Aceto-β-D-glucose benzaldehyde was reduced by NaBH₄ to generate the corresponding p-aceto-β-D-glucose benzyl alcohol in a yield of 88%. The benzyl alcohol was converted to aceto-β-D-glucose benzyl bromide by reacting with CBr₄ and PPh₃. Furimazine (Promega Corporation) was then alkylated with aceto-β-D-glucose benzyl bromide under nitrogen and basic conditions to generate the desired O-alkylated product aceto-β-D-glucose benzyl furimazine in a yield of 57%. Aceto-β-D-glucose benzyl furimazine was further deprotected with NaOMe in DCM and MeOH to give the final mono-β-D-glucose benzyl furimazine (WZ-0246).

Scheme 2. Synthesis of bis-(β-D-glucose) benzyl furimazine (WZ-0262)
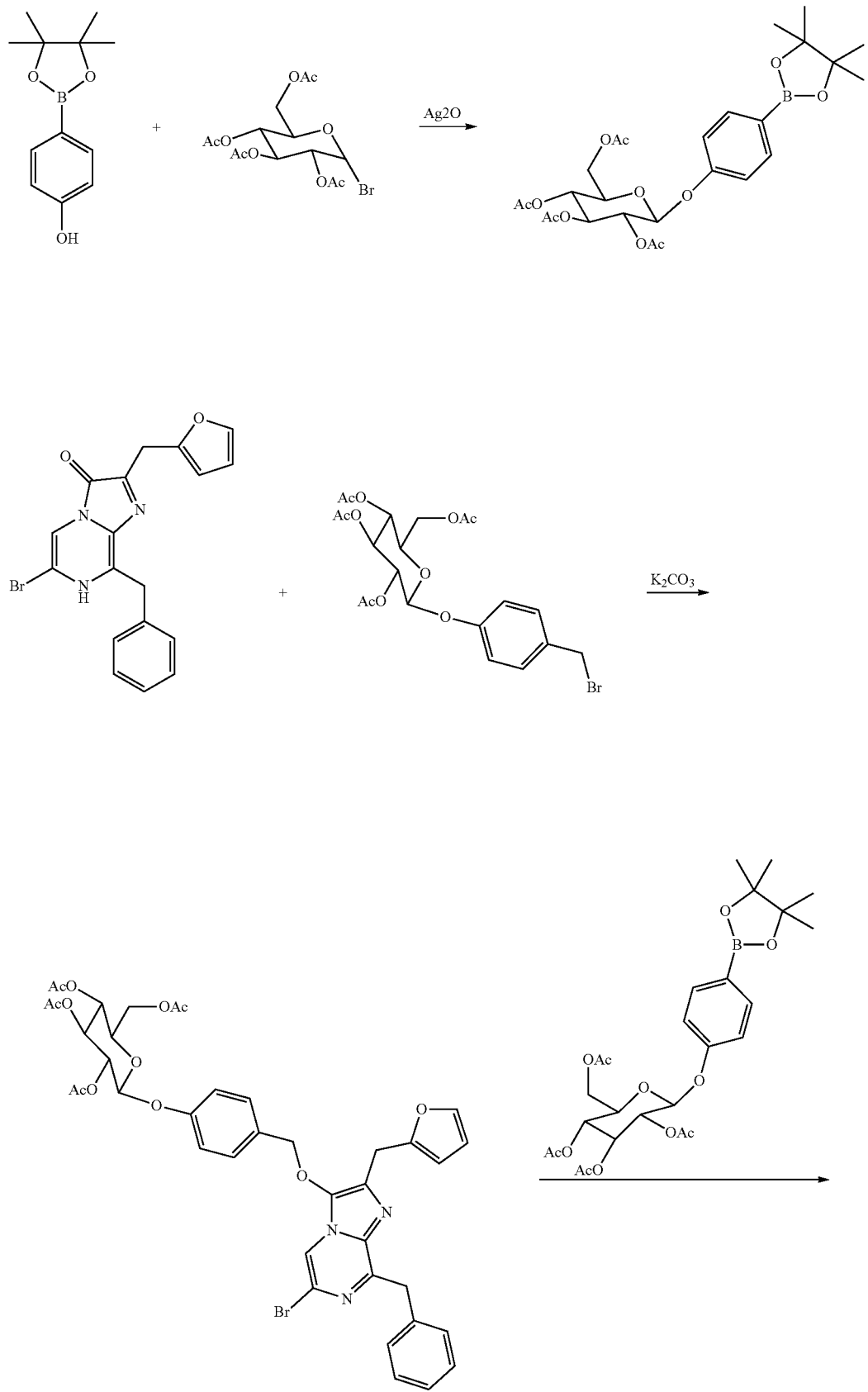

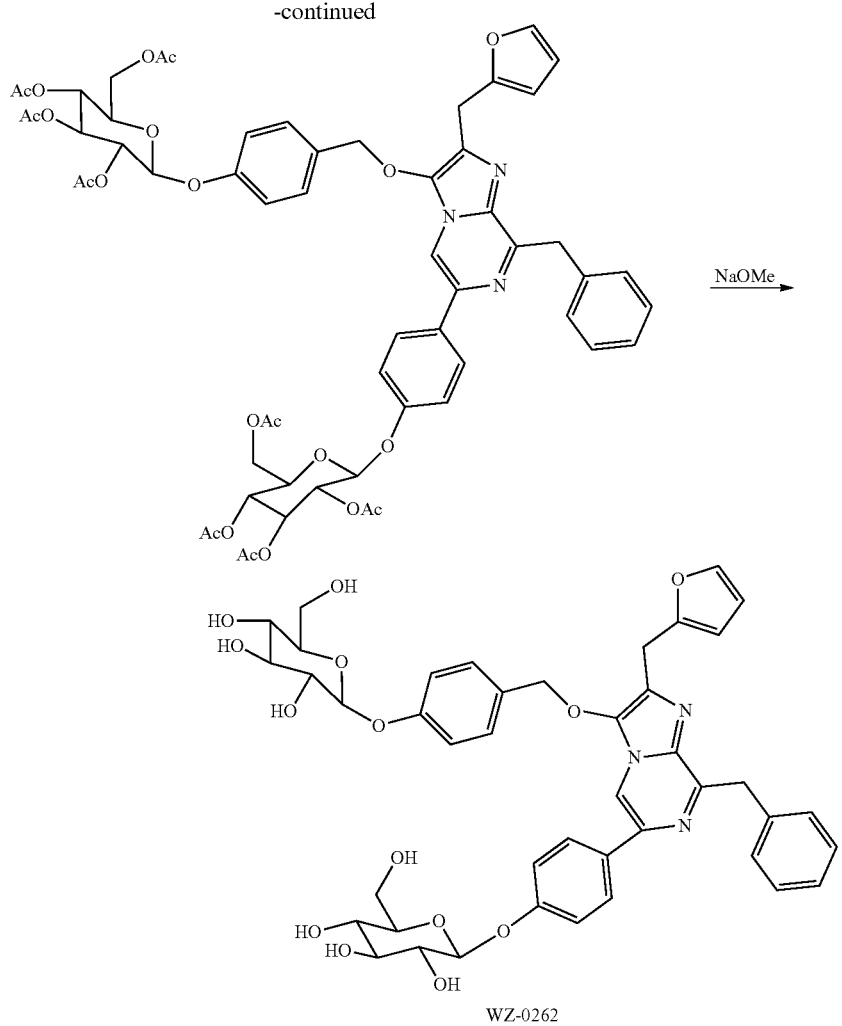

WZ-0262

Scheme 2 illustrates the synthesis of bis-β-D-glucose) benzyl furimazine (WZ-0262). 4-hydroxyl benzene pinacol-borate benzaldehyde was coupled with acetobromo-α-D-glucose in the presence of Ag₂O to generate p-aceto-β-D-glucose benzene pinacol borate in a yield of 40%. Bromo-furimazine was alkylated with aceto-β-D-glucose benzyl bromide under nitrogen and basic conditions to generate the desired O-alkylated product aceto-β-D-glucose benzyl bromo-furimazine in a yield of 75%. Aceto-β-D-glucose benzyl bromo-furimazine was coupled with p-aceto-β-D-glucose benzene pinacol borate by Suzuki reaction to generate bis (aceto-β-D-glucose) furimazine in a yield of 55%. Bis-(aceto-β-D-glucose)-furimazine was deprotected with NaOMe in DCM and MeOH to give the final bis-β-D-glucose) benzyl furimazine (WZ-0262).

Scheme 3. Synthesis of furimazine benzyl phosphate (WZ-0263)

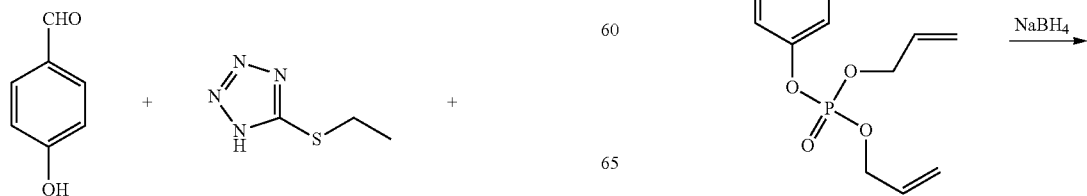

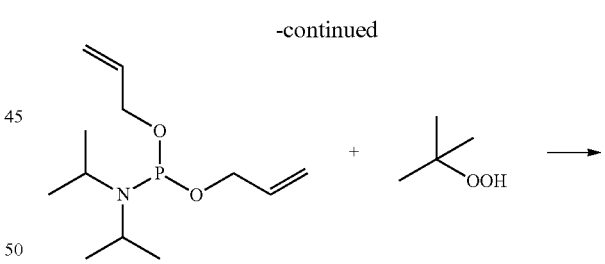

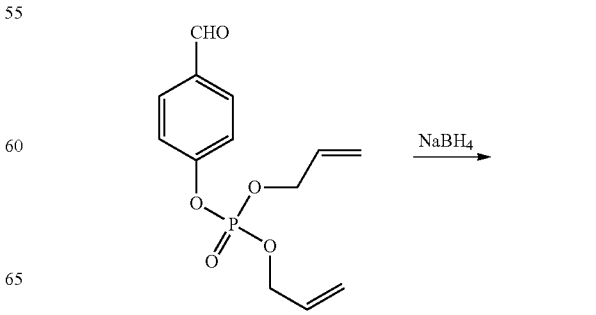

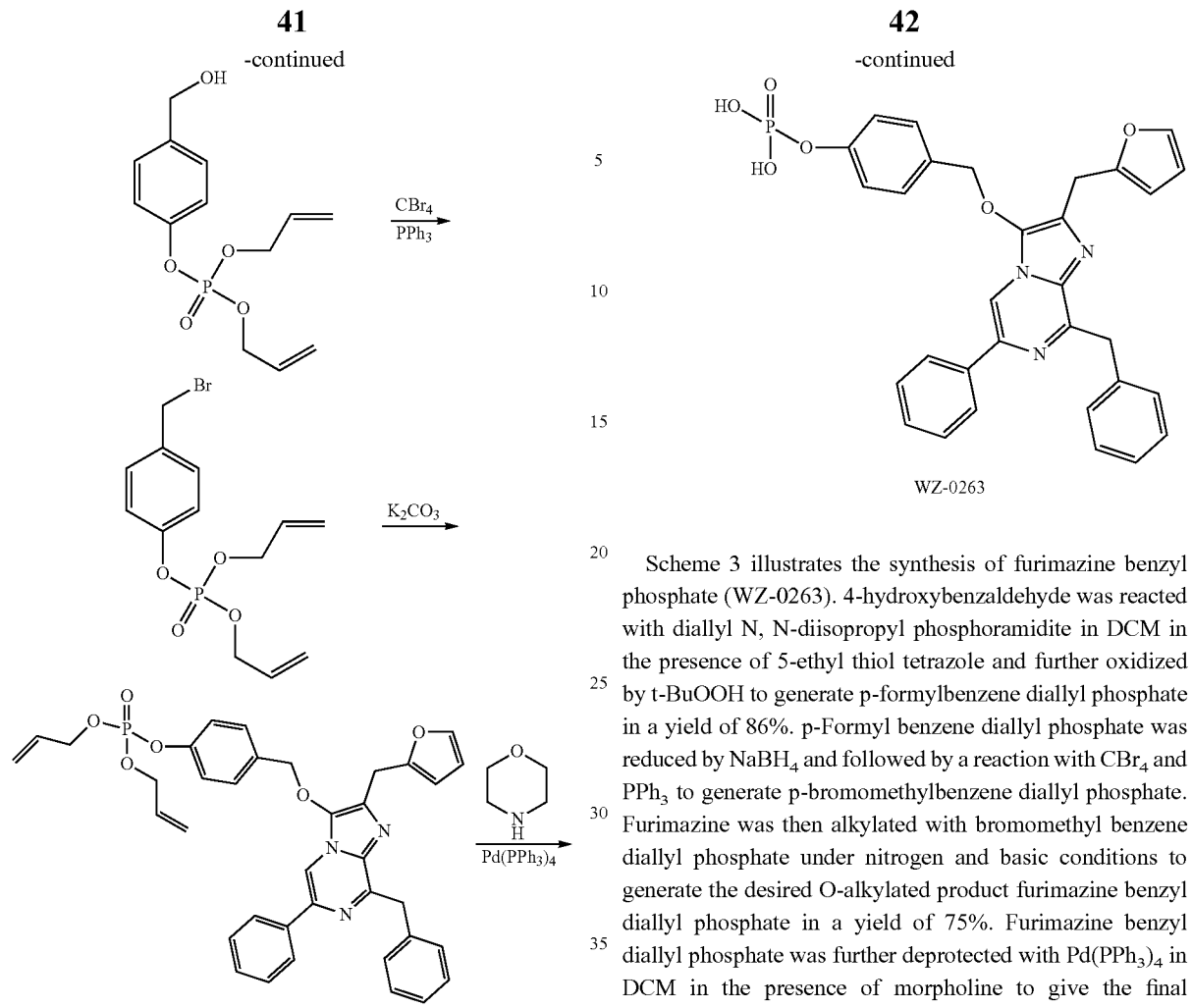

Scheme 3 illustrates the synthesis of furimazine benzyl phosphate (WZ-0263). 4-hydroxybenzaldehyde was reacted with diallyl N, N-diisopropyl phosphoramidite in DCM in the presence of 5-ethyl thiol tetrazole and further oxidized by t-BuOOH to generate p-formylbenzene diallyl phosphate in a yield of 86%. p-Formyl benzene diallyl phosphate was reduced by $NaBH_4$ and followed by a reaction with $CBr_4$ and $PPh_3$ to generate p-bromomethylbenzene diallyl phosphate. Furimazine was then alkylated with bromomethyl benzene diallyl phosphate under nitrogen and basic conditions to generate the desired O-alkylated product furimazine benzyl diallyl phosphate in a yield of 75%. Furimazine benzyl diallyl phosphate was further deprotected with $Pd(PPh_3)_4$ in DCM in the presence of morpholine to give the final mono-furimazine benzyl phosphate (WZ-0263).

Scheme 4. Synthesis of furimazine bis-phosphate (WZ-0291)

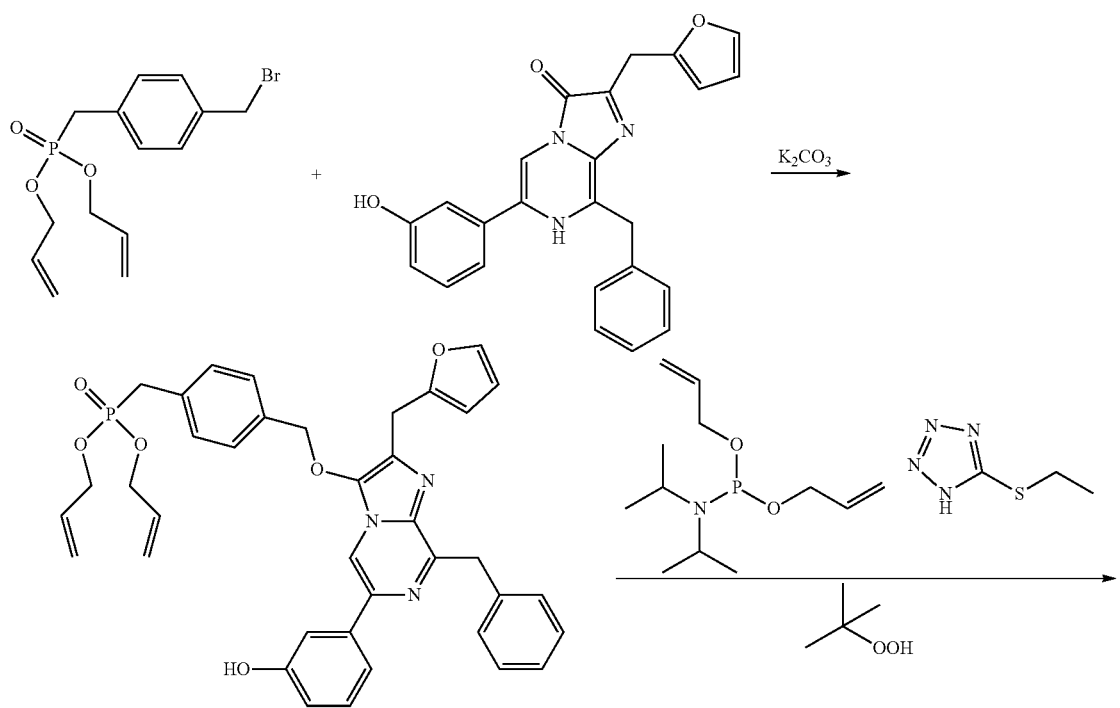

-continued

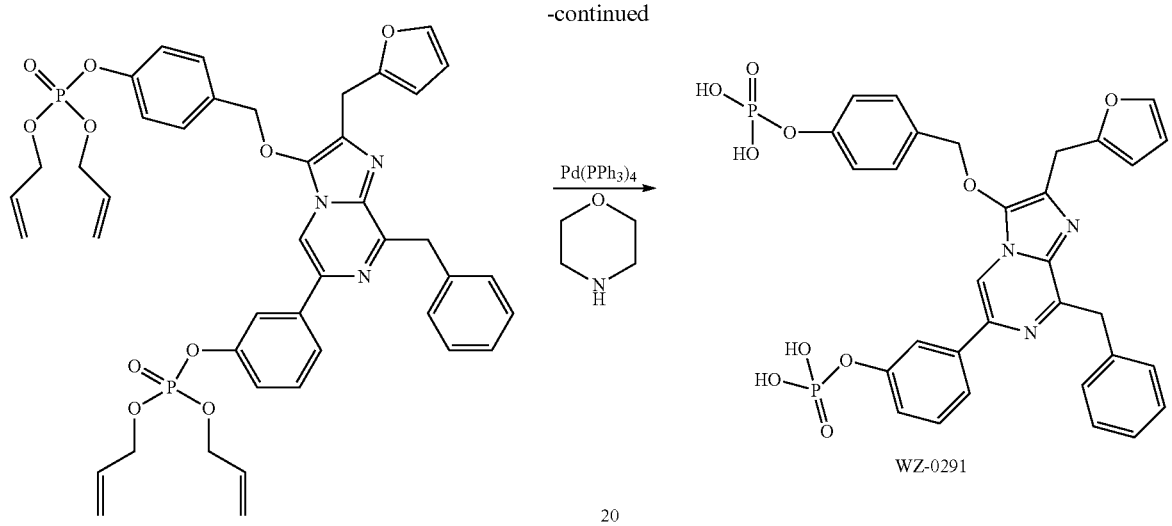

WZ-0291

Scheme 4 illustrates the synthesis of furimazine bis-phosphate (WZ-0291). 3-Hydroxyl furimazine was alkylated with bromomethyl benzene diallyl phosphate under nitrogen and basic conditions to generate the desired O-alkylated product 3-hydroxyl furimazine benzyl diallyl phosphate in a yield of 44%. 3-hydroxyl furimazine benzyl diallyl phosphate was reacted with diallyl N, N-diisopropyl phosphoramidite in DCM in the presence of 5-ethyl thiol tetrazole and further oxidized by t-BuOOH to generate furimazine bis-diallyl phosphate. Furimazine bis-diallyl phosphate was further deprotected with Pd(PPh$_3$)$_4$ in DCM in the presence of morpholine under nitrogen to give the final furimazine bis-phosphate (WZ-0291).

Scheme 5. Synthesis of Gly-Phe-aminobenzyl furimazine (WZ-2094)

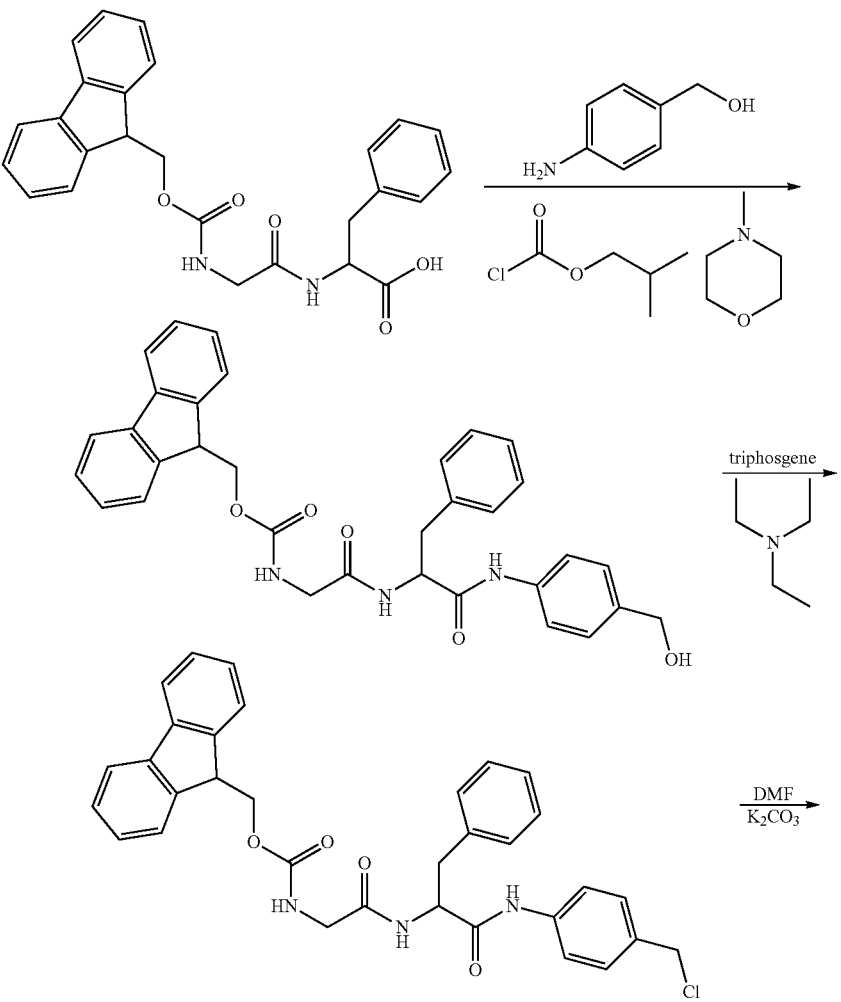

-continued

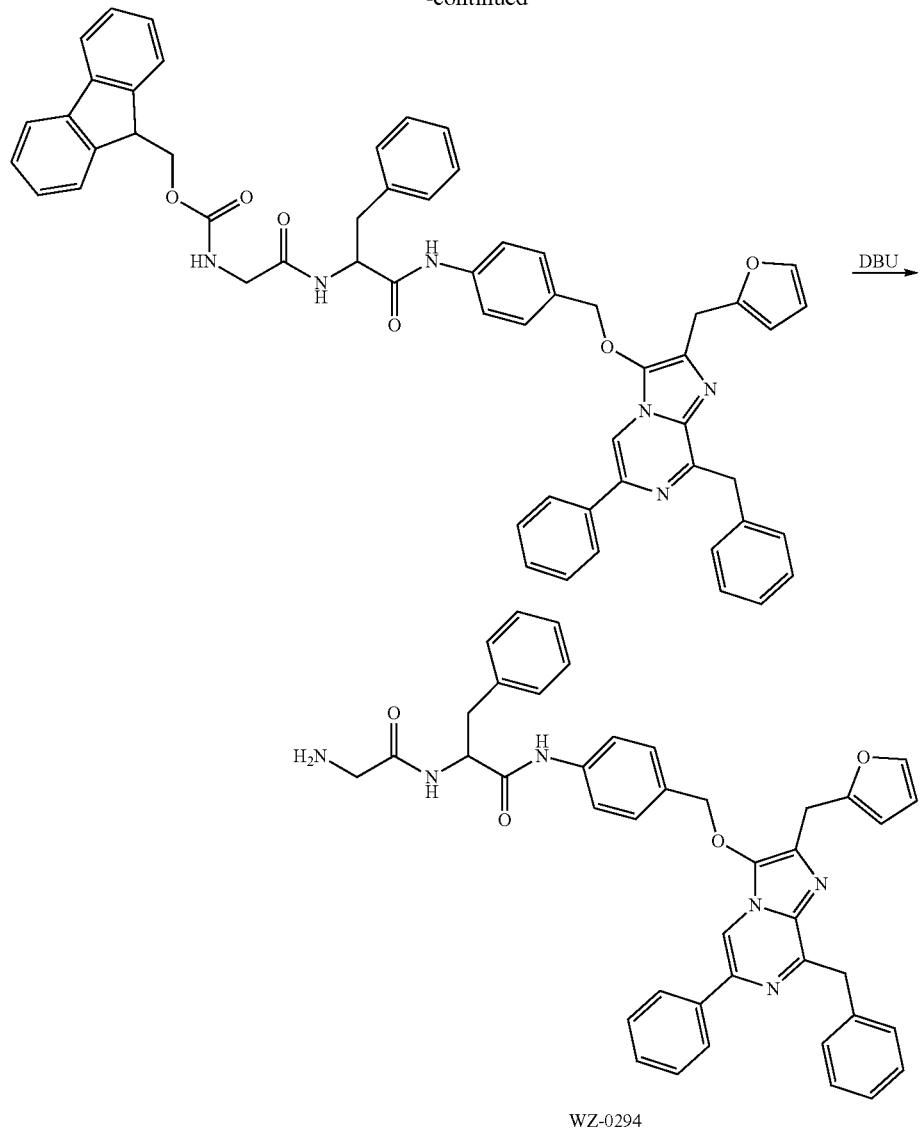

WZ-0294

Scheme 5 illustrates the synthesis of Gly-Phe-aminobenzyl furimazine (WZ-0294). Fmoc-Gly-Phe-COOH was activated with isobutyl chloroformate in the presence of N-methyl morpholine in dry THF and then reacted with 4-aminobenzyl alcohol to generate Fmoc-Gly-Phe-aminobenzyl alcohol in a yield of 59%. Fmoc-Gly-Phe-aminobenzyl alcohol was converted to Gly-Phe-aminobenzyl chloride with triphosgene. Furimazine was alkylated with Gly-Phe-aminobenzyl chloride under nitrogen and basic conditions to generate the desired O-alkylated product Fmoc-Gly-Phe-aminobenzyl furimazine. Fmoc was removed under standard DBU conditions to give the final Gly-Phe-aminobenzyl furimazine (WZ-0294).

Scheme 6. Synthesis of bis-Gly-Phe-aminobenzyl furimazine (WZ-0299)

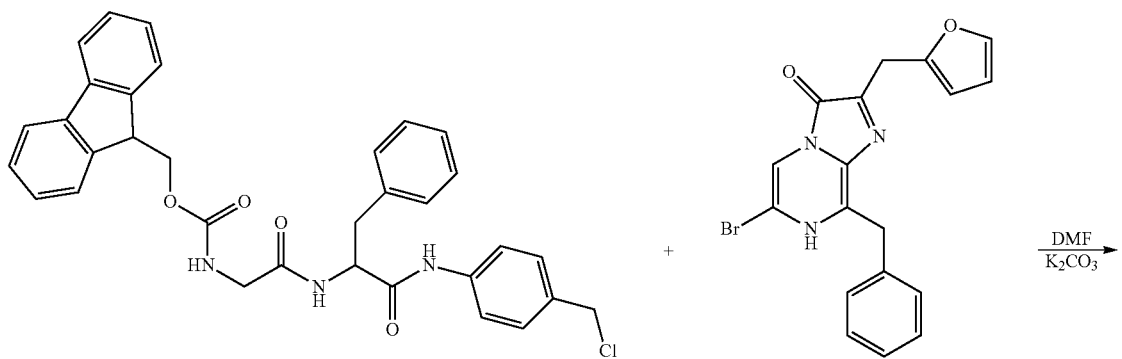

-continued
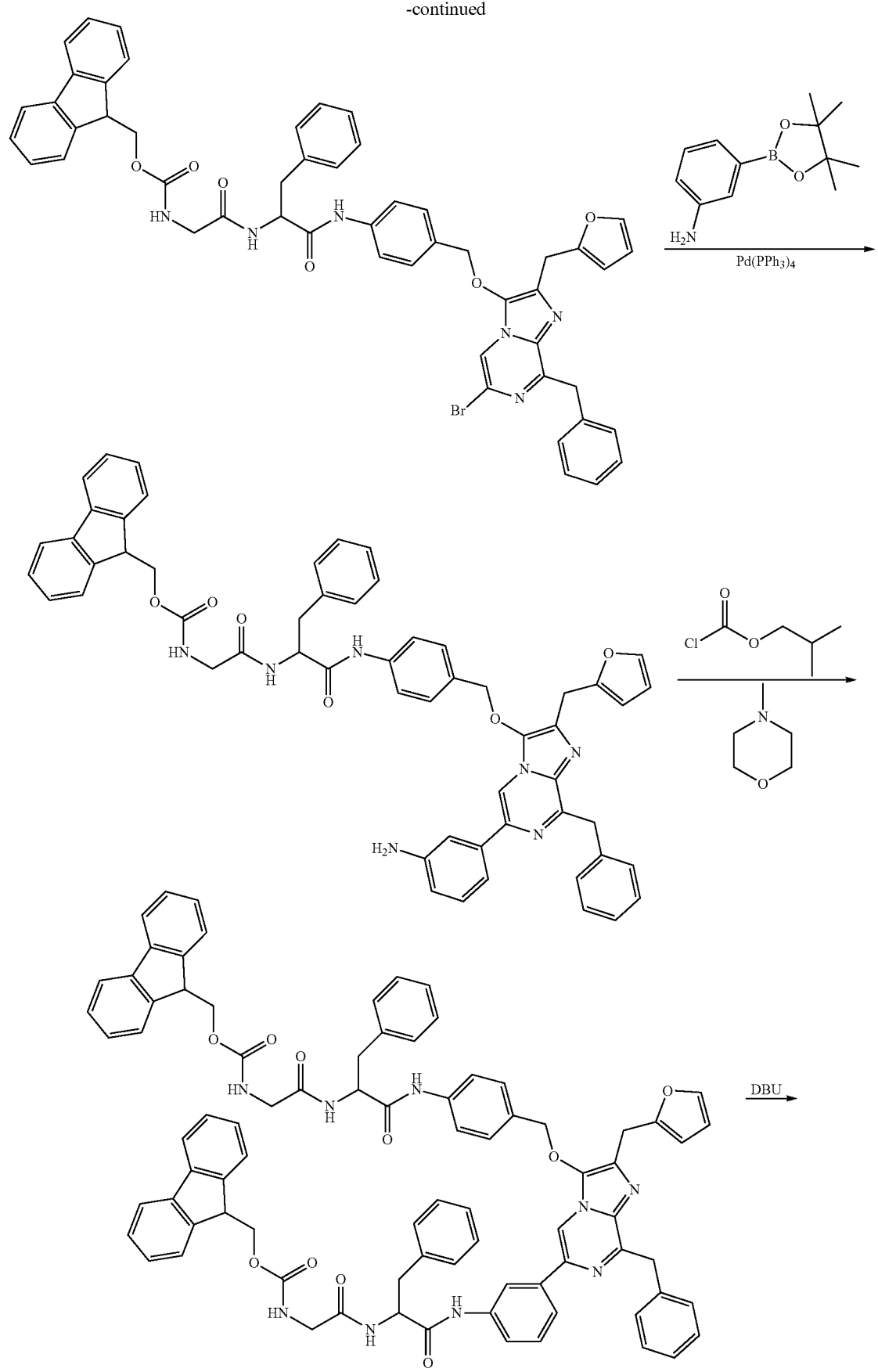

-continued

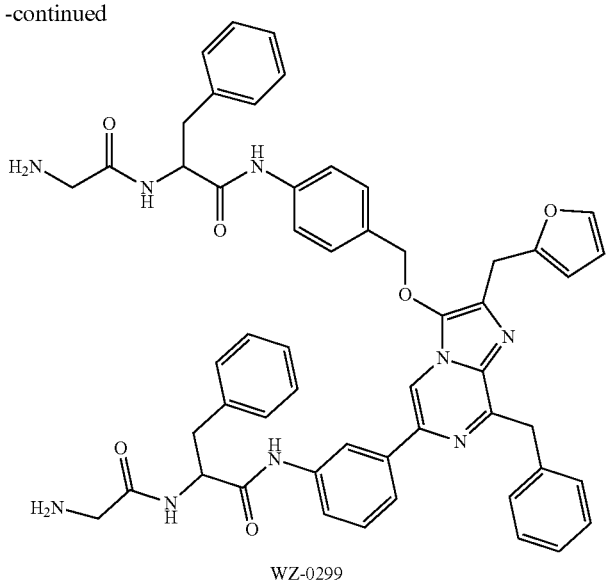

WZ-0299

Scheme 6 illustrates the synthesis of bis-Gly-Phe-aminobenzyl furimazine (WZ-0299). Bromo-furimazine was alkylated with Gly-Phe-aminobenzyl chloride under nitrogen and basic conditions to generate the desired O-alkylated product Fmoc-Gly-Phe-aminobenzyl bromo-furimazine. Fmoc-Gly-Phe-aminobenzyl bromo-furimazine was then coupled to 3-aminobenzene pinacol borate by Suzuki reaction to generate bis-Fmoc-Gly-Phe-aminobenzyl furimazine. Fmoc was removed under standard DBU conditions to give the final bis-Gly-Phe-aminobenzyl furimazine (WZ-0299).

Optimum reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. Methods of Use and Kits

The compounds of the disclosure may be used in any way that luciferase substrates, e.g., coelenterazine analogues, have been used. For example, they may be used in a bioluminogenic method that employs an analogue of coelenterazine to detect one or more molecules, e.g., an enzyme, a cofactor for an enzymatic reaction, an enzyme substrate, an enzyme inhibitor, an enzyme activator, or OH radicals, or one or more conditions, e.g., redox conditions, in a sample. The sample may include an animal (e.g., a vertebrate), a plant, a fungus, physiological fluid (e.g., blood, plasma, urine, mucous secretions), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels).

In certain embodiments, the compounds of formula (I) may be used to quantify molecules of interest. In some embodiments, compounds of formula (I) can be used as probes of a specific biochemical activity, e.g., apoptosis or drug metabolism. In some embodiments, the compounds of formula (I) can be coupled to a specific enzyme activity, wherein the compound can be acted on by the specific enzyme of interest. In some embodiments, the compounds of formula (I) cannot support luminescence directly when combined with a luciferase, but can be converted into a coelenterazine analogue through catalytic processing by a specific enzyme of interest. In some embodiments, the approach can be used for enzymes such as those used in drug metabolism, e.g., cytochrome P450 enzymes, monoamine oxidase, and glutathione S-transferase; and apoptosis, e.g., caspases. In some embodiments, the pro-coelenterazine analogue can be combined with other components necessary to support luminescence, e.g., a luminescent protein such as a luciferase, to provide a single reagent and a homogeneous assay. For example, when the reagent is added to a sample, luminescence is generated as the pro-coelenterazine analogue is converted to a coelenterazine analogue. In various embodiments, similar assays can be developed for other enzymes, small molecules, or other cellular processes that can be linked to the generation of coelenterazine analogues from pro-coelenterazine analogues.

In certain embodiments, the compounds of formula (I) can be used for detecting luminescence in live cells, e.g., in vivo. In some embodiments, a luciferase can be expressed in cells (as a reporter or otherwise), and the cells treated with a coelenterazine analogue (e.g., a compound of formula (I)), which will permeate cells in culture, react with the luciferase and generate luminescence. In addition to being cell permeant, the compounds of formula (I) show comparable biocompatibility to native coelenterazine in terms of cell viability. In some embodiments, the compounds of formula (I) containing chemical modifications known to increase the stability of native coelenterazine in media can be synthesized and used for more robust, live cell luciferase-based reporter assays. In still other embodiments, a sample (including cells, tissues, animals, etc.) containing a luciferase and a compound of formula (I) may be assayed using various microscopy and imaging techniques, e.g., in vivo imaging. In still other embodiments, a secretable luciferase is expressed in cells as part of a live-cell reporter system.

In certain embodiments, the compounds of formula (I) disclosed herein may be provided as part of a kit. In some embodiments, the kit may include one or more luciferases (in the form of a polypeptide, a polynucleotide, or both) and a coelenterazine analogue of formula (I), along with suitable reagents and instructions to enable a user to perform assays such as those disclosed herein. The kit may also include one or more buffers such as those disclosed herein.

4. Examples

Example 1. Synthesis of β-D-glucose Benzyl Furimazine (WZ-0246)

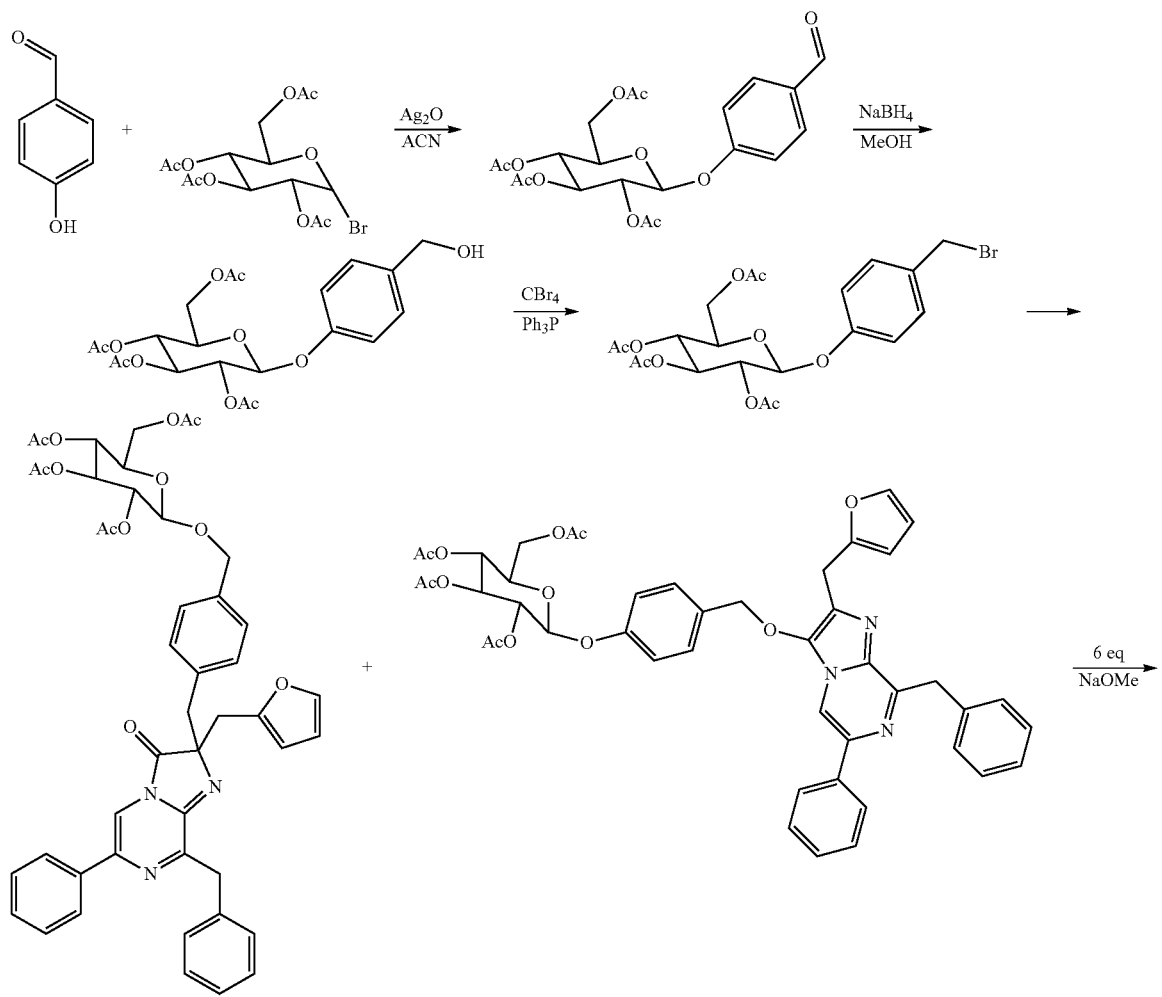

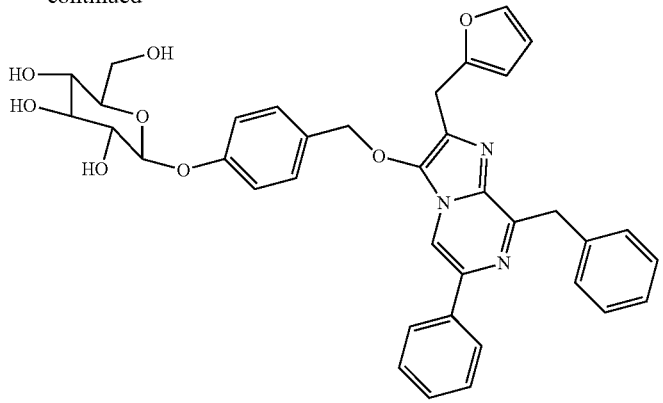

WZ-0246

Synthesis of aceto-β-D-glucose Benzaldehyde.

Hydroxybenzaldehyde (2.0 g, 16.38 mmol), acetobromo-α-D-glucose (6.73 g, 16.38 mmol), and Ag$_2$O (7.59 g, 32.75 mmol) were suspended in 50 ml dry acetonitrile under N$_2$. The mixture was stirred overnight at RT. After filtration, the solid was washed with THF. The solvent of filtrate was removed, and the compound was purified by silica flash chromatography using heptane/ethyl acetate as solvent to yield 6.3 g of desired product. (MS (m/e) [M+H] (C$_{36}$H$_{42}$N$_5$O$_9$S) calculated 720.8, observed 720.5. $^1$H NMR (300 MHz, CD$_2$Cl$_2$): 9.97 (s, 1H, CHO), 7.88 δ (d, 2H), 7.16 (d, 2H), 5.1-5.5 (m, 5H), 4.1-4.4 (m, 2H), 3.75-3.90 (m, 1H), 1.99-2.05 (m, 12H).

Synthesis of aceto-β-D-glucose Benzyl Alcohol.

NaBH$_4$ (0.97 g, 25.55 mmol) was added portion-wise to a cooled solution of aceto-β-D-glucose benzaldehyde in 60 mL mixture solvent CH$_2$Cl$_2$ and iPrOH (v/v=3/1) at 0° C. The mixed solution was allowed to reach room temperature and stirred for 2 h. 100 ml of DCM was added, and the reaction was quenched by adding acetic acid (2 ml) and water. The organic layer was dried over Na$_2$SO$_4$. The compound was purified by silica flash chromatography using DCM/ethyl acetate as solvent to yield of 5.12 g of desired product. $^1$H NMR (300 MHz, CD$_2$Cl$_2$): 7.32 δ (d, 2H), 6.99 (d, 2H), 5.1-5.4 (m, 4H), 4.62 (s, 2H), 4.1-4.4 (m, 2H), 3.75-3.90 (m, 1H), 1.99-2.05 (m, 12H).

Synthesis of aceto-β-D-glucose Benzyl Bromide.

To the solution of aceto-β-D-glucose benzyl alcohol (1.65 g, 3.65 mmol) and CBr$_4$ (1.45 g, 4.38 mmol) in 30 ml of methylene chloride, TPP (1.15 g. 4.38 mmol) at 0° C. was added. The mixture was stirred for 30 min at RT. After removing the solvent, the compound was purified by silica flash chromatography using DCM/ethyl acetate as solvent to yield of 1.55 g of desired product.

Synthesis of aceto-β-D-glucose Benzyl Furimazine.

1 ml of dry DMF was purged with nitrogen for 30 minutes. To this solution, furimazine (0.10 g, 0.26 mmol), aceto-β-D-glucose benzyl bromide (0.14 g, 0.26 mmol), and K$_2$CO$_3$ (0.40 g, 0.29 mmol) were added. The resultant mixture was stirred under nitrogen for 30 minutes at RT. The solution was diluted with 20 ml of DCM and washed with water and brine. The organic layer was dried over Na$_2$SO$_4$. The compound was purified by silica flash chromatography using DCM/ethyl acetate as solvent to yield of 0.114 mg (57%) of desired product and 25% of undesired C-alkylated product. MS (m/e) [M+H] (C$_{45}$H$_{43}$N$_3$O$_{12}$) calculated 817.28, observed 818.54.

Synthesis of β-D-glucose Benzyl Furimazine (WZ-0246).

To the solution of aceto-β-D-glucose benzyl furimazine (114 mg, 0.14 mmol) in 2 ml DCM, NaOMe (25%, 199 ul) in 10 ml MeONa was added. The mixture was stirred for 30 minutes. When LC-MS indicated the reaction was completed, 200 μl of acetic acid was added to neutralize the pH. After removing most DCM, the compound in residual solution was purified by HPLC using methanol and 10 mM NH$_4$Ac as eluent to give the desired product in a yield of 91% (83 mg). MS (m/e) [M+H] (C$_{37}$H$_{35}$N$_3$O$_8$) calculated 649.24, observed 650.44.

Example 2. Synthesis of β-D-glucose Furimazine (WZ-0261)

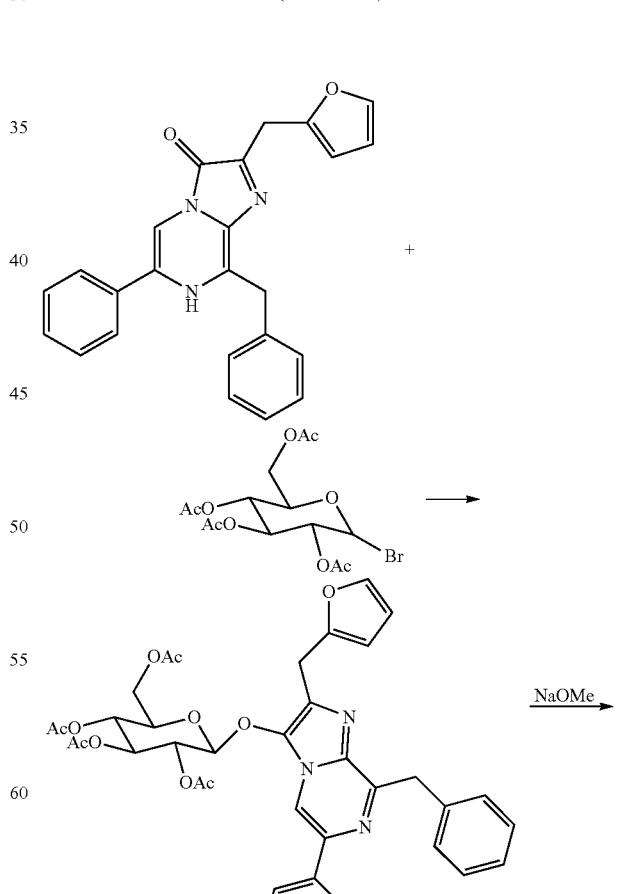

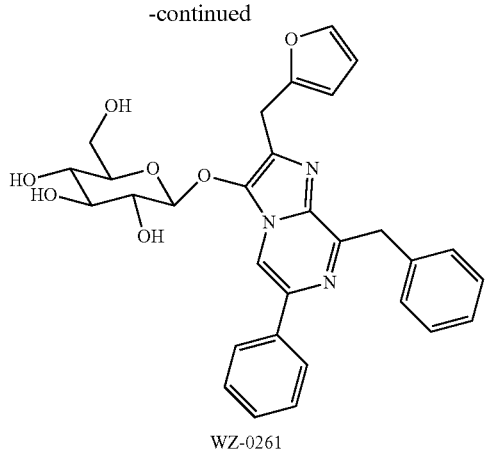

WZ-0261

Synthesis of aceto-β-D-glucose Furimazine.

5 ml of dry DMF was purged with nitrogen for 30 minutes. To this solution, furimazine (0.15 g, 0.39 mmol), aceto-α-D-glucose bromide (0.194 g, 0.47 mmol) and $K_2CO_3$ (0.65 g, 0.47 mmol) were added. The resultant mixture was stirred under nitrogen for 30 minutes at RT. The solution was diluted with 20 ml of DCM and washed with water and brine. The organic layer was dried over $Na_2SO_4$. The compound was purified by silica flash chromatography using DCM/ethyl acetate as solvent to yield 0.12 mg (43%) of desired product. MS (m/e) [M+H] ($C_{38}H_{37}N_3O_{11}$) calculated 711.24, observed 712.33.

Synthesis of β-D-glucose Furimazine (WZ-0261).

To the solution of aceto-β-D-glucose furimazine (100 mg, 0.14 mmol) in 2 ml DCM, NaOMe (25%, 99 ul) in 10 ml MeONa was added. The mixture was stirred for 30 minutes. When LC-MS indicated the reaction was completed, 100 μl of acetic acid was added to neutralize the pH. After removing most DCM, the compound in residual solution was purified by HPLC using methanol and 10 mM $NH_4Ac$ as eluent to give the desired product in a yield of 85% (65 mg). MS (m/e) [M+H] ($C_{30}H_{29}N_3O_7$) calculated 544.20, observed 545.18.

Example 3. Synthesis of bis-(β-D-glucose) Benzyl Furimazine (WZ-0262)

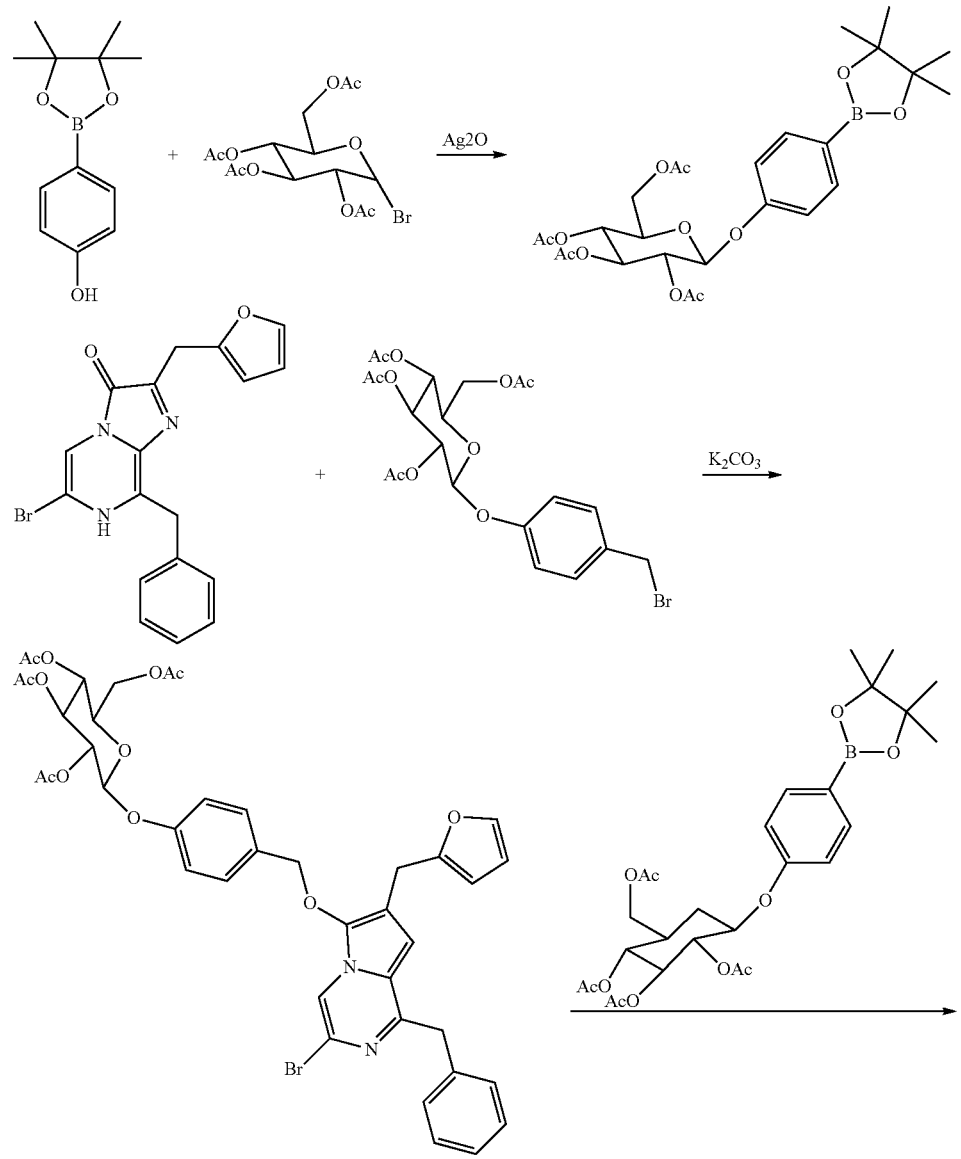

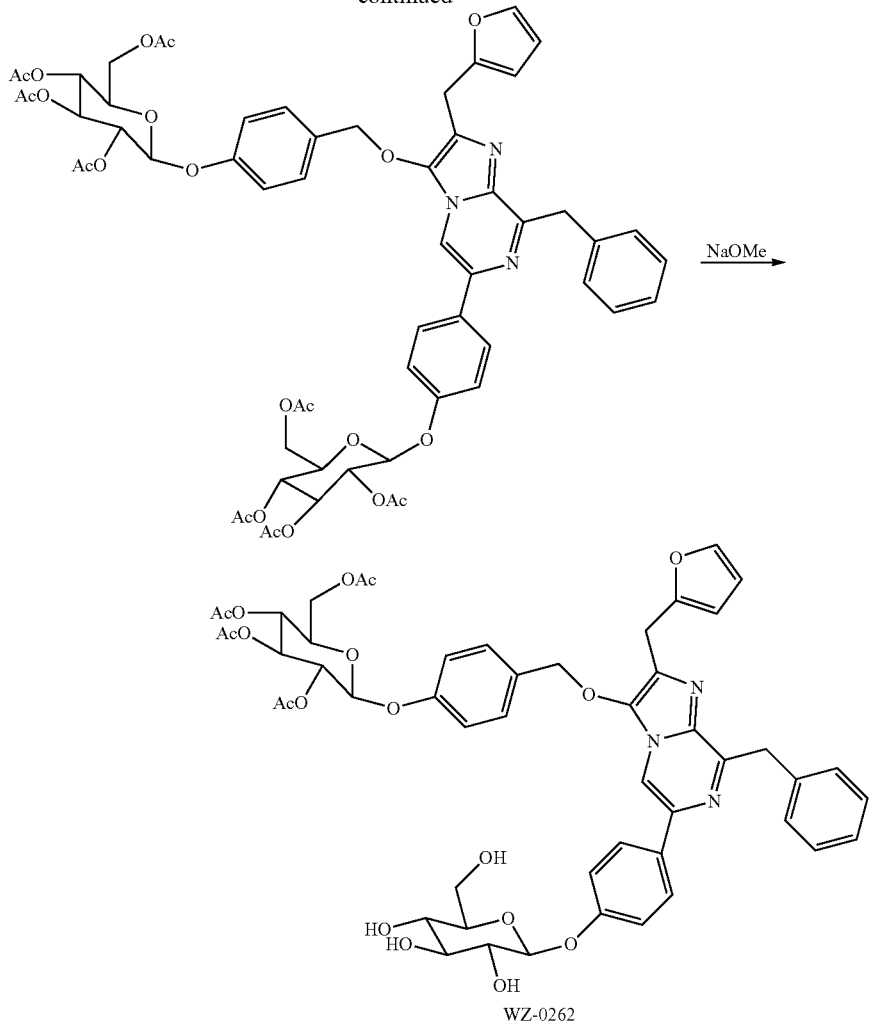

WZ-0262

Synthesis of p-aceto-β-D-glucose Benzene Pinacol Borate.

4-Hydroxyl pinacolborate (2.0 g, 9.09 mmol), aceto-bromo-α-D-glucose (2.53 g, 10.91 mmol), and Ag₂O (4.48 g, 32.75 mmol) were suspended in 50 ml of dry acetonitrile under N₂. The mixture was stirred overnight at RT. After filtration, the solid was washed with THF. The solvent of filtrate was removed, and the compound was purified by silica flash chromatography using heptane/ethyl acetate as solvent to give a yield of 40.0% (2.0 g) desired product. $^1$H NMR (300 MHz, CDCl₃): 7.76 δ (d, 2H), 6.98 (d, 2H), 5.22-5.38 (m, 2H), 5.05-5.20 (m, 2H), 4.1-4.3 (m, 2H), 3.81-3.97 (m, 1H), 1.99-2.05 (m, 12H), 1.33 (s, 12H).

Synthesis of aceto-β-D-glucose Benzyl Bromo-Furimazine.

5 ml of dry DMF was purged with nitrogen for 30 minutes. To this solution, bromo-furimazine (0.10 g, 0.26 mmol), aceto-β-D-glucose benzyl bromide (150 mg, 0.29 mmol), and K₂CO₃ (0.54 g, 0.39 mmol) were added. The resultant mixture was stirred under nitrogen for 30 minutes at RT. The solution was diluted with 20 ml of DCM and washed with water and brine. The organic layer was dried over Na₂SO₄. The compound was purified by silica flash chromatography using DCM/ethyl acetate as solvent to yield of 160 mg (75.0%) of desired product. MS (m/e) [M+H] ($C_{39}H_{38}1\backslash1_3O_{12}$) calculated 819.16, observed 820.25, 822.20 (1:1).

Synthesis of Bis (aceto-β-D-glucose) Benzyl Furimazine.

Aceto-β-D-glucose bromo-furimazine (70 mg) was dissolved in dioxane 5 ml and stirred under N₂ for 10 minutes. Pd(PPh₃)₄ (10 mg), p-aceto-β-D-glucose benzene pinacol borate (70.4 mg, 0.17 mmol), Cs₂CO₃ (55.6 mg, 0.17 mmol), and water 1 ml were added. The mixture was heated up to 80° C. for 30 minutes. TLC and LC-MS confirmed the reaction was completed. 20 ml of DCM was added, the aqueous layer removed, and the organic layer was washed by water and dried over Na₂SO₄. The compound was purified by silica flash chromatography using heptane/ethyl acetate as solvent to yield 55 mg (55%) of desired product. MS (m/e) [M+H] ($C_{59}H_{61}H_3O_{22}$) calculated 1163.37, observed 1164.75.

Synthesis of Bis (β-D-glucose) Benzyl Furimazine (WZ-0262).

Bis (aceto-β-D-glucose) benzyl furimazine (100 mg, 0.085 mmol) was dissolved in 2 ml DCM and NaOMe (25%, 100 ul) in 10 ml MeOH was added. The mixture was stirred for 30 minutes. When LC-MS indicated the reaction was completed, 100 μl of acetic acid was added to neutralize the pH. After removing most DCM, the compound in residual solution was purified by HPLC using methanol and 10 mM NH₄Ac as eluent to give the desired product in a yield of 84% (60 mg). MS (m/e) [M+H] ($C_{43}H_{45}N_3O_{14}$) calculated 827.29, observed 828.28.

Example 4. Synthesis of bis-(β-D-glucose) Furimazine (WZ-0307)
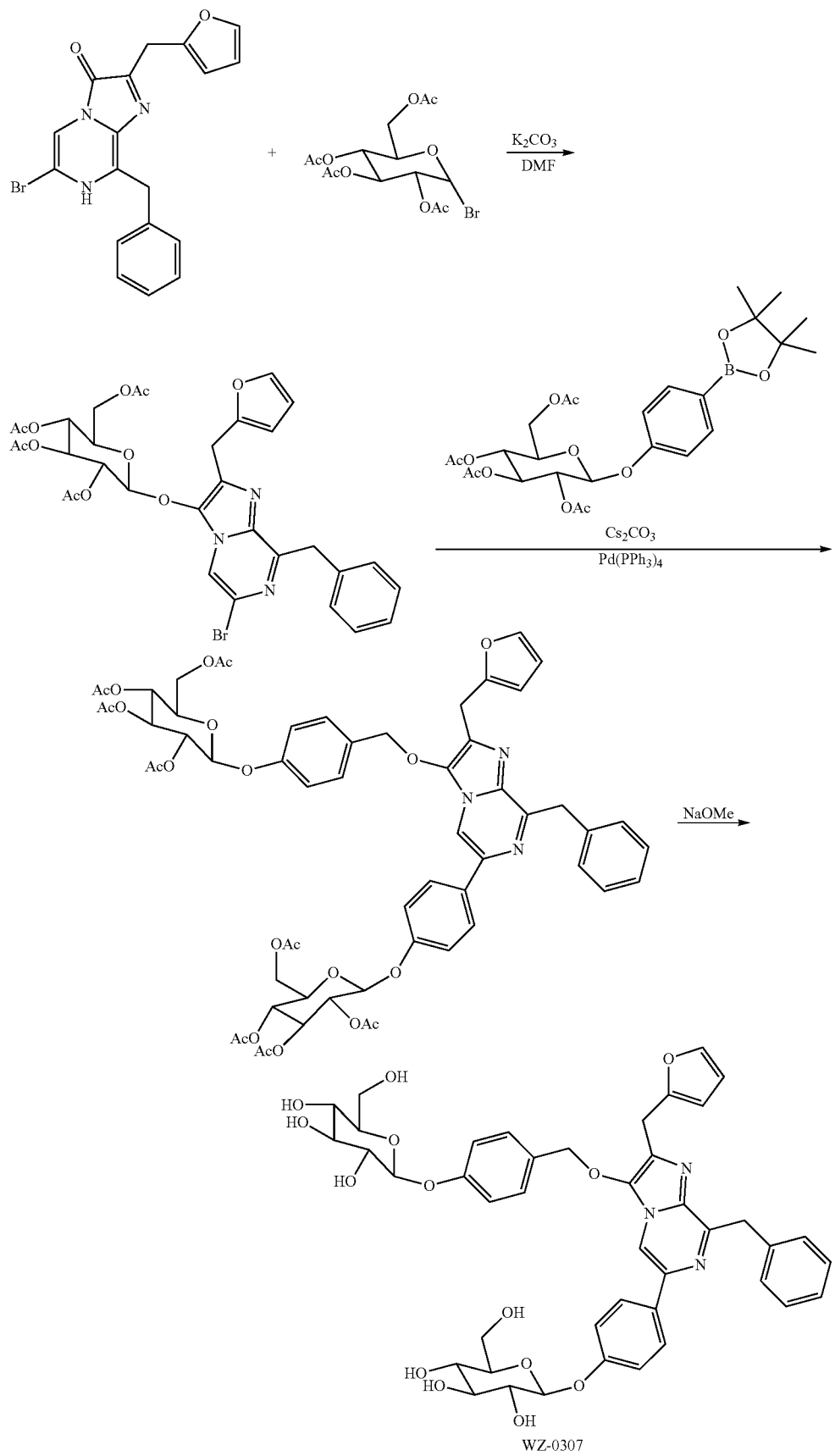

Synthesis of aceto-β-D-glucose Bromo-Furimazine.

5 ml of dry DMF was purged with nitrogen for 30 minutes. To this solution were added bromo-furimazine (100 mg, 0.26 mmol), aceto-β-D-glucose bromide (118 mg, 0.29 mmol) and $K_2CO_3$ (0.54 g, 0.39 mmol). The resultant mixture was stirred under nitrogen for 30 minutes at RT. The solution was diluted with 20 ml of DCM and washed with water and brine. The organic layer was dried over $Na_2SO_4$. The compound was purified by silica flash chromatography using DCM/ethyl acetate as solvent to yield 81 mg (75%) of desired product. MS (m/e) [M+H] ($C_{32}H_{32}BrN_3O_{11}$) calculated 713.12, observed 714.18, 716.13 (1:1).

Synthesis of Bis (aceto-β-D-glucose) Furimazine.

Aceto-β-D-glucose bromo-furimazine (50 mg) was dissolved in 5 ml of dioxane and stirred under $N_2$ for 10 minutes. $Pd(PPh_3)_4$ (10 mg), p-aceto-β-D-glucose benzene pinacol borate (77 mg, 0.14 mmol), $Cs_2CO_3$ (45.6 mg, 0.14 mmol), and water 1 ml were added. The mixture was heated up to 80° C. for 30 minutes. TLC and LC-MS confirmed the reaction was completed. 20 ml of DCM was added, the aqueous layer removed, and organic layer was washed by water and dried over $Na_2SO_4$. The compound was purified by silica flash chromatography using heptane/ethyl acetate as solvent to yield of 55 mg (74%) of desired product. MS (m/e) [M+H] ($C_{52}H_{55}N_3O_{21}$) calculated 1057.33, observed 1058.62.

Synthesis of Bis (β-D-glucose) Furimazine (WZ-0307).

Bis (aceto-β-D-glucose) furimazine (100.0 mg, 0.085 mmol) was dissolved in 2 ml DCM, and NaOMe (25%, 100 µl) in 10 ml MeOH was added. The mixture was stirred for 30 minutes. When LC-MS indicated the reaction was completed, 100 µl of acetic acid was added to neutralize the pH. After removing DCM, the compound in residual solution was purified by HPLC using methanol and 10 mM $NH_4Ac$ as eluent to give the desired product in a yield of 80% (25 mg). MS (m/e) [M+H] ($C_{36}H_{39}N_3O_{13}$) calculated 721.25, observed 722.35.

Example 5. Synthesis of Furimazine Phosphate (WZ-0265)

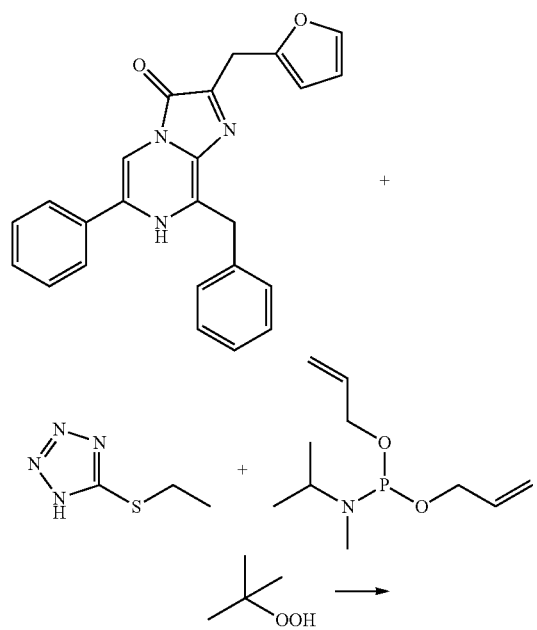

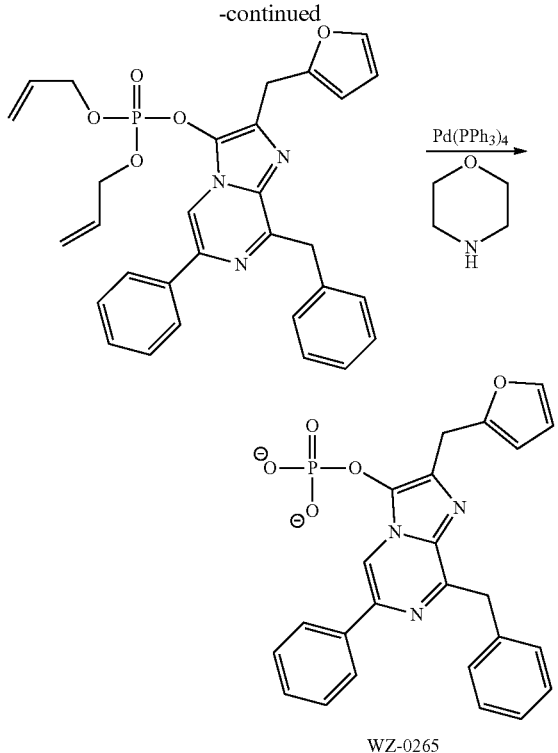

WZ-0265

Synthesis of Furimazine Diallyl Phosphate.

To the solution of furimazine (150 mg, 0.393 mmol) and diallyl N,N-diisopropyl phosphoramidite (106.1 mg, 0.432 mmom) in 10 ml DCM, 5-ethyl thiol tetrazole (51.2 mg, 0.393 mmol) was added. The mixture was stirred for 30 minutes. TLC indicated the reaction was completed. t-BuOOH was added, and the resultant mixture was stirred for another 10 minutes. The mixture was diluted with 30 ml of DCM and washed with $Na_2S_2O_3$ once and water twice. The organic layer was dried over $Na_2SO_4$. The compound was purified by silica flash chromatography using heptane/ethyl acetate as solvent to yield 75% (160 mg) of desired product.

Synthesis of Furimazine Phosphate (WZ-0265).

The mixture of furimazine diallyl phosphate (160 mg, 0.295 mmol), $Pd(PPh_3)_4$ (34.14 mg, 0.0295 mmol) and morpholine (128 mg, 1.48 mmol) in 10 ml of $CH_2Cl_2$ was stirred for 30 minutes. After removing the solvent, the compound was purified by HPLC using methanol and 10 mM $NH_4Ac$ as eluent to give the desired product in a yield of 73% (100 mg). MS (m/e) [M+H] ($C_{24}H_{20}N_3O_5P$) calculated 461.12, observed 462.02.

Example 6. Synthesis of Furimazine Benzyl Phosphate (WZ-0263)

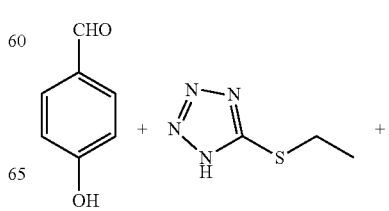

-continued

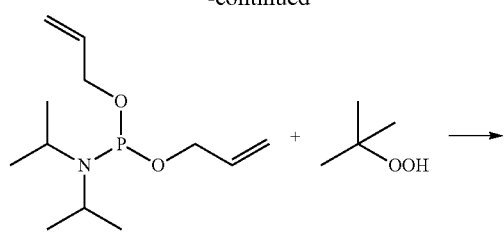
+
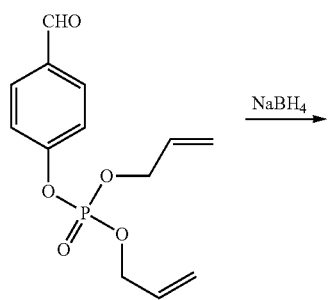

NaBH₄ →

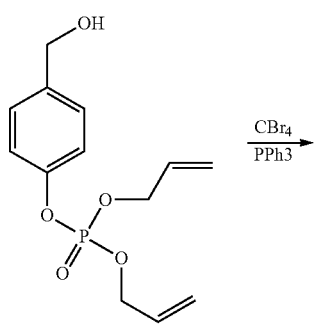

CBr₄ / PPh₃ →

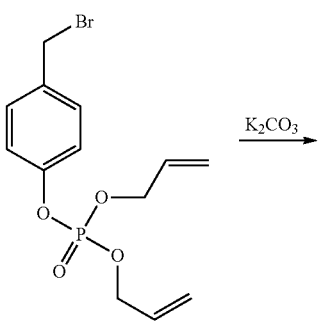

K₂CO₃ →

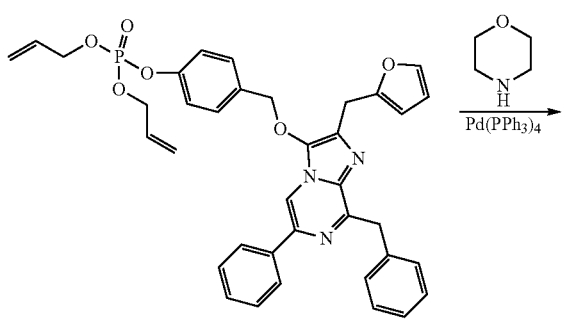

Pd(PPh₃)₄ →

-continued

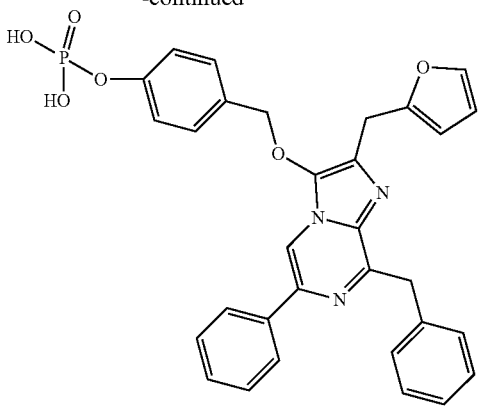

Synthesis of p-formylbenzene Diallyl Phosphate.

To the solution of 4-hydroxybenzaldehyde (500 mg, 4.09 mmol) and diallyl N,N-diisopropyl phosphoramidite (1.0 g, 4.09 mmol) in 30 ml DCM, 5-ethyl thiol tetrazole (0.27 mg, 2.05 mmol) was added. The mixture was stirred for 30 minutes. TLC indicated the reaction was completed. t-BuOOH (5.0 M, 2.46 ml) was added, and the resultant mixture was stirred for another 10 minutes. The mixture was diluted with 100 ml of DCM and washed with Na₂S₂O₃ once and water twice. The organic layer was dried over Na₂SO₄. The compound was purified by silica flash chromatography using heptane/ethyl acetate as solvent to yield 86% (994 mg) of desired product. ¹H NMR (300 MHz, CD₂Cl₂): 9.99 (s, 1H), 7.82 δ (d, 2H), 7.40 (d, 2H), 5.8-6.1 (m, 2H), 5.2-5.4 (m, 4H), 4.6-4.8 (m, 4H).

Synthesis of p-hydroxylmethylbenzene Diallyl Phosphate.

To the solution of p-formylbenzene diallyl phosphate (950 mg, 3.37 mmol) in 30 ml methanol, NaBH₄ (0.255 g, 6.73 mmol) was added. The resultant mixture was stirred for 30 minutes. The reaction was quenched with water and extracted three times with DCM. The organic layer was dried over Na₂SO₄. The compound was purified by silica flash chromatography using heptane/ethyl acetate as solvent to yield 76% (730 mg) of desired product. ¹H NMR (300 MHz, CD₂Cl₂): 7.38 δ (d, 2H), 7.19 (d, 2H), 5.83-6.06 (m, 2H), 5.2-5.35 (m, 4H), 4.5-4.7 (m, 6H).

Synthesis of p-bromomethylbenzene Diallyl Phosphate.

To the solution of p-hydroxylmethylbenzene diallyl phosphate (730 mg, 2.57 mmol) and CBr₄ (1.02 g, 3.08 mmol) in 30 ml of methylene chloride, TPP (0.81 g. 3.08 mmol) at 0° C. was added. The mixture was stirred for 30 min at RT. After removing the solvent, the compound was purified by silica flash chromatography using heptane/ethyl acetate as solvent to give a yield 81% (720 mg) of desired product. ¹H NMR (300 MHz, CD₂Cl₂): 7.38 δ (d, 2H), 7.19 (d, 2H), 5.83-6.06 (m, 2H), 5.20-5.45 (m, 4H), 4.6-4.7 (m, 4H), 4.51 (s, 2H).

Synthesis of Furimazine Benzyl Diallyl Phosphate.

5 ml of dry DMF was purged with nitrogen for 30 minutes. To this solution, furimazine (100 mg, 0.26 mmol), p-bromomethylbenzene diallyl phosphate (91 mg, 0.26 mmol) and K₂CO₃ (0.54 g, 0.39 mmol) were added. The resultant mixture was stirred under nitrogen for 30 minutes at RT. The solution was diluted with 20 ml of DCM and washed with water and brine. The organic layer was dried over Na₂SO₄. The compound was purified by silica flash chromatography using DCM/ethyl acetate as solvent to yield 81 mg (75%) of desired product. MS (m/e) [M+H] ($C_{37}H_{34}N_3O_6P$) calculated 647.22, observed 648.25.

Synthesis of Furimazine Phosphate (WZ-0263).

The mixture of furimazine benzyl diallyl phosphate (120 mg, 0.185 mmol), Pd(PPh₃)₄ (43 mg, 0.037 mmol), and morpholine (161 mg, 1.85 mmol) in 10 ml of CH₂Cl₂ was stirred for 30 minutes. After removing the solvent, the compound was purified by HPLC using methanol, and 10 mM NH₄Ac as eluent to give the desired product in a yield of 78% (82 mg). MS (m/e) [M+H] ($C_{31}H_{26}N_3O_6P$) calculated 567.16, observed 568.1.

Example 7. Synthesis of Furimazine Methyl Phosphate (WZ-0314)

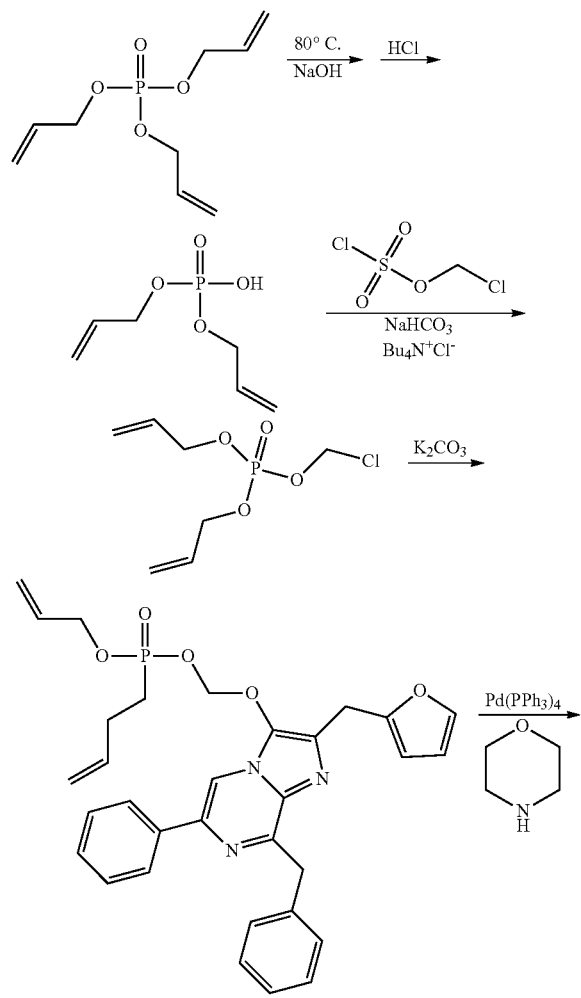

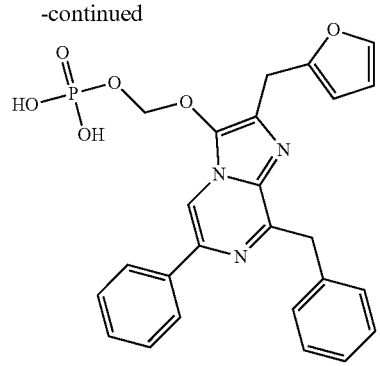

WZ-0314

Synthesis of Diallyl Phosphate.

The solution of triallyl phosphate (10.0 g, 45.83 mmol) in 50 ml of 30% NaOH was heated to reflux for 30 minutes. The mixture was cooled to RT and neutralized with 30 ml of conc. HCl. The mixture was extracted three times with ether (3×50 ml). The organic layer was dried over Na₂SO₄. After removing the solvent, the compound was dried under vacuum to give a yield of 15% (1.20 g), and the compound was directly used in next step without further purification.

Synthesis of Chloromethylene Diallyl Phosphate.

Diallyl phosphate, sodium bicarbonate, and tetra-n-butylammonium hydrogen sulfate were dissolved in 40 ml of water. 25 ml of dichloromethane was added, and the mixture was vigorously stirred at 0° C. for 10 min, followed by the addition of chloromethyl chlorosulfate (0.67 g, 4.06 mmol) in DCM (15 ml) with continuous vigorous stirring overnight at room temperature. The organic layer was washed with brine and dried with Na₂SO₄. After removing the solvent, the compound was directly used in next step without further purification.

Synthesis of Furimazine Methylene Diallyl Phosphate.

Chloromethylene diallyl phosphate (114 mg, 1.05 mmol) and KI (0.13 g, 0.79 mmol) in 5 ml of dry DMF was stirred under nitrogen for 30 minutes. To this solution, furimazine (100 mg, 0.26 mmol) and K₂CO₃ (109 mg, 0.79 mmol) were added. The resultant mixture was stirred under nitrogen for 30 minutes at RT. The solution was diluted with 20 ml of DCM and washed with water and brine. The organic layer was dried over Na₂SO₄. The compound was purified by silica flash chromatography using DCM/ethyl acetate as solvent to give a yield of 20% (30 mg) of desired product. MS (m/e) [M+H] ($C_{31}H_{30}N_3O_6P$) calculated 571.19, observed 573.16.

Synthesis of Furimazine Phosphate (WZ-0314).

The mixture of furimazine methylene diallyl phosphate (30 mg, 0.053 mmol), Pd(PPh₃)₄ (12.1 mg, 0.011 mmol), and morpholine (45 mg, 0.525 mmol) in 10 ml of CH₂Cl₂ was stirred for 30 minutes. After removing the solvent, the compound was purified by HPLC using methanol and 10 mM NH₄Ac as eluent to give the desired product in a yield of 39% (10 mg). MS (m/e) [M+H] ($C_{25}H_{22}N_3O_6P$) calculated 491.12, observed 492.0.

Example 8. Synthesis of Furimazine Bis-Phosphate (WZ-0291)

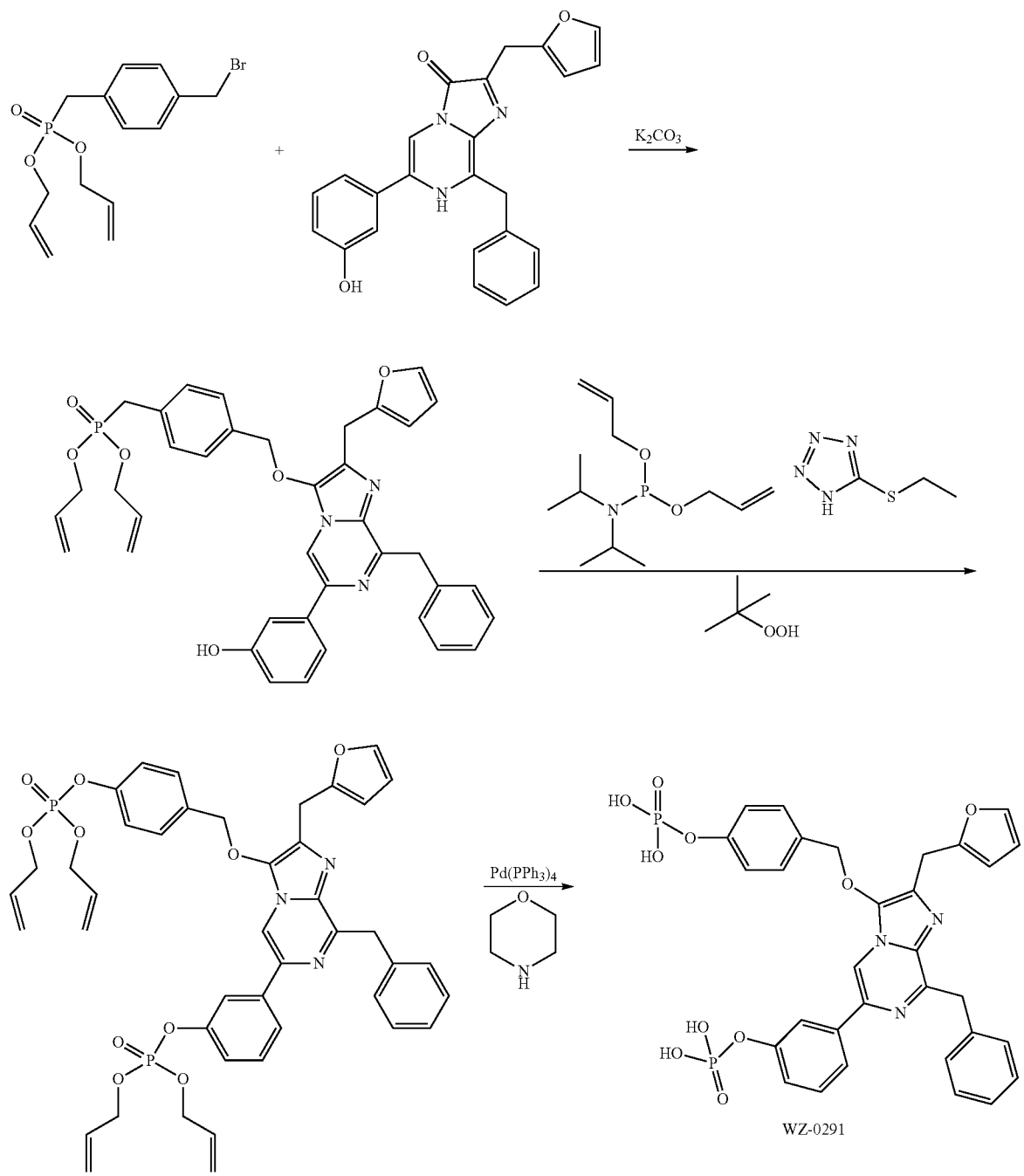

Synthesis of 3-Hydroxyl Furimazine Benzyl Diallyl Phosphate.

5 ml of dry DMF was purged with nitrogen for 30 minutes. To this solution, furimazine (100 mg, 0.30 mmol), p-bromobenzyl diallyl phosphate (96 mg, 0.28 mmol), and $K_2CO_3$ (0.42 g, 0.39 mmol) were added. The resultant mixture was stirred under nitrogen for 30 minutes at RT. The solution was diluted with 20 ml of DCM and washed with water and brine. The organic layer was dried over $Na_2SO_4$. The compound was purified by silica flash chromatography using heptane/ethyl acetate as solvent to yield 73 mg (44%) of desired product. MS (m/e) [M+H] ($C_{37}H_{34}N_3O_7P$) calculated 663.21, observed 664.3.

Synthesis of Furimazine Benzyl Bis-Diallyl Phosphate.

To the solution of 3-hydroxyl furimazine benzyl diallyl phosphate (65 mg, 0.098 mmol) and diallyl N,N-diisopropyl phosphoramidite (48 mg, 0.196 mmol) in 10 ml DCM, 5-ethyl thiol tetrazole (25 mg, 0.196 mmol) was added. The mixture was stirred for 30 minutes. TLC indicated the reaction was completed. t-BuOOH (0.196 ml, 5 M) was added, and the resultant mixture was stirred for another 10 minutes. The mixture was diluted with 30 ml of DCM and washed with $Na_2S_2O_3$ once and water twice. The organic layer was dried over $Na_2SO_4$. The compound was purified by silica flash chromatography using DCM/ethyl acetate as solvent to yield 62% (50 mg) of desired product. MS (m/e) [M+H] ($C_{43}H_{43}N_3O_{10}P_2$) calculated 823.24, observed 824.29.

Synthesis of Furimazine Bis-Phosphate (WZ-0291).

The mixture of furimazine methylene diallyl phosphate (54 mg, 0.066 mmol), $Pd(PPh_3)_4$ (18.9 mg, 0.016 mmol), and morpholine (57 mg, 0.655 mmol) in 10 ml of $CH_2Cl_2$ was stirred for 30 minutes. After removing the solvent, the compound was purified by HPLC using methanol and 10 mM $NH_4Ac$ as eluent to give the desired product in a yield of 57% (25 mg). MS (m/e) [M+H] ($C_{31}H_{27}N_3O_{10}P_2$) calculated 663.12, observed 664.1.

Example 9. Synthesis of Gly-Phe-Aminobenzyl Furimazine (WZ-0294)

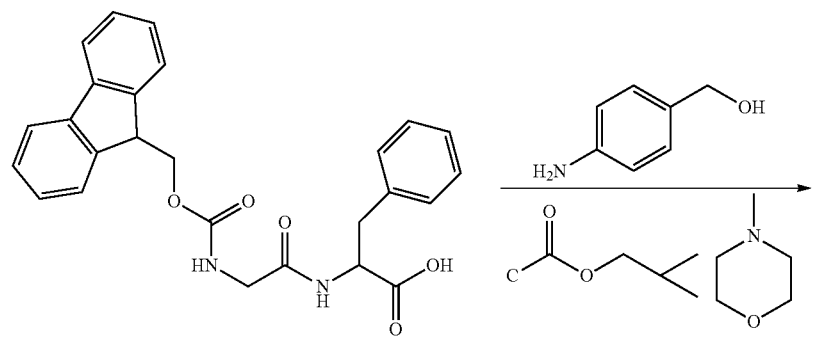

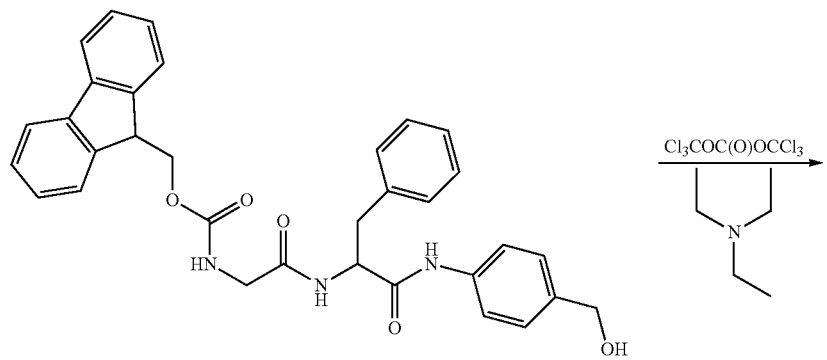

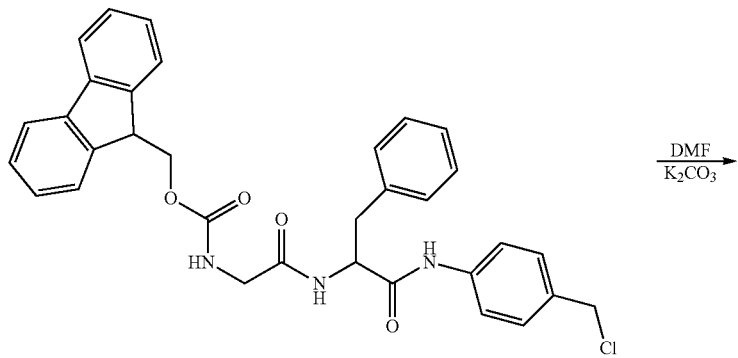

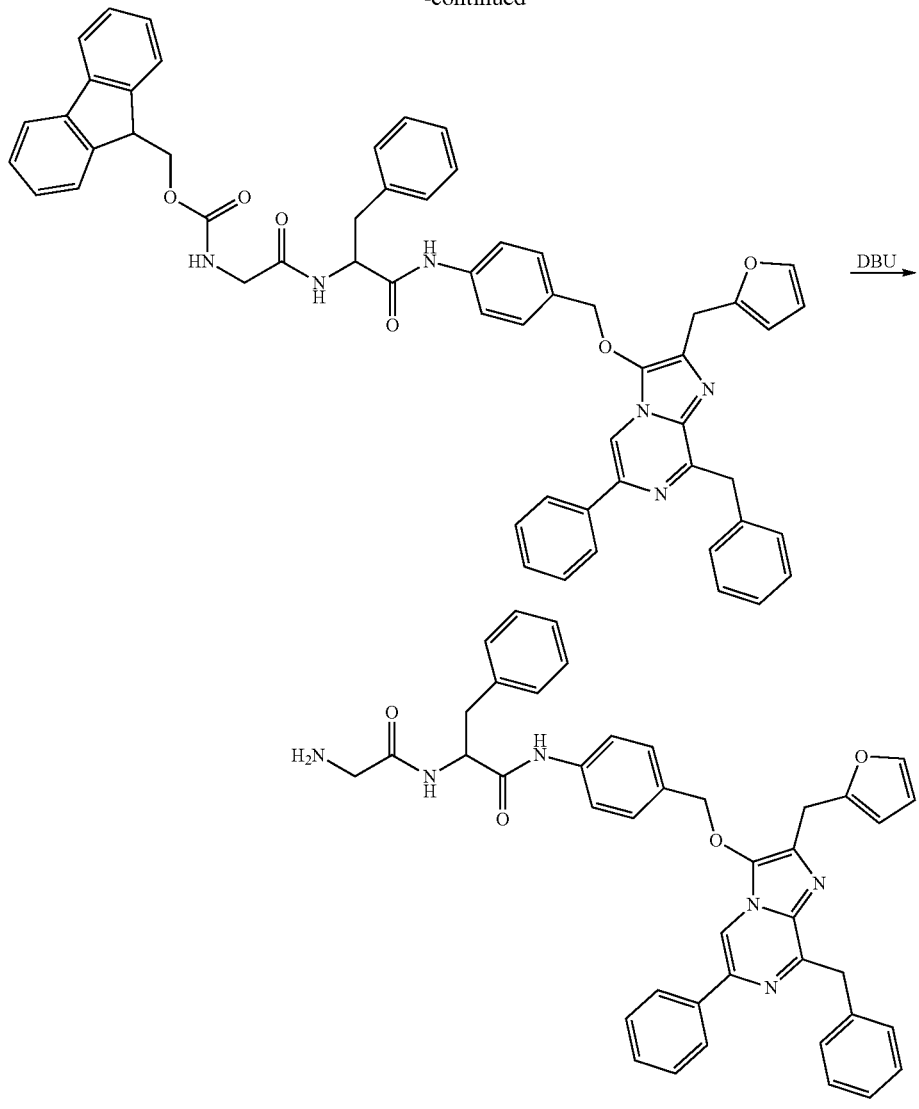

WZ-0294

Synthesis of Fmoc-Gly-Phe-Aminobenzyl Alcohol.

To the solution of Fmoc-Gly-Phe-COOH (2.0 g, 4.50 mmol) and isobutyl chloroformate (0.614 g, 4.50 mmol) in anhydrous THF, N-methyl morpholine at 0° C. was added. The mixture was stirred for 1 hour at 0° C. and then aminobenzyl alcohol was added. The resultant mixture was then stirred at RT for 1 hour. The solid was removed by filtration. After removing the solvent from filtrate, the compound was purified with a flash column using heptane/ethyl acetate as solvent to give a yield of 59% (1.45 g).

Synthesis of Fmoc-Gly-Phe-Aminobenzyl Choloride.

To the solution of Fmoc-Gly-Phe-aminobenzyl alcohol (500 mg, 0.909 mmol) and triphosgene (92 mg, 0.36 mmol) in 20 ml of anhydrous THF, TEA (230 mg, 0.317 mmol) at room temperature was added. The mixture was stirred for 2 hours. TLC was performed to confirm the reaction was complete. After removing the solid by filtration, the compound was purified with a flash column using heptane/ethyl acetate as solvent to give a yield of 50% (260 mg). MS (m/e) [M+H] ($C_{33}H_{30}N_3O_4$) calculated 567.19, observed 568.36.

Synthesis of Fmoc-Gly-Phe-Aminobenzyl Furimazine.

5 ml of dry DMF was purged with nitrogen for 30 minutes. To this solution, furimazine (60 mg, 0.16 mmol), Fmoc-Gly-Phe-aminobenzyl choloride (89 mg, 0.16 mmol), and $K_2CO_3$ (24 mg, 0.17 mmol) were added. The resultant mixture was stirred under nitrogen for 30 minutes at RT. The solution was diluted with 20 ml of DCM and washed with water and brine. The organic layer was dried over $Na_2SO_4$. The compound was purified by silica flash chromatography using heptane/ethyl acetate as solvent. The compound was further purified by HPLC using 10 mM ammonium acetate and ACN as solvent to give a yield of 10% (15 mg) of desired product. MS (m/e) [M+H] ($C_{57}H_{48}N_6O_6$) calculated 912.36, observed 913.59.

Synthesis of Gly-Phe-Aminobenzyl Furimazine (WZ-0294).

To the solution of Fmoc-Gly-Phe-aminobenzyl furimazine (10 mg, 0.011 mmol) in 5 ml of DCM, DBU (2.50 mg, 0.016 mmol) was added. The mixture was stirred for 15 minutes. The reaction was quenched by adding a drop of acetic acid. After removing the solvent, the compound was purified by HPLC using 10 mM ammonium acetate and ACN as solvent to give a yield of 79% (6 mg) of desired product. MS (m/e) [M−H] ($C_{42}H_{38}N_6O_4$) calculated 690.30, observed 689.19.

Example 10. Synthesis of
Bis-Gly-Phe-Aminobenzyl Furimazine (WZ-0299)
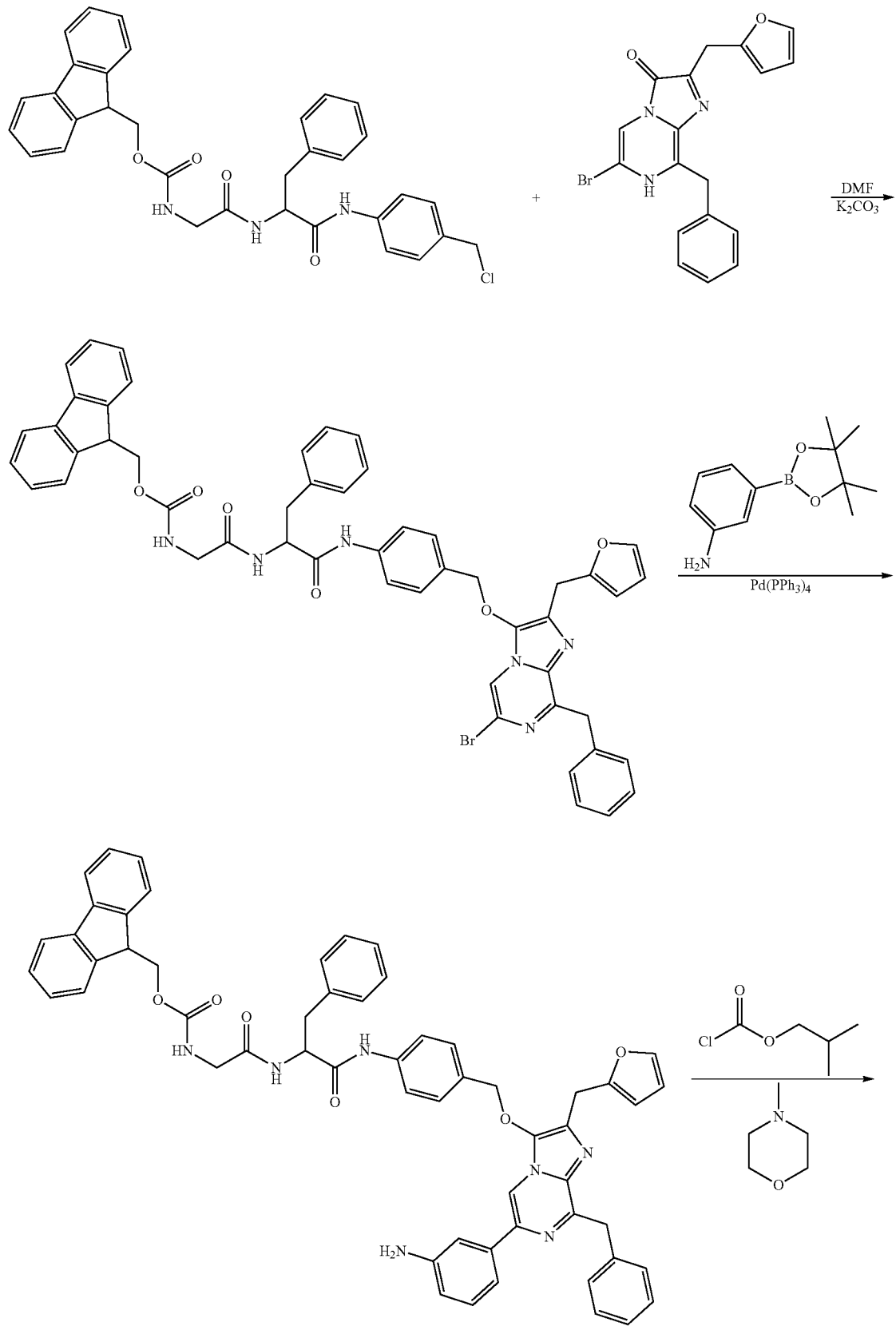

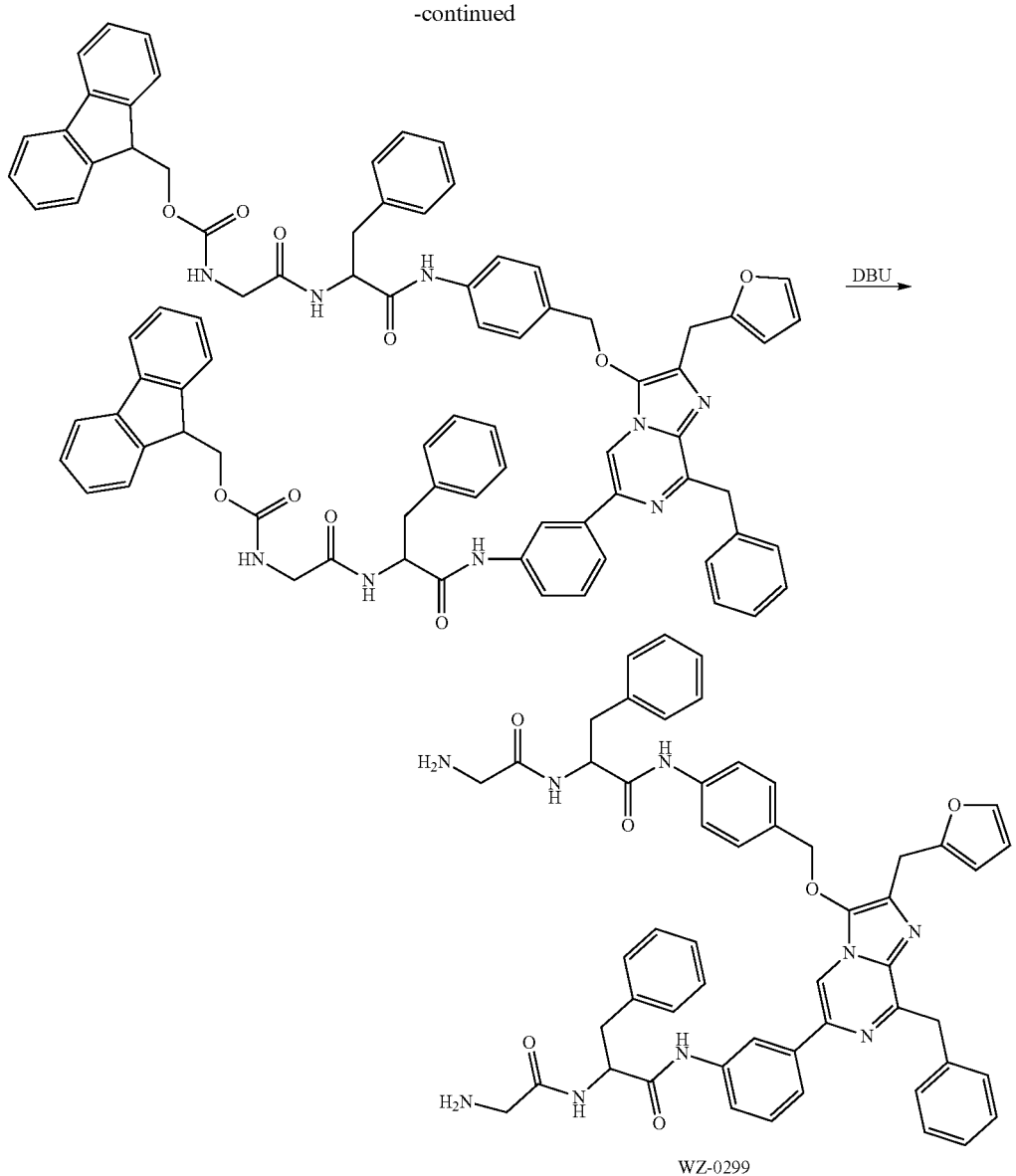

WZ-0299

Synthesis of Fmoc-Gly-Phe-Aminobenzyl Bromofurimazine.

Fmoc-Gly-Phe-aminobenzyl chloride (177 mg, 0.31 mmol) and KI (43 mg, 0.26 mmol) in 5 ml of dry DMF were stirred under nitrogen for 30 minutes. To this mixture, bromo-furimazine (100 mg, 0.26 mmol) and $K_2CO_3$ (53 mg, 0.39 mmol) were added. The resultant mixture was stirred under nitrogen for 30 minutes at RT. The solution was diluted with 20 ml of DCM and washed with water and brine. The organic layer was dried over $Na_2SO_4$. The compound was purified by silica flash chromatography using heptane/ethyl acetate as solvent to yield 27% (65 mg) of desired product. MS (m/e) [M+H] ($C_{51}H_{43}BrN_6O_6$) calculated 914.24, observed 915.40, 917.58 (1:1).

Synthesis of Fmoc-Gly-Phe-Aminobenzyl 3-aminofurimazine.

Fmoc-Gly-Phe-aminobenzyl bromofurimazine (65 mg, 0.071 mmol) was dissolved in 5 ml of dioxane and stirred under $N_2$ for 10 minutes. Pd(PPh$_3$)$_4$ (16.4 mg, 0.015 mmol), 3-aminophenylborate (31 mg, 0.014 mmol), and $Cs_2CO_3$ (46 mg, 0.014 mmol) and 1 ml of water were added. The mixture was heated up to 80° C. for 30 minutes. TLC and LC-MS confirmed the reaction was completed. 20 ml of DCM was added, the aqueous layer removed, and organic layer washed with water and dried over $Na_2SO_4$. The compound was purified by silica flash chromatography using heptane/ethyl acetate as solvent to yield 46% (30 mg) of desired product. MS (m/e) [M+H] ($C_{57}H_{49}BrN_7O_6$) calculated 927.37, observed 928.51.

Synthesis of Bis-Fmoc-Gly-Phe-Aminobenzyl Furimazine.

To the solution of Fmoc-Gly-Phe-COOH (172 mg, 0.39 mmol) in 10 ml of anhydrous THF, NMP (65 mg, 0.65 mmol) was added. The mixture was sonicated to ensure the solid going to the solution. At 0° C., isobutyl chloroformate (53 mg, 0.39 mmol) was added. The resultant mixture was stirred for 1 hour. The solution of Fmoc-GlyPhe-3-amino-FRZ was added, and the mixture was stirred for 30 minutes.

The compound was purified by silica flash chromatography using heptane/ethyl acetate as solvent to yield 23% (10 mg) of desired product. MS (m/e) [M+H] ($C_{83}H_{71}N_9O_{10}$) calculated 1353.53, observed 1354.79.

Synthesis of Bis-Gly-Phe-Aminobenzyl Furimazine (WZ-0299).

To the solution of bis-Fmoc-Gly-Phe-aminobenzyl furimazine (10 mg, 0.08 mmol) in 5 ml of DCM, DBU (3.4 mg, 0.022 mmol) was added. The mixture was stirred for 15 minutes. The reaction was quenched by adding a drop of acetic acid. After removing the solvent, the compound was purified by HPLC using 10 mM ammonium acetate and ACN as solvent to yield 59% (4 mg) of desired product. MS (m/e) [M−H] ($C_{53}H_{51}N_9O_6$) calculated 909.40, observed 908.23.

The following compounds were prepared using the above procedures.

| compound | Structure | Yield (%) | MS [M + H] |
|---|---|---|---|
| WZ-0262 | 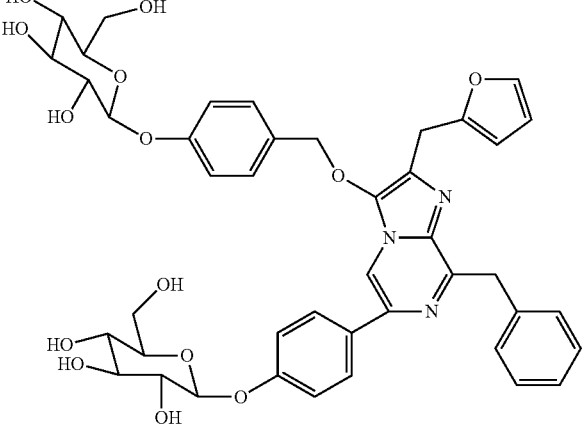 (2S,3R,4S,5S,6R)-2-(4-(8-benzyl-2-(furan-2-ylmethyl)-3-((4-(((2S,3R,4S,5S,6R)-3,4,5-trihydroxy-6-(hydroxymethyl)tetrahydro-2H-pyran-2-yl)oxy)benzyl)oxy)imidazo[1,2-a]pyrazin-6-yl)phenoxy)-6-(hydroxymethyl)tetrahydro-2H-pyran-3,4,5-triol | 84 | 828.28 |
| WZ-0291 | 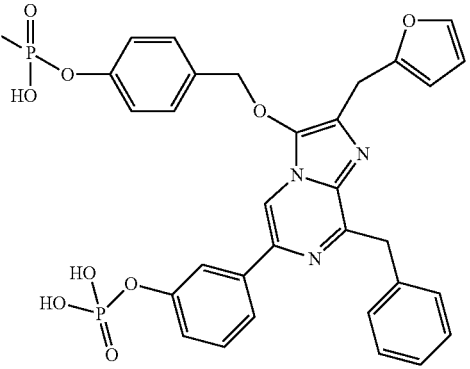 4-(((8-benzyl-2-(furan-2-ylmethyl)-6-(3-(phosphonooxy)phenyl)imidazo[1,2-a]pyrazin-3-yl)oxy)methyl)phenyl dihydrogen phosphate | 57 | 664.1 |

-continued

| compound | Structure | Yield (%) | MS [M + H] |
|---|---|---|---|
| WZ-0299 | 2-(2-aminoacetamido)-N-(3-(3-((4-(2-(2-aminoacetamido)-3-phenylpropanamido)benzyl)oxy)-8-benzyl-2-(furan-2-ylmethyl)imidazo[1,2-a]pyrazin-6-yl)phenyl)-3-phenylpropanamide | 59% | 908.23 (M − H) |

The following compounds were prepared using the above procedures.

40

| comparative compound | Structure | Yield (%) | MS [M + H] |
|---|---|---|---|
| WZ-0246 | (2S,3R,4S,5S,6R)-2-(4-(((8-benzyl-2-(furan-2-ylmethyl)-6-phenylimidazo[1,2-a]pyrazin-3-yl)oxy)methyl)phenoxy)-6-(hydroxymethyl)tetrahydro-2H-pyran-3,4,5-triol | 91 | 650.44 |

-continued

| comparative compound | Structure | Yield (%) | MS [M + H] |
|---|---|---|---|
| WZ-0261 | (2S,3R,4S,5S,6R)-2-((8-benzyl-2-(furan-2-ylmethyl)-6-phenylimidazo[1,2-a]pyrazin-3-yl)oxy)-6-(hydroxymethyl)tetrahydro-2H-pyran-3,4,5-triol | 85 | 545.18 |
| WZ-0263 | 4-(((8-benzyl-2-(furan-2-ylmethyl)-6-phenylimidazo[1,2-a]pyrazin-3-yl)oxy)methyl)phenyl dihydrogen phosphate | 78 | 568.1 |
| WZ-0265 | 8-benzyl-2-(furan-2-ylmethyl)-6-phenylimidazo[1,2-a]pyrazin-3-yl dihydrogen phosphate | 72 | 462.02 |

| comparative compound | Structure | Yield (%) | MS [M + H] |
|---|---|---|---|
| WZ-0314 | ((8-benzyl-2-(furan-2-ylmethyl)-6-phenylimidazo[1,2-a]pyrazin-3-yl)oxy)methyl phosphate | 39 | 492.0 |
| WZ-0294 | 2-(2-aminoacetamido)-N-(4-(((8-benzyl-2-(furan-2-ylmethyl)-6-phenylimidazo[1,2-a]pyrazin-3-yl)oxy)methyl)phenyl)-3-phenylpropanamide | 79 | 689.19 (M − H) |

The following prophetic compounds can be prepared using procedures similar to the ones used to synthesize compounds WZ-0246 and WZ-0291, respectively.

| prophetic compound | Structure | Yield (%) | MS [M + H] |
|---|---|---|---|
| | 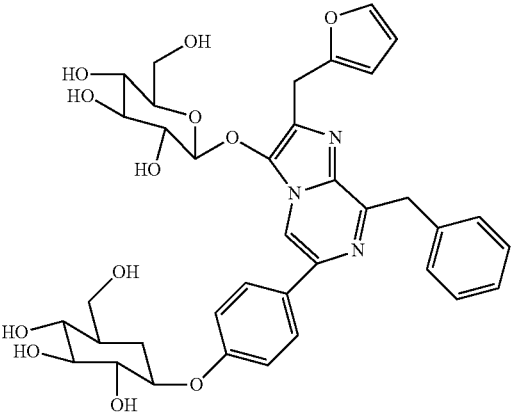<br>(2S,3R,4S,5S,6R)-2-(4-(8-benzyl-2-(furan-2-ylmethyl)-3-(((2S,3R,4S,5S,6R)-3,4,5-trihydroxy-6-(hydroxymethyl)tetrahydro-2H-pyran-2-yl)oxy)imidazo[1,2-a]pyrazin-6-yl)phenoxy)-6-(hydroxymethyl)tetrahydro-2H-pyran-3,4,5-triol | | |
| | 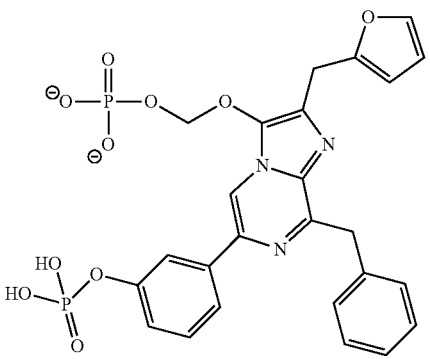<br>((8-benzyl-2-(furan-2-ylmethyl)-6-(3-(phosphonooxy)phenyl)imidazo[1,2-a]pyrazin-3-yl)oxy)methyl phosphate | | |

Example 11. Luminescent Properties

Glucosidase Assays

To the solution of 50 μl of furimazine mono- or bis-glucoside compound (100 μM) in NanoGlo buffer and 50 μl of NanoGlo buffer containing 1 ng/mL Nanoluc was added 11 μl of thermal stable β-glucosidase (Sigma) in PBS with final concentration of 1 Unit/ml/μM, and the light output was measured over time. The background of pro-substrate was measured under same condition without β-glucosidase.

Alkaline phosphatase assays. To the solution of 50 μl furimazine mono- or bis-phosphate compound (50 μM) and 50 μL of NanoGlo buffer containing 1 ng/mL Nanoluc was added, then alkaline phasphatase (Sigma) in PBS with final concentration at 1 Unit/ml/μM was added, and the light output was measured over time. The background of pro-substrate was measured under same condition without adding alkaline phasphotase.

Cathepsin C assay. To the solution of 50 μl of furimazine mono- or bis-Gly-Phe compound (50 μM) in 1:1 NanoGlo and nanopure water containing DTT 5 mM and 50L of 1 ng/mL Nanoluc buffer in 1:1 NanoGlo and nanopure water containing 5 mM DTT was added, then 10 μL of Cathepsin C (Sigma C8511 from bovine spleen) at final concentration of 0.1 U/well was added. The light output was measured over time. The background of pro-substrate was measured under same condition without adding Cathepsin C.

The synthesized coelenterazine analogues (compounds of formula (I)) were evaluated for their background and signal/background ratio.

FIG. 1 and Tables 1 and 2 show that bis-protected, WZ-0262, has a background signal close to instrument noise and has a significantly higher signal-to-background ratio as compared to the corresponding mono-protected analogues, WZ-0261 and WZ-0246. The background of WZ-0262 was ~200 fold lower than the corresponding mon-protected analogue WZ-0246. The data also shows that these analogues are very reactive toward glucosidase and that the bis-protected analogue WZ-0262 is ~100 fold higher than the corresponding mono-protected analogue at the initial time point. The fast signal drop may be due to 6-hydroxy-furimazine self-inhibition, but this will not be a problem at low conversion and will not affect the detection limit.

TABLE 1

Back ground RLU

| Time (hr.) | WZ-0261 Mono-G | WZ-0246 Mong-Bz-G | WZ-0262 Bis-Bz-G |
|---|---|---|---|
| 0 | 522 | 10,028 | 87 |
| 0.1 | 530 | 10,884 | 39 |
| 0.25 | 557 | 12,298 | 32 |
| 0.5 | 760 | 13,047 | 21 |
| 1 | 960 | 18,529 | 26 |
| 1.5 | 1114 | 20,751 | 26 |
| 2 | 1322 | 24,489 | 20 |
| 3 | 1521 | 29,692 | 14 |
| 4 | 1580 | 33,514 | 25 |
| 5 | 1729 | 37,181 | 26 |
| 6 | 1653 | 40,543 | 22 |
| 16 | 584 | 23,092 | 26 |

TABLE 2

Signal to Background

| Time (hr.) | WZ-261 Mono-G | WZ-0246 Mong-Bz-G | WZ-0262 Bis-Bz-G |
|---|---|---|---|
| 0 | 62,718 | 3,235 | 340,753 |
| 0.1 | 59,553 | 2,915 | 134,646 |
| 0.25 | 53,746 | 2,426 | 73,734 |
| 0.5 | 35,470 | 2,193 | 58,191 |
| 1 | 23,057 | 1,172 | 21,501 |
| 1.5 | 16,545 | 926 | 12,822 |
| 2 | 11,704 | 627 | 11,569 |
| 3 | 7,426 | 385 | 11,041 |
| 4 | 5,940 | 264 | 5,297 |
| 5 | 4,284 | 210 | 4,585 |
| 6 | 3,515 | 157 | 5,060 |
| 16 | 1,581 | 36 | 2708 |

Figure 2:
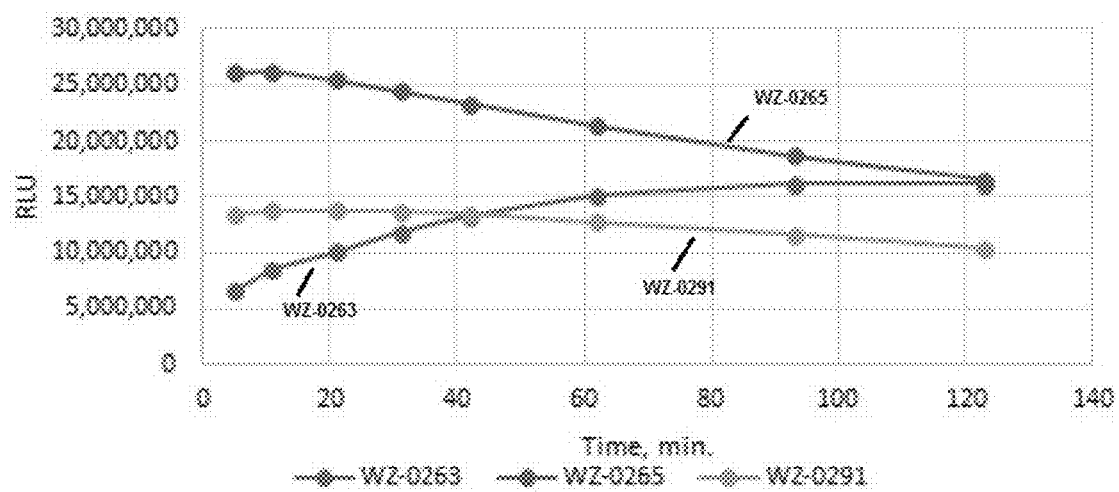
FIG. 2 shows the luminescent signal output of the disclosed dual-protected compounds relative to mono-protected analogues.

FIG. 2 and Tables 3 and 4 show that bis-protected WZ-0291 has low background compared to the corresponding mono-protected analogue WZ-0263 and has a significantly higher signal-to-background ratio as compared to the mono-protected analogues WZ-0263 and WZ-0265.

TABLE 3

Background RLU

| Time (min.) | WZ-0263 Mono- | WZ-0265 | WZ-0291 Bis- | Blank |
|---|---|---|---|---|
| 5 | 32,464 | 9,033,396 | 713 | 23 |
| 11 | 36,745 | 9,181,168 | 739 | 21 |
| 21 | 42,522 | 9,310,668 | 723 | 19 |
| 31 | 48,399 | 9,376,837 | 723 | 14 |
| 42 | 54,309 | 9,394,555 | 722 | 15 |
| 62 | 65,661 | 9,359,460 | 678 | 14 |
| 93 | 80,929 | 9,089,377 | 680 | 15 |
| 123 | 94,825 | 8,772,026 | 704 | 17 |

TABLE 4

Signal to Background

| Time (min.) | WZ-0263 | WZ-0265 | WZ-0291 |
|---|---|---|---|
| 5 | 203 | 3 | 18,907 |
| 11 | 232 | 3 | 18,699 |
| 21 | 236 | 3 | 19,076 |
| 31 | 245 | 3 | 18,846 |
| 42 | 244 | 2 | 18,568 |
| 62 | 230 | 2 | 18,861 |

TABLE 4-continued

Signal to Background

| Time (min.) | WZ-0263 | WZ-0265 | WZ-0291 |
|---|---|---|---|
| 93 | 200 | 2 | 17,014 |
| 123 | 170 | 2 | 14,664 |

Figure 3:
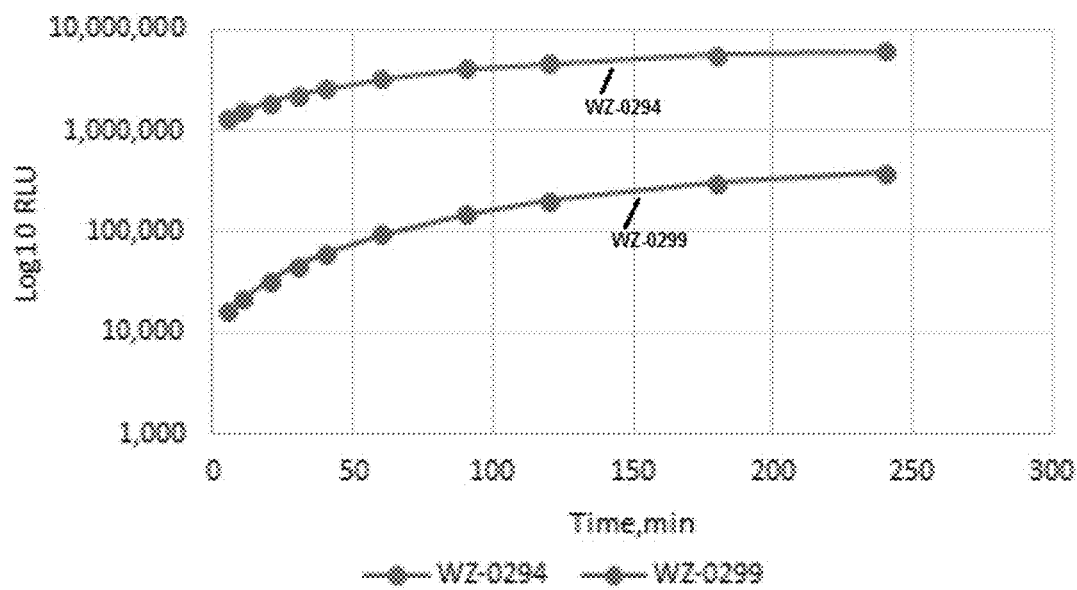
FIG. 3 shows the luminescent signal output of the disclosed dual-protected compounds relative to mono-protected analogues.

FIG. 3 and Tables 5 and 6 show that bis-protected WZ-0299 has a background down to instrument noise, and has a significantly higher signal-to-background ratio as compared to the corresponding mono-protected analogue WZ-0294.

TABLE 5

Background RLU

| Time (min.) | WZ-0294 Mono- | WZ-0299 Bis- | Blank |
|---|---|---|---|
| 5 | 8,974 | 20 | 22 |
| 10 | 9,538 | 21 | 15 |
| 20 | 10,825 | 18 | 15 |
| 30 | 11,741 | 14 | 15 |
| 40 | 12,664 | 14 | 16 |
| 60 | 14,295 | 15 | 11 |
| 90 | 16,141 | 16 | 13 |
| 120 | 17,178 | 12 | 9 |
| 180 | 20,562 | 17 | 10 |
| 240 | 23,705 | 15 | 8 |
| 938 | 15,995 | 12 | 9 |

TABLE 6

Signal to Background

| S/B Time (min.) | Mono WZ-0294 | Bis WZ-0299 |
|---|---|---|
| 5 | 151 | 751 |
| 10 | 163 | 1,464 |
| 20 | 180 | 2,256 |
| 30 | 197 | 3,036 |
| 40 | 210 | 3,941 |
| 60 | 232 | 8,514 |
| 90 | 255 | 11,997 |
| 120 | 275 | 23,011 |
| 180 | 273 | 29,836 |
| 240 | 259 | 46,864 |
| 938 | 142 | 17,386 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I)

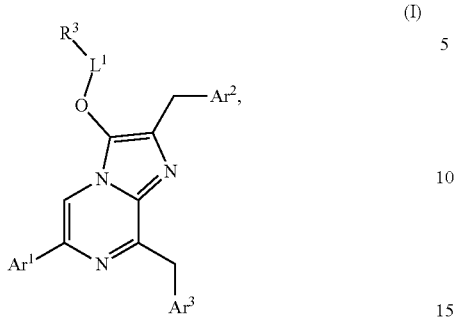

(I)

or a tautomer, or a salt thereof, wherein
$Ar^1$, $Ar^2$, and $Ar^3$ are each independently selected from the group consisting of aryl and heteroaryl, wherein $Ar^1$, $Ar^2$, and $Ar^3$ are each optionally substituted, provided that one of $Ar^1$, $Ar^2$, or $Ar^3$ is substituted by —X-$L^2$-$R^6$;
X is O, S, or $NR^x$, wherein $R^x$ is hydrogen or $C_1$-$C_6$-alkyl;
$L^1$ and $L^2$ are each independently selected from the group consisting of a bond and a linker of 1 to 50 atoms, wherein $L^1$ and $L^2$ are each optionally substituted; and
$R^3$ and $R^6$ are each independently selected from the group consisting of a peptide, an amino acid, a saccharide, and a phosphate.

2. The compound of claim 1, of formula:

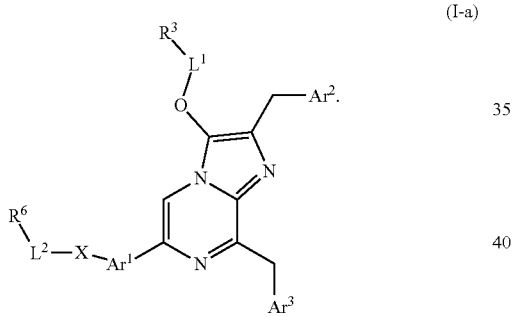

(I-a)

3. The compound of claim 1, wherein $Ar^2$ is furyl or phenyl.

4. The compound of claim 1, wherein X is O.

5. The compound of claim 1, wherein
$L^1$ and $L^2$ are each independently a bond, alkylene, or arylenealkylene;
wherein one or more of the —$CH_2$— moieties in the alkylene chain portion of alkylene or arylenealkylene are optionally replaced by C=O, C=S, $NR^{x1}$, O, S, NO, SO and $SO_2$, wherein $R^{x1}$ at each occurrence is independently selected from the group consisting of hydrogen and $C_1$-$C_6$-alkyl;
wherein alkylene and arylenealkylene are each independently substituted with 0, 1, 2, 3, 4, 5, 6, 7, 8, 9, or 10 substituents independently selected from the group consisting of halogen, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

6. The compound of claim 1, wherein $L^1$ and $L^2$ are each independently selected from the group consisting of:
a bond;

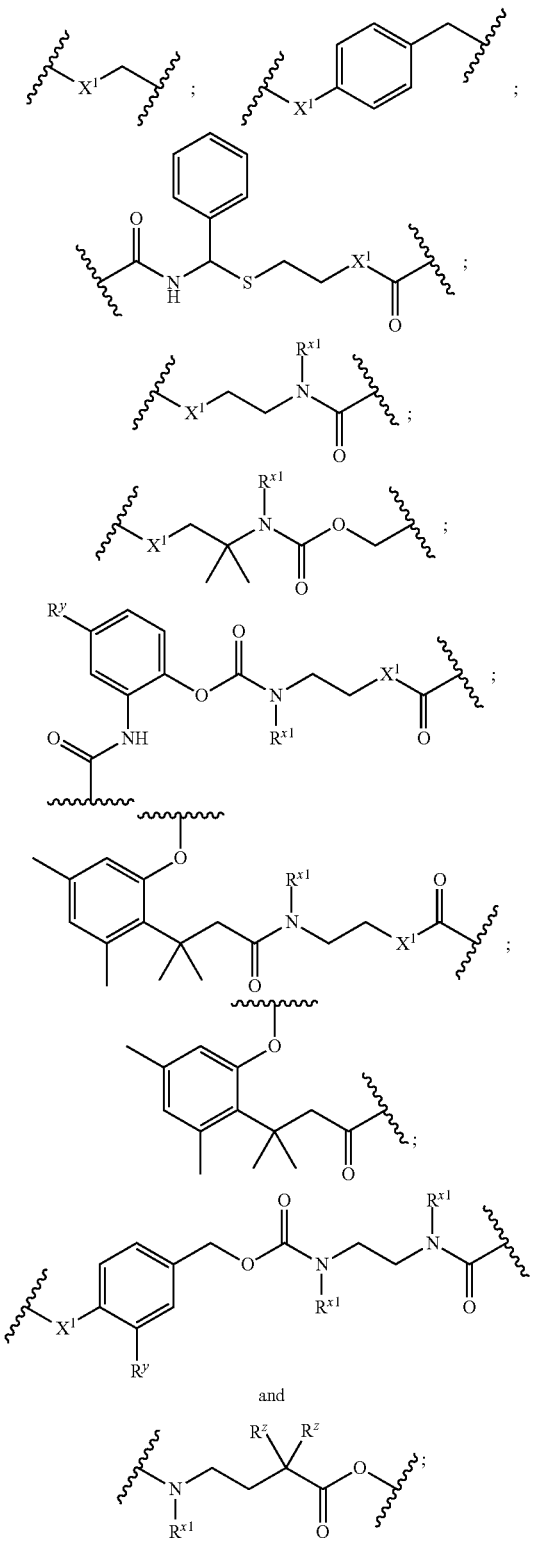

and wherein $R^{x1}$ at each occurrence is independently selected from the group consisting of hydrogen and $C_1$-$C_6$-alkyl; $R^y$ is selected from the group consisting of hydrogen, halogen, and nitro; $R^z$ at each occurrence is independently selected from the group consisting of hydrogen and $C_1$-$C_6$-alkyl; and $X^1$ is selected from the group consisting of $NR^{x2}$, O, and S, wherein $R^{x2}$ is hydrogen or $C_1$-$C_6$-alkyl.

7. The compound of claim 1, wherein $L^1$ and $L^2$ are each independently selected from the group consisting of:

a bond;

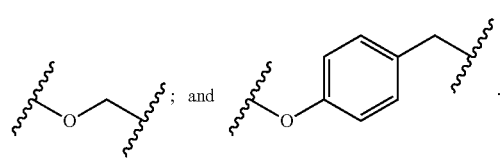

8. The compound of claim 1, wherein $L^1$ and $L^2$ are each a bond.

9. The compound of claim 1, wherein $R^3$ and $R^6$ are each independently selected from the group consisting of:

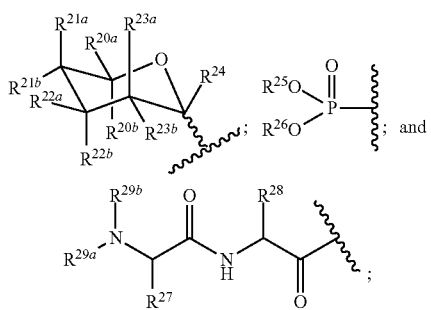

wherein
- $R^{20a}$ and $R^{20b}$ are each independently selected from the group consisting of hydrogen, halogen, and $C_1$-$C_6$-alkyl optionally substituted with 1, 2, 3, or 4 —$OR^{30}$ groups and optionally 1 oxo group, wherein $R^{30}$ at each occurrence is independently selected from the group consisting of hydrogen, $C_1$-$C_6$-alkyl, and $C(=O)R^{31}$, wherein $R^{31}$ is $C_1$-$C_6$-alkyl;
- $R^{21a}$, $R^{21b}$, $R^{22a}$, $R^{22b}$, $R^{23a}$, and $R^{23b}$ at each occurrence are each independently selected from the group consisting of hydrogen, halogen, $OR^{32}$ and $NR^{33}R^{34}$, wherein $R^{32}$—$R^{34}$ at each occurrence are each independently selected from the group consisting of hydrogen, $C_1$-$C_6$-alkyl, and $C(=O)R^{35}$, wherein $R^{35}$ is hydrogen or $C_1$-$C_6$-alkyl;
- $R^{24}$ at each occurrence is independently selected from the group consisting of hydrogen and $C(=O)R^{36}$, wherein $R^{36}$ is selected from the group consisting of hydrogen, $C_1$-$C_6$-alkyl, —OH, and —O—$C_1$-$C_6$-alkyl;
- $R^{25}$ and $R^{26}$ are each independently selected from the group consisting of hydrogen, and $C_1$-$C_6$-alkyl;
- $R^{27}$ and $R^{28}$ are each independently selected from the group consisting of:

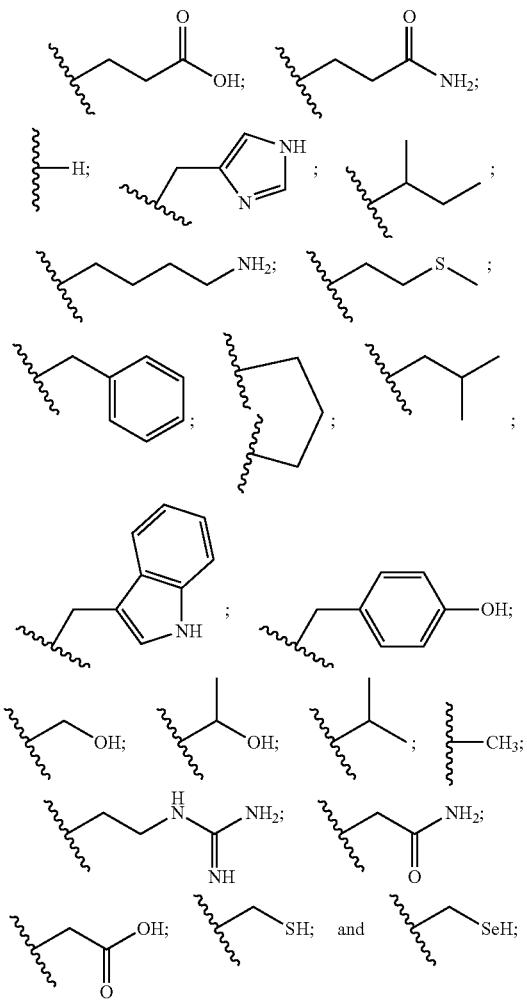

and
$R^{29a}$ and $R^{29b}$ are each independently hydrogen, or $R^{29a}$ and $R^{27}$ together with the atoms to which they are attached can form a five-membered ring.

10. The compound of claim 1, wherein $R^3$ and $R^6$ are each independently selected from the group consisting of:

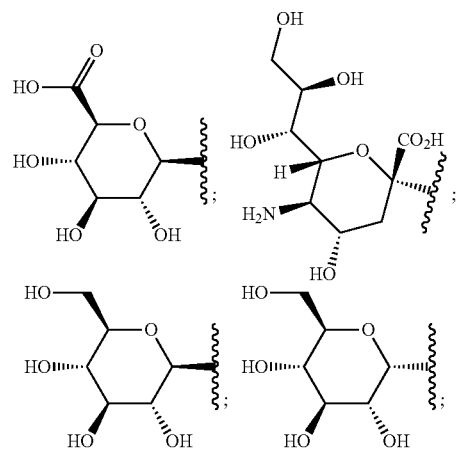

-continued

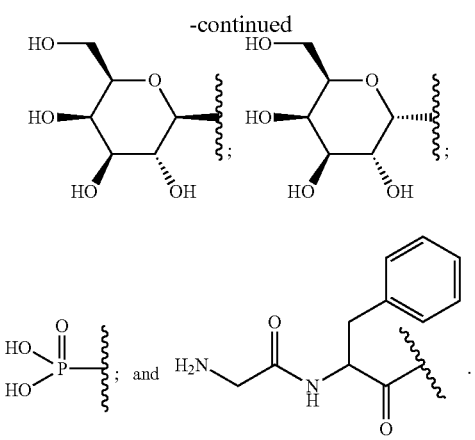

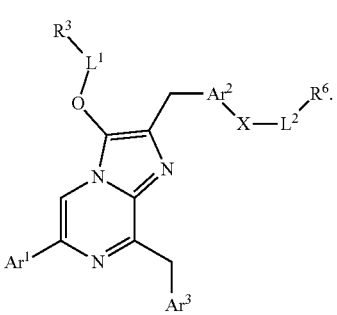

11. The compound of claim 1, selected from the group consisting of:

(2S,3R,4S,5S,6R)-2-(4-(8-benzyl-2-(furan-2-ylmethyl)-3-((4-(((2S,3R,4S,5S,6R)-3,4,5-trihydroxy-6-(hydroxymethyl)tetrahydro-2H-pyran-2-yl)oxy)benzyl)oxy)imidazo[1,2-a]pyrazin-6-yl)phenoxy)-6-(hydroxymethyl)tetrahydro-2H-pyran-3,4,5-triol;

4-(((8-benzyl-2-(furan-2-ylmethyl)-6-(3-(phosphonooxy)phenyl)imidazo[1,2-a]pyrazin-3-yl)oxy)methyl)phenyl dihydrogen phosphate;

2-(2-aminoacetamido)-N-(3-(3-((4-(2-(2-aminoacetamido)-3-phenylpropanamido)benzyl)oxy)-8-benzyl-2-(furan-2-ylmethyl)imidazo[1,2-a]pyrazin-6-yl) phenyl)-3-phenylpropanamide;

(2S,3R,4S,5S,6R)-2-(4-(8-benzyl-2-(furan-2-ylmethyl)-3-(((2S,3R,4S,5S,6R)-3,4,5-trihydroxy-6-(hydroxymethyl)tetrahydro-2H-pyran-2-yl)oxy)imidazo[1,2-a]pyrazin-6-yl)phenoxy)-6-(hydroxymethyl; and ((8-benzyl-2-(furan-2-ylmethyl)-6-(3-(phosphonooxy)phenyl)imidazo[1,2-a]pyrazin-3-yl)oxy)methyl phosphate;

or a tautomer, or a salt thereof.

12. A kit comprising a compound of claim 1 and a buffer reagent.

13. The kit of claim 12, further comprising a luciferase.

14. A method for detecting luminescence in a sample, the method comprising contacting a sample with a compound of claim 1;
    adding to the sample with a coelenterazine-utilizing luciferase, if it is not present in the sample; and
    detecting luminescence.

15. The method of claim 14, wherein the sample contains live cells.

16. The method of claim 14, wherein a coelenterazine-utilizing luciferase was already present in the sample.

17. A method for detecting luminescence in a transgenic animal comprising administering a compound of claim 1 to a transgenic animal; and
    detecting luminescence;
    wherein the transgenic animal expresses a coelenterazine-utilizing luciferase.

18. The compound of claim 1, of formula:

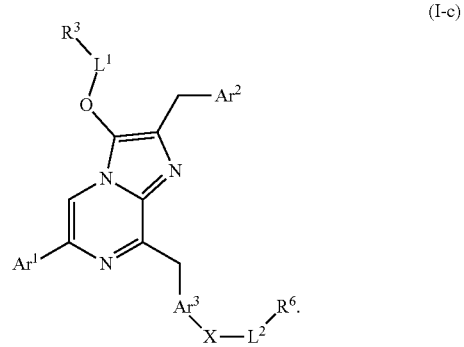

(I-b)

19. The compound of claim 1, of formula:

(I-c)

20. The compound of claim 2, wherein
Ar² is furyl or phenyl;
X is O;
L¹ and L² are each independently selected from the group consisting of:
a bond,

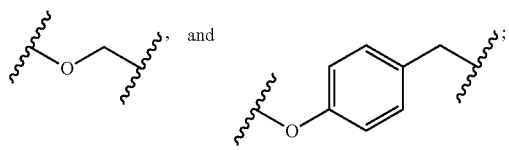

and

R³ and R⁶ are each independently selected from the group consisting of:

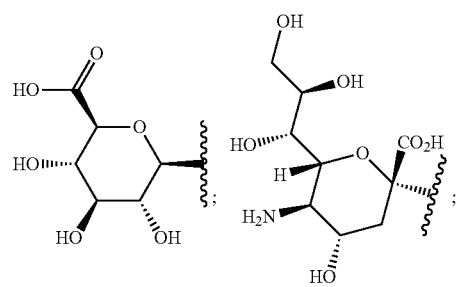

-continued
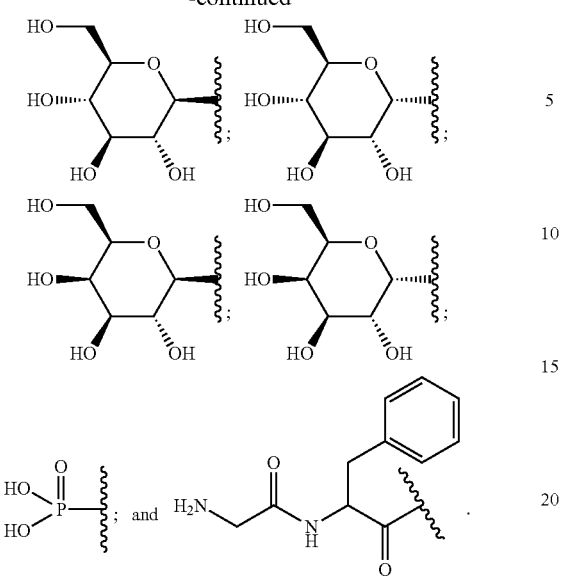
* * * * *

UNITED STATES PATENT AND TRADEMARK OFFICE
CERTIFICATE OF CORRECTION

PATENT NO. : 10,316,070 B2
APPLICATION NO. : 15/699846
DATED : June 11, 2019
INVENTOR(S) : Wenhui Zhou, Joel R. Walker and Poncho Meisenheimer Page 1 of 1

It is certified that error appears in the above-identified patent and that said Letters Patent is hereby corrected as shown below:

In the Claims

Claim 11, Column 97, Line 40 reads:
"pyrazin-6-yl)phenoxy)-6-(hydroxymethyl; and"

Whereas it should read:
"pyrazin-6-yl)phenoxy)-6-(hydroxymethyl)tetrahydro-2H-pyran-3,4,5-triol; and"

Signed and Sealed this
Twenty-fourth Day of November, 2020

Andrei Iancu
*Director of the United States Patent and Trademark Office*